US011896398B2

(12) United States Patent
Zhou et al.

(10) Patent No.: US 11,896,398 B2
(45) Date of Patent: *Feb. 13, 2024

(54) CORONARY ARTERY DISEASE DETECTION SIGNAL PROCESSING SYSTEM AND METHOD

(71) Applicant: AUSCULSCIENCES, INC., Vienna, VA (US)

(72) Inventors: Jun Zhou, Kanata (CA); Md Shahidul Islam, Ottawa (CA); Jikang Zeng, Kanata (CA); Daniel Labonté, Ottawa (CA); Simon Martin, Gatineau (CA); Brady Laska, Arnprior (CA); Sergey A. Telenkov, Ottawa (CA)

(73) Assignee: AUSCULSCIENCES, INC., Vienna, VA (US)

( * ) Notice: Subject to any disclaimer, the term of this patent is extended or adjusted under 35 U.S.C. 154(b) by 269 days.

This patent is subject to a terminal disclaimer.

(21) Appl. No.: 17/360,716

(22) Filed: Jun. 28, 2021

(65) Prior Publication Data

US 2021/0321948 A1    Oct. 21, 2021

Related U.S. Application Data

(63) Continuation of application No. 16/166,107, filed on Oct. 21, 2018, now Pat. No. 11,045,144.
(Continued)

(51) Int. Cl.
*A61B 5/318* (2021.01)
*A61B 7/04* (2006.01)
(Continued)

(52) U.S. Cl.
CPC ............ *A61B 5/7203* (2013.01); *A61B 5/318* (2021.01); *A61B 5/721* (2013.01); *A61B 5/7225* (2013.01);
(Continued)

(58) Field of Classification Search
CPC ....... A61B 5/7203; A61B 5/318; A61B 5/721; A61B 5/7225; A61B 5/7257;
(Continued)

(56) References Cited

U.S. PATENT DOCUMENTS

| 6,053,872 A | 4/2000 | Mohler |
| 7,914,468 B2 | 3/2011 | Shalon et al. |

(Continued)

FOREIGN PATENT DOCUMENTS

| CN | 201727511 U | 2/2011 |
| CN | 102599928 A | 7/2012 |

(Continued)

OTHER PUBLICATIONS

STMicroelectronics, "STC3100 Battery monitor IC with Coulomb counter/gas gauge," Jan. 2009, 21 pp.

(Continued)

*Primary Examiner* — Gary Jackson
*Assistant Examiner* — Alexander M Eisenberg
(74) *Attorney, Agent, or Firm* — Kurt L. VanVoorhies

(57) ABSTRACT

An auscultatory sound-or-vibration sensor electronic test signal applied to a sound generator generates an acoustic sound signal, responsive to which an auscultatory sound-or-vibration sensor in proximity to the sound generator generates a corresponding auscultatory sound signal. The auscultatory sound-or-vibration sensor electronic test signal incorporates a plurality of frequency components, each frequency component of which incorporates an integral number of wavelengths and is terminated following a duration of time corresponding to the integral number of wavelengths after that frequency component is applied to the corresponding sound generator. A determination of whether or not the auscultatory sound-or-vibration sensor is func- (Continued)

tioning properly is made responsive to an analysis of a Fourier Transform of the auscultatory sound signal.

21 Claims, 33 Drawing Sheets

Related U.S. Application Data

(60) Provisional application No. 62/575,364, filed on Oct. 20, 2017.

(51) Int. Cl.
| | | |
|---|---|---|
| *H03G 3/30* | (2006.01) | |
| *H04R 3/04* | (2006.01) | |
| *H03F 3/45* | (2006.01) | |
| *A61B 5/00* | (2006.01) | |
| *H04R 1/46* | (2006.01) | |

(52) U.S. Cl.
CPC .............. *A61B 5/7257* (2013.01); *A61B 7/04* (2013.01); *H03G 3/30* (2013.01); *H04R 1/46* (2013.01); *H04R 3/04* (2013.01); *A61B 5/6823* (2013.01); *A61B 2562/0204* (2013.01); *A61B 2562/0219* (2013.01); *H03F 3/45* (2013.01); *H03F 2203/45151* (2013.01); *H03F 2203/45156* (2013.01)

(58) Field of Classification Search
CPC . A61B 5/6823; A61B 7/04; A61B 2562/0204; A61B 2562/0219; H03G 3/30; H04R 1/46; H04R 3/04; H03F 3/45; H03F 2203/45151; H03F 2203/45156
See application file for complete search history.

(56) References Cited

U.S. PATENT DOCUMENTS

| | | | |
|---|---|---|---|
| 9,176,141 B2 | 11/2015 | Al-Ali et al. | |
| 9,492,105 B1 | 11/2016 | Kayyali et al. | |
| 11,045,144 B2 | 6/2021 | Zhou et al. | |
| 2004/0105556 A1* | 6/2004 | Grove | A61B 7/04 381/67 |
| 2005/0010254 A1* | 1/2005 | Zhang | A61B 5/318 607/9 |
| 2005/0288571 A1 | 12/2005 | Perkins et al. | |
| 2006/0064037 A1* | 3/2006 | Shalon | A61B 5/0031 128/903 |
| 2008/0058652 A1 | 3/2008 | Payne | |
| 2008/0058872 A1 | 3/2008 | Brockway et al. | |
| 2008/0114266 A1 | 5/2008 | Shen et al. | |
| 2008/0154144 A1 | 6/2008 | Unver et al. | |
| 2011/0295127 A1 | 12/2011 | Sandler et al. | |
| 2012/0172676 A1* | 7/2012 | Penders | A61B 7/04 600/301 |
| 2012/0289849 A1 | 11/2012 | Kumar et al. | |
| 2013/0150754 A1* | 6/2013 | Rogers | A61B 7/04 600/586 |
| 2016/0100817 A1 | 4/2016 | Hussain | |
| 2016/0277860 A1 | 9/2016 | Vesa et al. | |
| 2016/0286312 A1* | 9/2016 | Devillez | G06F 3/165 |
| 2016/0287207 A1 | 10/2016 | Xue | |
| 2016/0310108 A1 | 10/2016 | Flynn | |
| 2017/0079594 A1 | 3/2017 | Telfort et al. | |
| 2018/0184918 A1 | 7/2018 | Kline et al. | |
| 2019/0000413 A1 | 1/2019 | Adler et al. | |
| 2019/0083038 A1 | 3/2019 | Griffin et al. | |
| 2019/0117162 A1 | 4/2019 | Zhou et al. | |
| 2019/0117165 A1 | 4/2019 | Zeng et al. | |
| 2020/0245889 A1 | 8/2020 | Telenkov et al. | |
| 2021/0321947 A1 | 10/2021 | Zhou et al. | |

FOREIGN PATENT DOCUMENTS

| | | | |
|---|---|---|---|
| CN | 204410807 U | 6/2015 | |
| WO | 2016033521 A9 | 3/2016 | |
| WO | WO-2016033521 A1 * | 3/2016 | ........... A61B 5/0006 |
| WO | 2019060455 A1 | 3/2019 | |
| WO | 2019071050 A2 | 4/2019 | |
| WO | 2019079785 A2 | 4/2019 | |

OTHER PUBLICATIONS

Cirrus Logic, "CS5368 114 dB, 192 KHz, 8-Channel A/D Converter," DS624F5, 2014, 42 pp.
Texas Instruments, "INA188 Precision, Zero-Drift, Rail-to-Rail Out, High-Voltage Instrumentation Amplifier," SB0S632, Sep. 2015, 40 pp.
Texas Instruments, "ADS1299-x Low-Noise 5-, 6-, 8-Channel, 24-Bit, Analog-to-Digital Converter for EEG and Biopotential Measurements," SBAS499C, Jul. 2012, Revised Jan. 2017, 81 pp.
Analog Devices, "ADA4522 55 V, Emi Enhanced, Zero Drift, Ultralow Noise, Rail-to-Rail Output Operational Amplifiers," D13168-0-9/17(F), 2017, 33 pp.
European Patent Office International Search Report and Written Opinion of International Searching Authority in International Application No. PCT/US2018/056832, dated May 6, 2019, 17 pp.
USPTO Office Action in U.S. Appl. No. 17/360,634, dated May 9, 2023, including List of References Cited by Examiner, Search Information Including Classification, Databases and Other Search Related Notes; Index of Claims; Examiner's Search Strategy and Results; Bibliographic Data Sheet; and List of References Cited by Applicant and Considered by Examiner 32 pp.
USPTO Office Action in U.S. Appl. No. 17/345,128, Sep. 9, 2023, including List of References Cited by Examiner; Index of Claims; Search Information Including Classification, Databases and Other Search Related Notes; Examiner's Search Strategy and Results; and 6 Lists of References Cited by Applicant and Considered by Examiner, 92 pp.

\* cited by examiner

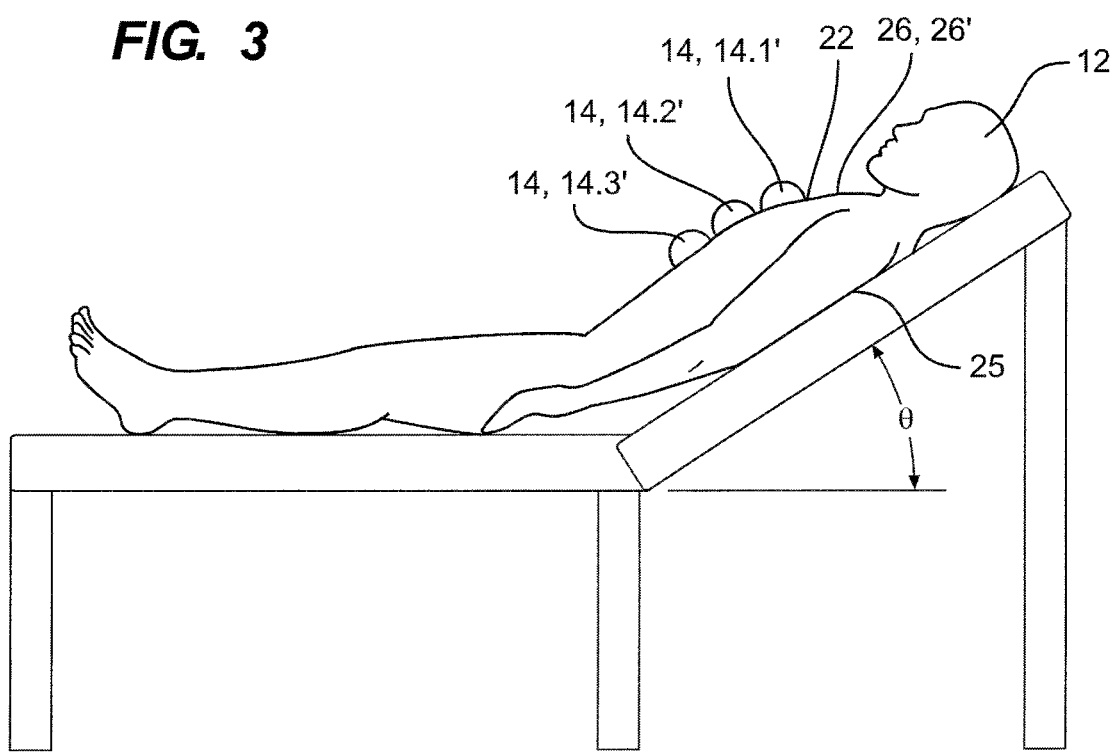

$2600$

Calculate Average Power At Each Test Frequency

$$\bar{P}_A = \frac{\sum_{k=0}^{N_{Frame}-1} P_A(k)}{N_{Frame}}$$

$$\bar{P}_B = \frac{\sum_{k=0}^{N_{Frame}-1} P_B(k)}{N_{Frame}}$$

$$\bar{P}_C = \frac{\sum_{k=0}^{N_{Frame}-1} P_C(k)}{N_{Frame}}$$

$$\bar{P}_D = \frac{\sum_{k=0}^{N_{Frame}-1} P_D(k)}{N_{Frame}}$$

— 2602

2604 — Any of $\{\bar{P}_A, \bar{P}_B, \bar{P}_C, \bar{P}_D\}$ > Threshold$_{GOOD}$ ? — Y

N

2606 — Each of $\{\bar{P}_A, \bar{P}_B, \bar{P}_C, \bar{P}_D\}$ > Threshold$_{BAD}$ ?

N

2610 — Test Failed

Y — 2608 — Test Passed

FIG. 26

CORONARY ARTERY DISEASE DETECTION SIGNAL PROCESSING SYSTEM AND METHOD

CROSS-REFERENCE TO RELATED APPLICATIONS

The instant application is a continuation of U.S. patent application Ser. No. 16/166,107 filed on 21 Oct. 2018, which claims the benefit of the U.S. Provisional Application Ser. No. 62/575,364 filed on 20 Oct. 2017, each of which is incorporated herein by reference in its entirety.

BRIEF DESCRIPTION OF THE DRAWINGS

In the accompanying drawings:

FIG. 2b illustrates a plurality of prospective locations of auscultatory sound-or-vibration sensors and ECG sensors on the thorax of the test subject illustrated in FIG. 2a;

FIG. 3 illustrates a test subject reclined on a surface, with their torso inclined while capturing auscultatory sound signals from a plurality of auscultatory sound-or-vibration sensors attached to the thorax of the test subject;

FIG. 25 illustrates frequency spectrum of the sensor-test acoustic-frequency waveform illustrated in FIG. 23a;

FIG. 26 illustrates a flow chart of a second phase of an auscultatory-sensor integrity-test procedure, which follows the first phase illustrated in FIG. 24;

DESCRIPTION OF EMBODIMENT(S)

Figure 1:
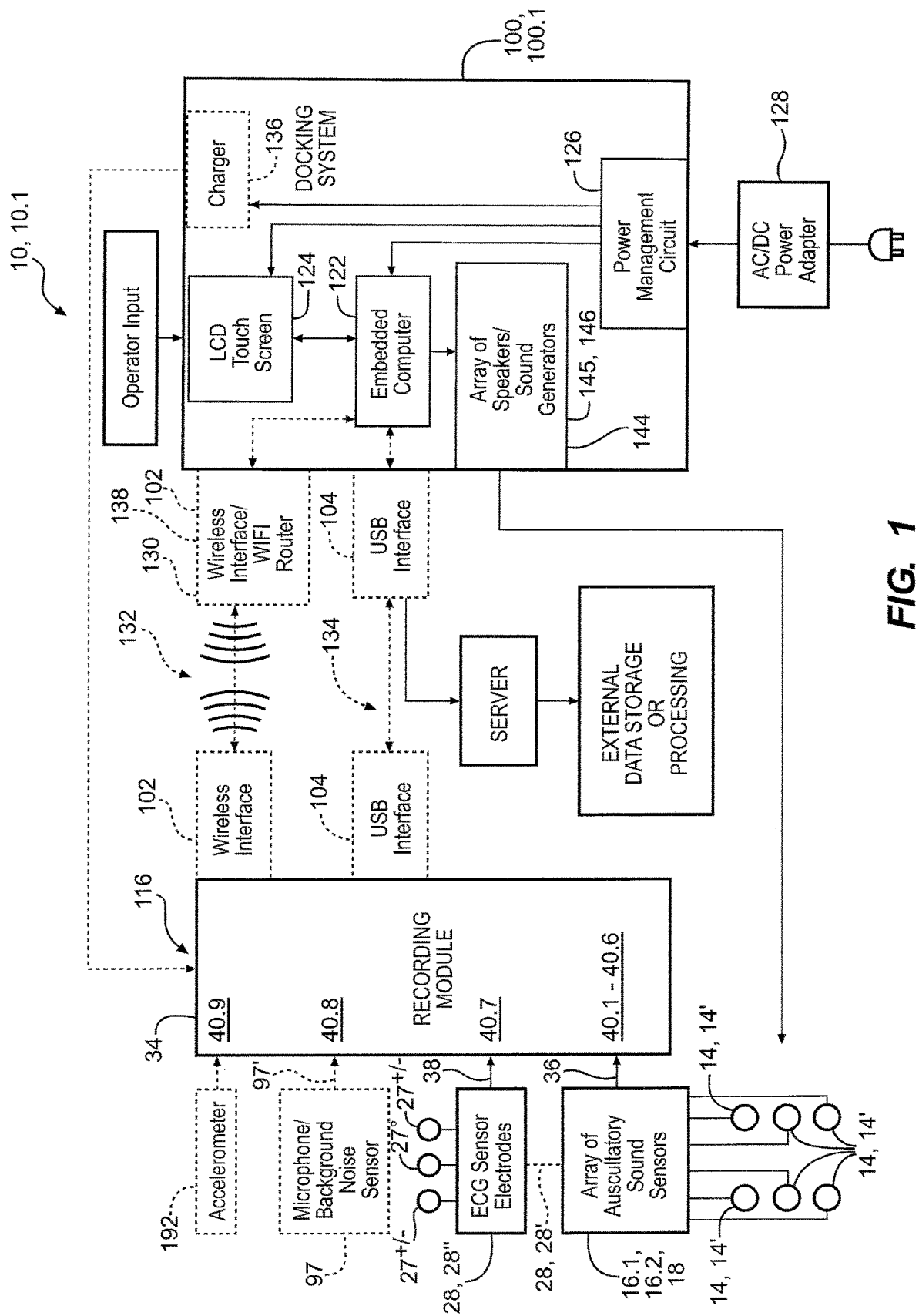
FIG. 1 illustrates a block diagram of a first aspect of a coronary artery disease detection system, incorporating a first aspect of an associated docking system.
Figure 2A:
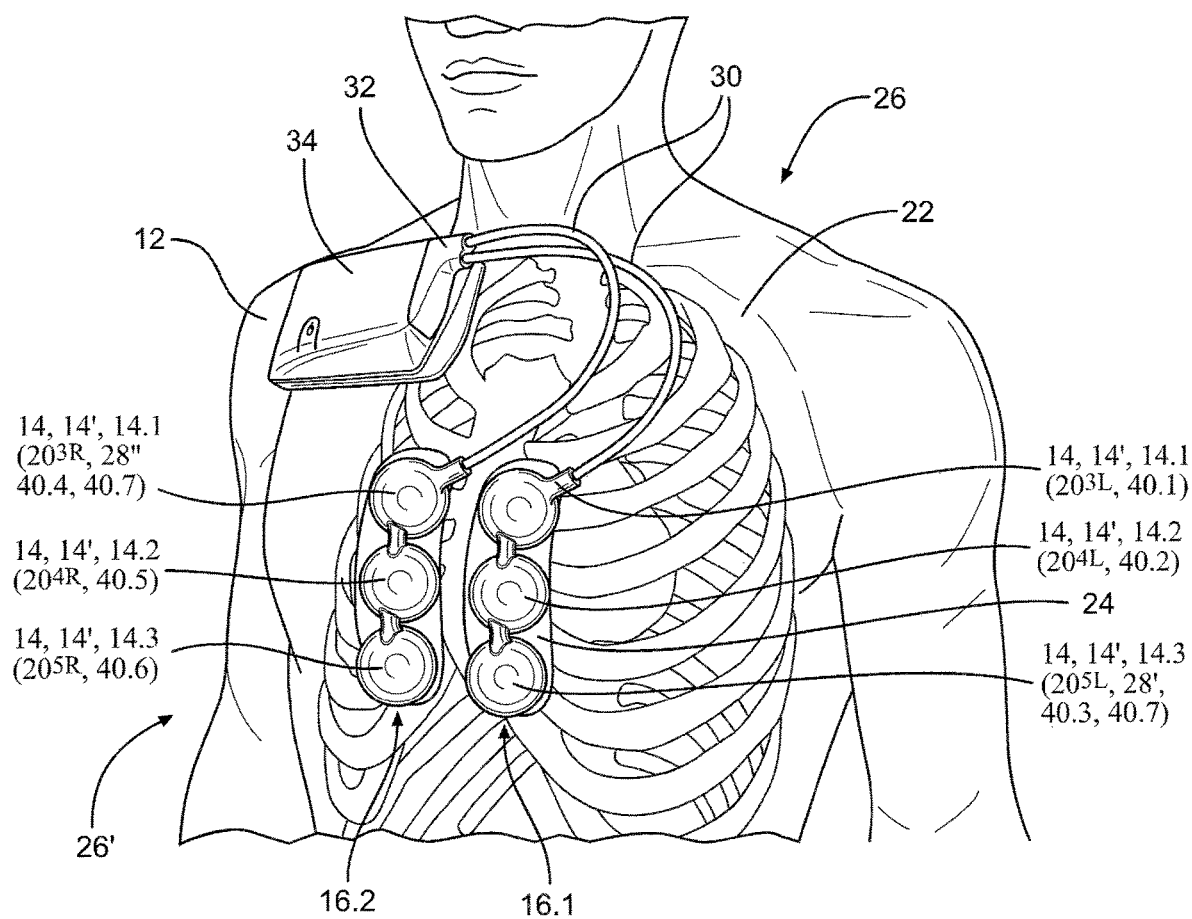
FIG. 2a illustrates a plurality of auscultatory sound-or-vibration sensors attached to the thorax of a test subject and operatively coupled to an associated recording module of the coronary-artery-disease detection system illustrated in FIG. 1, for gathering associated auscultatory sound signals used to diagnose cardiovascular health.
Figure 2B:
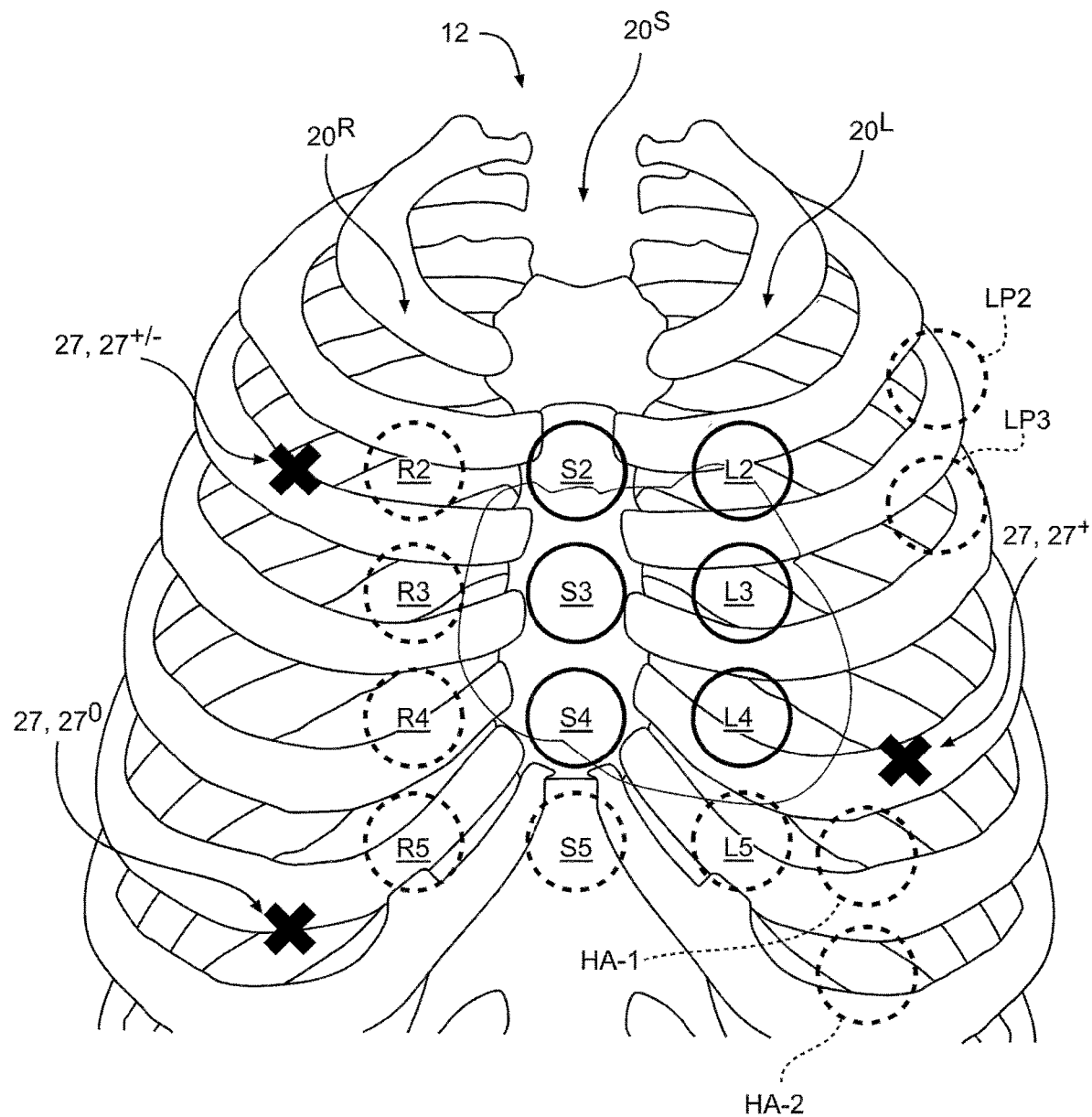

Referring to FIGS. 1 and 2a, a first aspect 10.1 of a coronary-artery-disease (CAD) detection system 10, 10.1 provides for detecting coronary artery disease of a test subject 12 from cardiovascular sounds or vibrations emitted from coronary arteries that become sufficiently obstructed so that the obstructions therein cause sound-emitting turbulence in the flow of blood therethrough. The cardiovascular sounds are sensed by one or more auscultatory sound-or-vibration sensors 14, for example, a pair of sensor assemblies 16.1, 16.2, each with three auscultatory sound-or-vibration sensors 14, 14.1, 14.2, 14.3, or, more generally, an array 18 of auscultatory sound-or-vibration sensors 14, either mechanically coupled to one another or mechanically isolated from one another. For example, in one set of embodiments, the auscultatory sound-or-vibration sensors 14 are located above and proximate to the third $20^{3L}$, $20^{3R}$, fourth $20^{4L}$, $20^{4R}$ and fifth $20^{5L}$, $20^{5R}$, intercostal spaces on the left and right side of the test subject 12, respectively, for the first 16.1 and second 16.2 sensor assemblies, respectively; or more generally, but not limited to, a set of three intercostal spaces1—for example, ranging from the second to the fifth—at two different lateral locations—for example, two of the left $20^L$, sternum $20^S$ and right $20^R$ lateral locations on the test subject 12, for example, as illustrated in FIG. 2b. For example, in accordance with a first aspect 14', each auscultatory sound-or-vibration sensor 14, 14' may be constructed and used as a passive device (i.e. not supplied with external power) in accordance with either U.S. Provisional Application No. 62/568,155 filed on 4 Oct. 2017, entitled AUSCULTATORY SOUND SENSOR, or U.S. patent application Ser. No. 14/152,004 filed on 4 Oct. 2018 entitled AUSCULTATORY SOUND-OR-VIBRATION SENSOR, each of which is incorporated herein by reference in its entirety, wherein each auscultatory sound-or-vibration sensor 14, 14' incorporates a metallic diaphragm disk incorporating a piezoelectric material bonded thereto and operatively coupled to a base rim of a housing provides for closing an open-ended cavity at a first end of the housing. In one aspect, plastic film adhesively bonded to at least one of an outer rim of the housing or an outer-facing surface of the disk provides for receiving an adhesive acoustic interface material to provide for coupling the housing to the skin of a test subject. In another aspect, an outer-facing surface of a base portion of the housing provides for receiving an adhesive acoustic interface material to provide for coupling the housing to the skin of a test subject, at least one inertial mass is operatively coupled to a central portion of the metallic diaphragm disk, and the opening in the first end of the housing is closed with a cover. Each auscultatory sound-or-vibration sensor 14, 14' is attached to the skin 22 of the test subject 12 with a layer of hydrogel material 24—or more generally, an adhesive acoustic-interface material 24'—that adhesively bonds the sensor to the skin 22 of the test subject 12, for example, so as to maintain the position of the auscultatory sound-or-vibration sensors 14, 14' on the thorax 26 of the test subject 12 when supported on a surface 25 that elevates the torso 26' of the test subject 12 at an inclination angle above horizontal—but generally, as close to upright (i.e. θ=90 degrees) as can be accommodated by an associated adhesive acoustic-interface material 24' of the associated auscultatory sound-or-vibration sensors 14, 14.1, 14.2, 14.3 that provides for attachment thereof to the skin 22 of the test subject 12—, for example, as illustrated in FIG. 3, at an angle of about 30 degrees above horizontal, which has been found to be beneficial for acquiring auscultatory sound signals associated with cardiovascular disease. The acoustic impedance of the hydrogel material 24—which is made primarily of water, having an acoustic impedance of $1.5 \times 10^6$ Kg/(m² *sec)—also provides for substantially matching the nominal $1.6 \times 10^6$ Kg/(m²*sec) acoustic impedance of the skin. The auscultatory sound-or-vibration sensor 14, 14' may be adapted to incorporate an electrode 27 of an ECG sensor 28, 28'—a pair or plurality of which can provide for acquiring an associated electrographic signal—or alternatively, the coronary-artery-disease (CAD) detection system 10, 10.1 may utilize a separate ECG sensor 28, 28", either of which may be used to facilitate synchronization with the associated heart cycles. Generally, either style of ECG sensor 28, 28', 28" incorporates a plurality of electrodes 27, for example, in one set of embodiments, a pair of signal electrodes 27, $27^{+/-}$ in cooperation with a ground electrode $27^0$, wherein, referring to FIG. 2a, the signal electrodes 27, 27$^{+/-}$ span the heart from diametrically-opposed quadrants of the torso 26', and the ground electrode 27$^0$ is located in a different quadrant, orthogonally displaced from a midpoint of a baseline connecting the signal electrodes 27, 27$^{+/-}$.

As used herein, the terms "auscultatory sound" and "auscultatory sound or vibration" are each intended to mean a sound or vibration originating from inside a human or animal organism as a result of the biological functioning thereof, for example, as might be generated by action of the heart, lungs, other organs, or the associated vascular system; and is not intended to be limited to a particular range of frequencies—for example, not limited to a range of frequencies or sound/vibration intensities that would be audible to a human ear,—but could include frequencies above, below, and in the audible range, and sound/vibration intensities that are too faint to be audible to a human ear. Furthermore, the terms "auscultatory-sound sensor" and "auscultatory sound-or-vibration sensor" are each intended to mean a sound or vibration sensor that provides for transducing auscultatory sounds or vibrations into a corresponding electrical or optical signal that can be subsequently processed, and is not limited to a particular mode of transduction.

The auscultatory sound-or-vibration sensors 14, 14' are operatively coupled—for example, by one or more cables or cable assemblies 30 between the auscultatory sound-or-vibration sensors 14, 14' and a magnetically-secured electrical connector 32—to a recording module 34 that provides for preprocessing, and in some embodiments, locally storing, the auscultatory sound signals 36 that are transduced by the one or more auscultatory sound-or-vibration sensors 14, 14'. In some embodiments, the recording module 34 also provides for preprocessing, and in some embodiments, locally storing, an electrographic signal 38 generated by an associated ECG sensor 28, 28', 28". The magnetically-secured electrical connector 32 is removably attached to the recording module 34 by a magnetic attraction therebetween, with associated permanent magnets incorporated in one or both of the magnetically-secured electrical connector 32 or the recording module 34.

Figure 4:
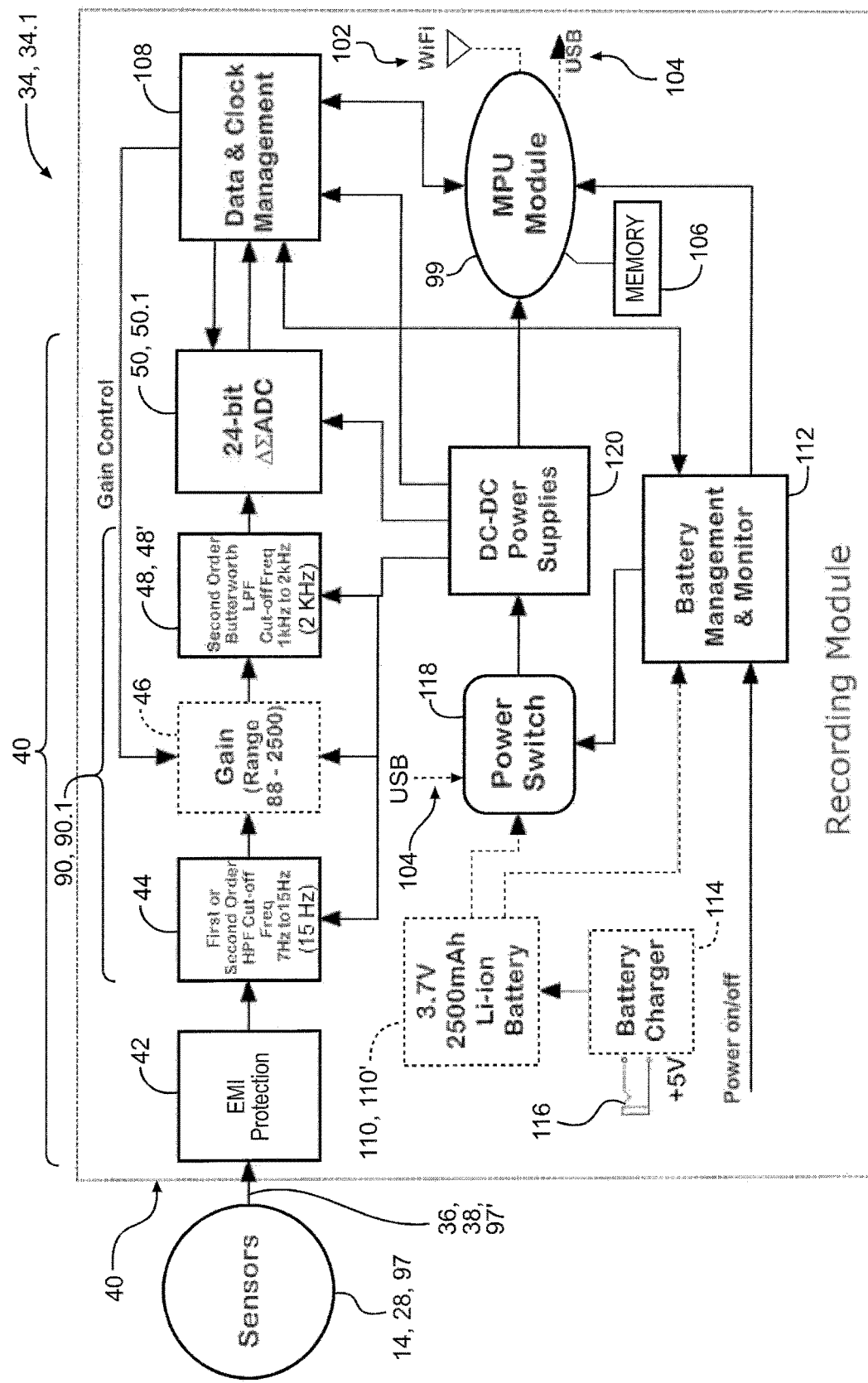
FIG. 4 illustrates a block diagram of a first aspect of a recording module of the coronary-artery-disease detection system illustrated in FIG. 1.

Referring also to FIG. 4, in accordance with a first aspect 34.1 of a recording module 34, 34.1, each auscultatory sound signal 36 from each auscultatory sound-or-vibration sensor 14, 14', and the electrographic signal 38 if acquired, are preprocessed by a separate signal preprocessing channel 40, 40.1, 40.2, 40.3, 40.4, 40.5, 40.6, 40.7—respectively for the auscultatory sound signals 36 and the electrographic signal 38, respectively—that comprises an EMI protection circuit 42, a high-pass filter 44, an optional controllable gain amplifier 46, a low-pass filter 48—for example, a second order Butterworth fully-differential low-pass filter 48, 48'—and an analog-to-digital converter 50. For example, the high-pass filter 44 may be of either first or second order, with a cut-off frequency in the range of 3 to 15 Hz, for example, about 15 Hz for one set of embodiments. In one set of embodiments, the gain of the controllable gain amplifier 46 is controllable in 16 levels between about 88 and about 2500. Furthermore, in one set of embodiments, the low-pass filter 48 is a second-order Butterworth filter with a cut-off frequency in the range of 1 kHz to 2.5 kHz, for example, about 2 kHz.

Figure 5A:
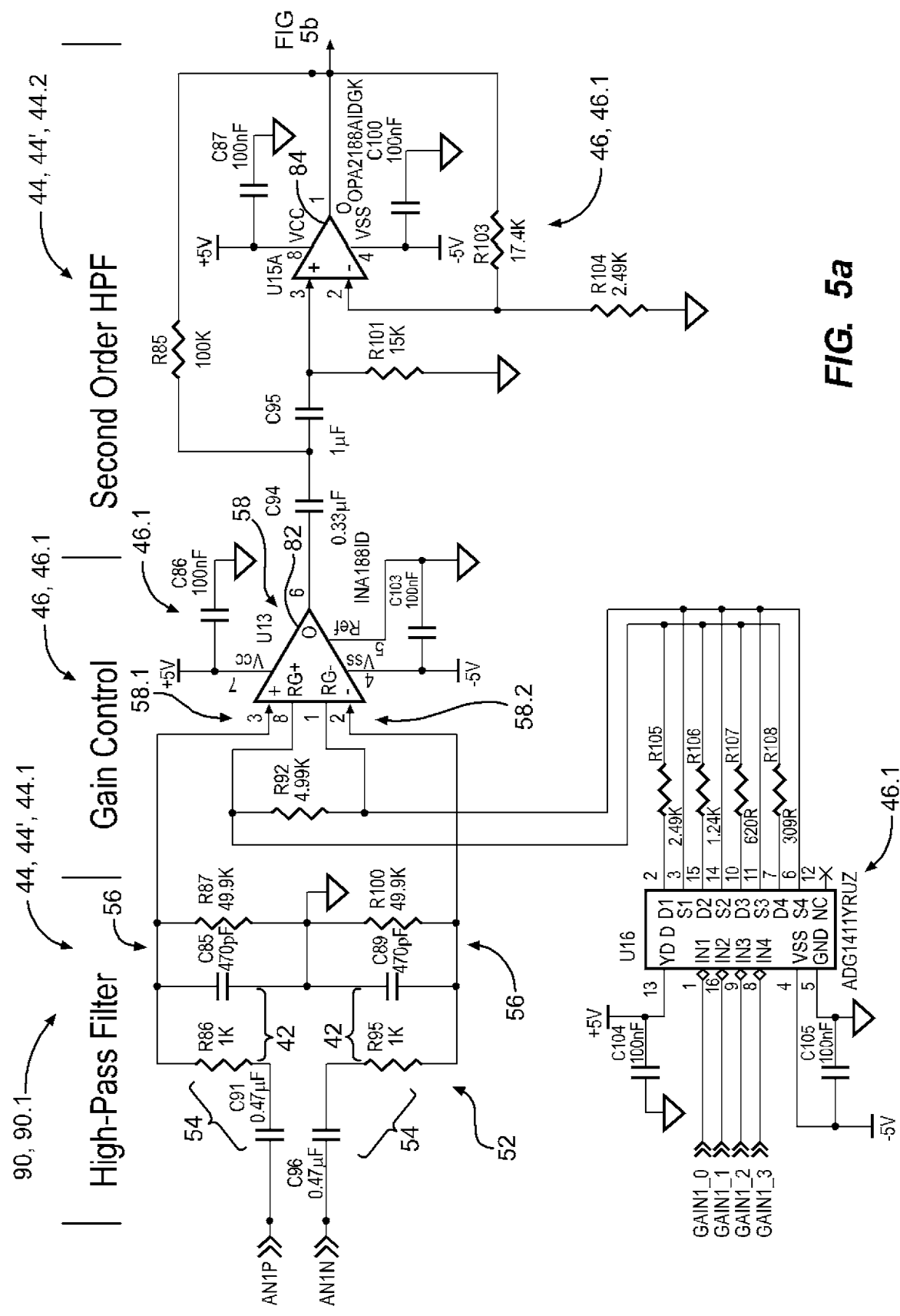
FIG. 5a illustrates a schematic diagram of a first portion of a first embodiment of a signal preprocessing channel of the first aspect of the recording module illustrated in FIG. 4, including a high-pass filter, and controllable-gain amplifier.

For example, referring to FIG. 5a, a first embodiment the high-pass filter 44, 44' comprises first 44.1 and second 44.2 high-pass filters that span a controllable gain amplifier 46, wherein the first high-pass filter 44.1 comprises a R-C high pass filter, for which the associated cut-off frequency fc1 is given by:

$$fc1 = \frac{1}{2\pi \cdot R87 \cdot C91}, \quad (1)$$

and the second high-pass filter 44.2 comprises a second order Butterworth Sallen-Key filter, for which the associated cut-off frequency fc2 is given by:

$$fc2 = \frac{1}{2\pi \cdot \sqrt{R101 \cdot R85 \cdot C94 \cdot C95}}. \quad (2)$$

The first high-pass filter 44.1 incorporates a balanced, differential input 52, each leg of which comprises a series, first R-C network 54 feeding a parallel, second RC network 56, the latter of which is in parallel with corresponding non-inverting 58.1 and inverting 58.2 inputs of an associated instrumentation amplifier 58 of the associated, below-described, first embodiment of the controllable gain amplifier 46, 46.1. The associated EMI protection circuit 42 comprises R-C network R86-C85.

Figure 6A:
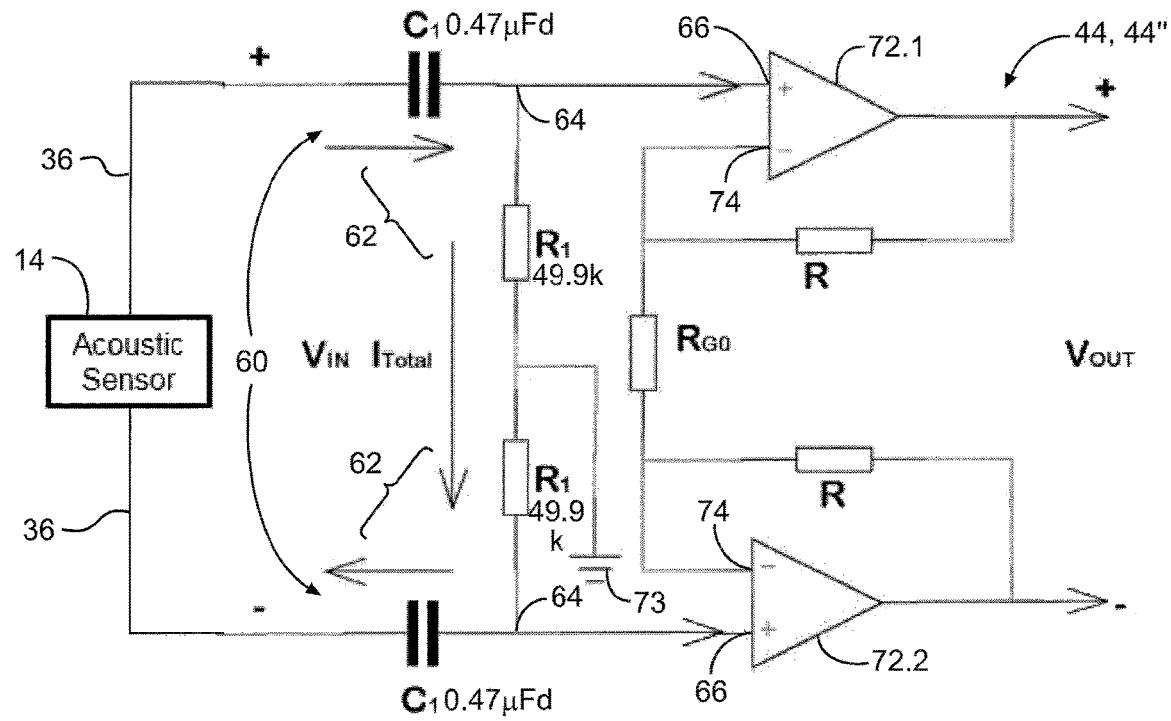
FIG. 6a illustrates a schematic diagram of a second embodiment of a high-pass filter of the first aspect of the recording module illustrated in FIG. 4, without a shielding ground, used with an auscultatory sound-or-vibration sensor.

Referring to FIG. 6a, a second embodiment of the high-pass filter 44, 44" has a balanced, differential input 60, each leg of which has the same impedance with respect to ground and is connected across a corresponding series R-C network 62 for which the corresponding differential input 60 thereto is applied to the associated capacitor C1. The junction 64 between the capacitor C1 and the resistor R1 of the series R-C network 62 is connected to a corresponding non-inverting input 66 of an associated corresponding operational amplifier 68.1, 68.2, and the remaining terminal of the resistor 68 is connected to ground 73. Each of the inverting inputs 74 of the operational amplifiers 72.1, 72.2 are interconnected through a resister RG0, and also connected to a feedback resistor R. When used to preprocess an auscultatory sound signal 36 from an auscultatory sound-or-vibration sensor 14, 14', the auscultatory sound signal 36 exclusively drives the balanced, differential input 60 of the high-pass filter 44, 44".

A differential measurement system—such as the high-pass filter 44, 44" illustrated in FIG. 6a—provides for rejecting a common-mode signal if the two-terminal source, the two-terminal source receiver, and the associated pair of conductors of the cable interconnecting the source and receiver, are each balanced, wherein each of the source and receiver are balanced if each of the source terminals has the same impedance to ground, each of the receiver terminals has the same impedance to ground, and each of the pair of conductors of the cable has the same impedance to ground.

Figure 6B:
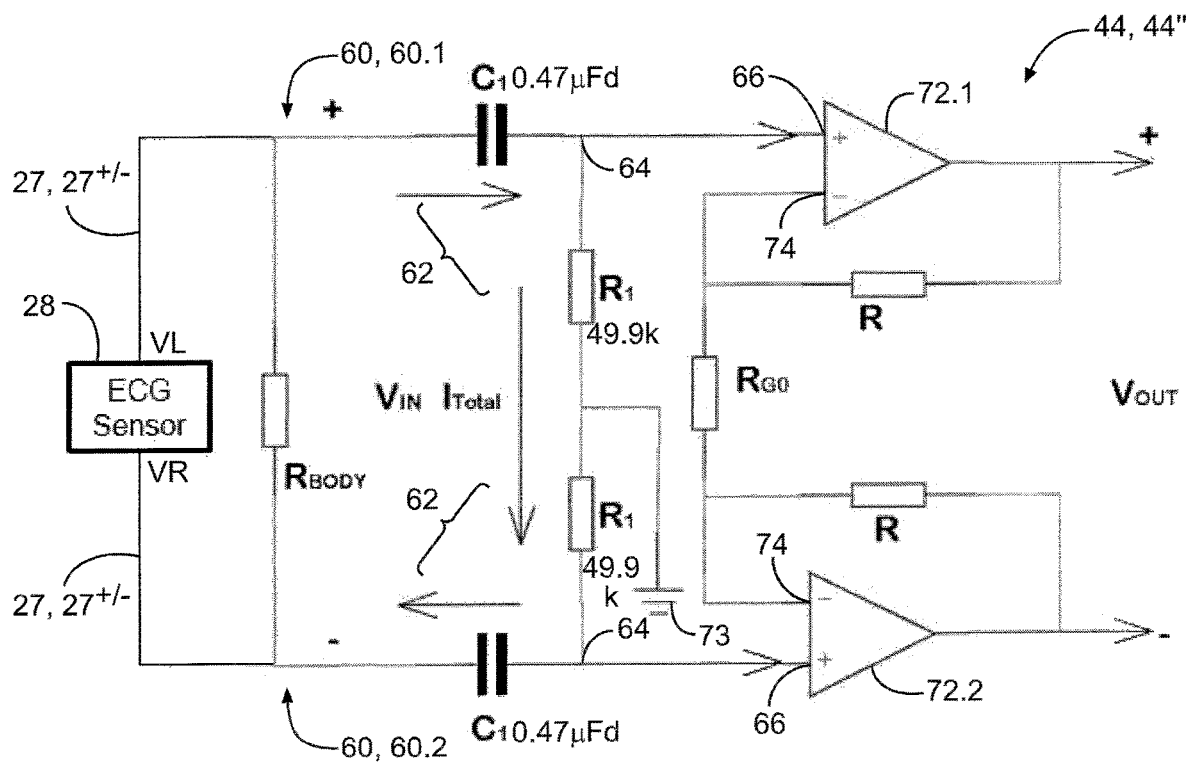
FIG. 6b illustrates a schematic diagram of the second embodiment of the high-pass filter of the first aspect of the recording module illustrated in FIG. 4, without the shielding ground, but used with an ECG sensor.

However, for the high-pass filter 44, 44" illustrated in FIG. 6b, when used to preprocess an electrographic signal 38 from an ECG sensor 28, 28', 28", the electrographicsignal 38 applied to the differential input 60 is shunted by a resistance $R_{BODY}$ of the body, so that the associated electrographic signal 38—across the equivalent resistance $R_{BODY}$ shunting the output from the electrographic sensor 28—effectively acts as a single-ended signal, so as to provide for electronic noise on the different terminals of the high-pass filter 44, 44" to be different, and therefore not be completely rejected by the associated differential measurement system of the high-pass filter 44, 44". For example, when an auscultatory sound-or-vibration sensor 14, 14'or an ECG sensor 28, 28', 28" is attached to the skin 22 of a test subject 12, some conductive noise—for example, 60 Hz power line noise—may become superimposed on a differential analog input that does not have a shielding ground. The shielding ground is a reference point for the right and left ECG inputs which are balanced. Otherwise, there would be no reference, so the 2-wires ECG input would act like a single ended source.

Figure 7A:
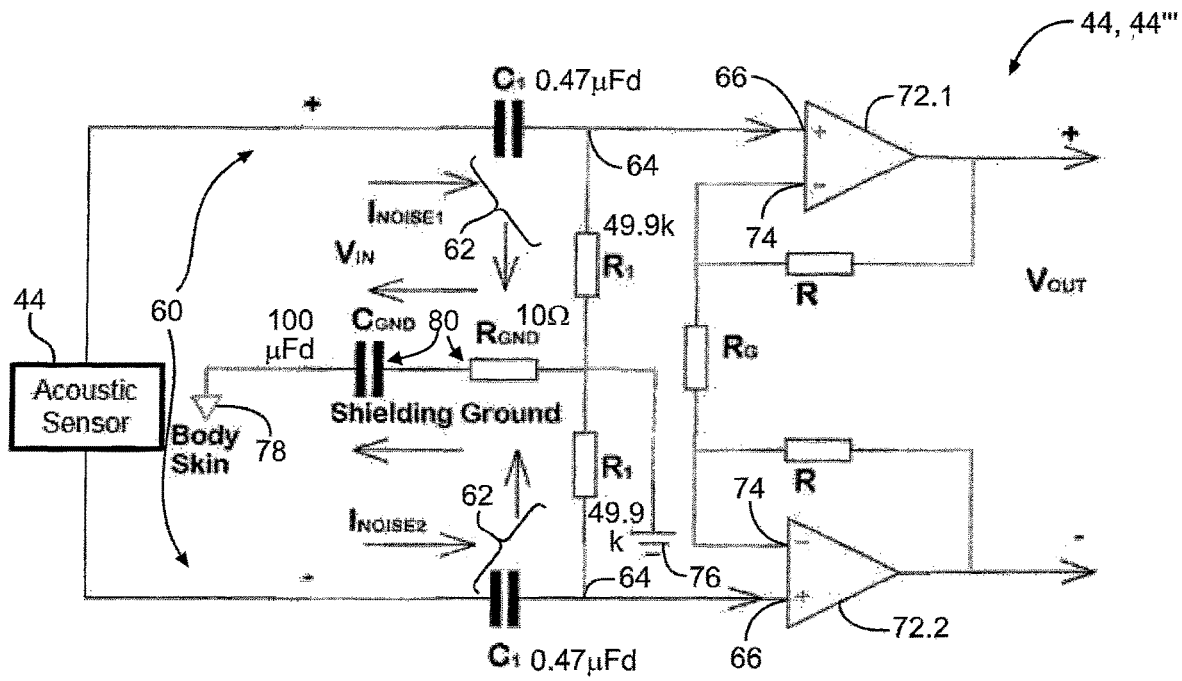
FIG. 7a illustrates a schematic diagram of a third embodiment of the high-pass filter of the first aspect of the recording module illustrated in FIG. 4, with a shielding ground, used with an acoustic sensor.
Figure 7B:
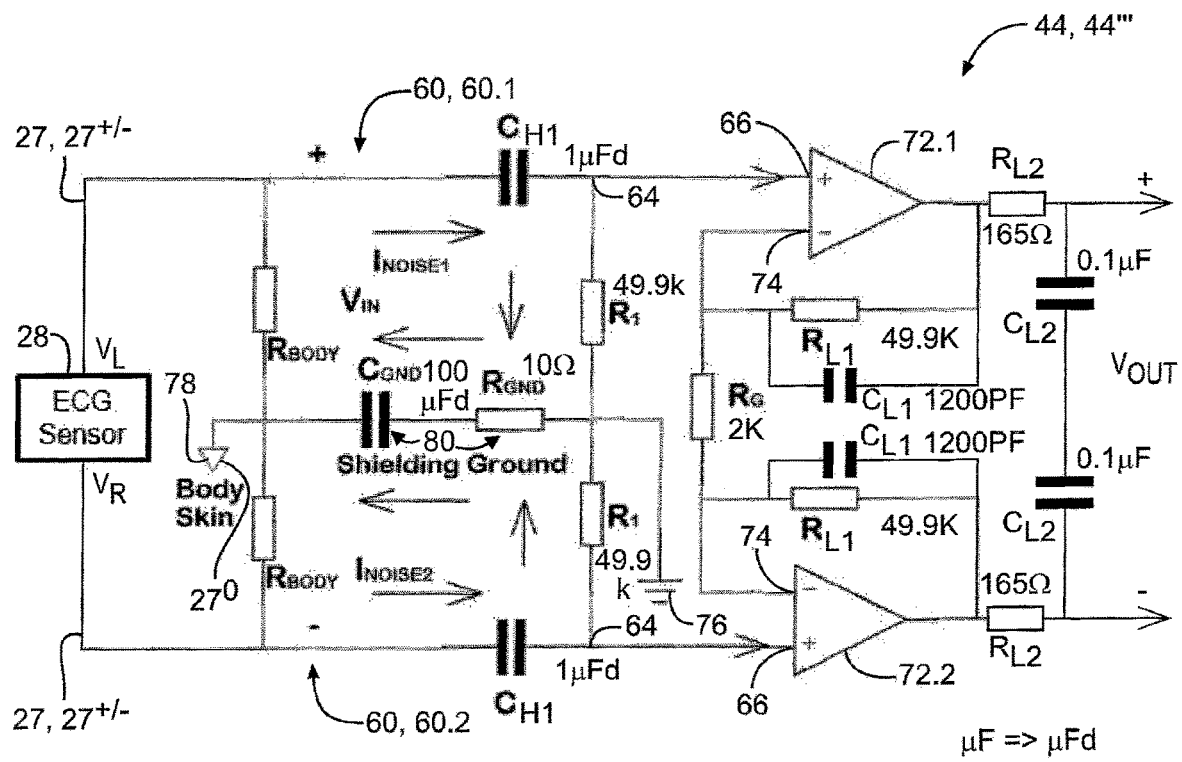
FIG. 7b illustrates a schematic diagram of the third embodiment of the high-pass filter of the first aspect of the recording module illustrated in FIG. 4, with the shielding ground, used with an ECG sensor.

Referring to FIGS. 7a and 7b, in a third embodiment of the high-pass filter 44, 44''', that provides for a balanced, differential input 60—for either input from an auscultatory sound-or-vibration sensor 14, 14' as illustrated in FIG. 7a, or an input from an ECG sensor 28, 28', 28'' as illustrated in FIG. 7b—by coupling the circuit ground 76 to a body shielding ground 78 (i.e. the skin 22 of the test subject 12) through a series R-C circuit 80 comprising resistor $R_{GND}$ in series with capacitor $C_{GND}$, the common-mode component of noise signal components $I_{NOISE1}$ and $I_{NOISE2}$ contaminating the first 60.1 and second 60.2 input terminals of the high-pass filter 44, 44'''will be rejected by the associated differential measurement system of the high-pass filter 44, 44''', and remaining unbalanced components of noise with be shorted to body shielding ground 78 through the series R-C circuit 80.

Accordingly, in one set of embodiments, the second embodiment of the high-pass filter 44, 44'' is used for receiving and filtering a corresponding auscultatory sound signal 36 from a corresponding auscultatory sound-or-vibration sensor 14, 14', and the third embodiment of the high-pass filter 44, 44''' is used for receiving and filtering a corresponding electrographic signal 38 from the ECG sensor 28, 28', 28''. The body shielding ground 78 can be located anywhere on the skin 22 of the test subject 12. In one set of embodiments, the connection of the body shielding ground 78 is made via a conductive plate on the bottom side of the recording module 34, 34.1 that rests upon the skin 22 of the test subject 12 during the test. When measuring electrographic signals 38 from the ECG sensor 28, 28', 28'', the body shielding ground 78 may be provided by an associated ground electrode $27^0$ of the ECG sensor 28, 28', 28''.

Figure 8:
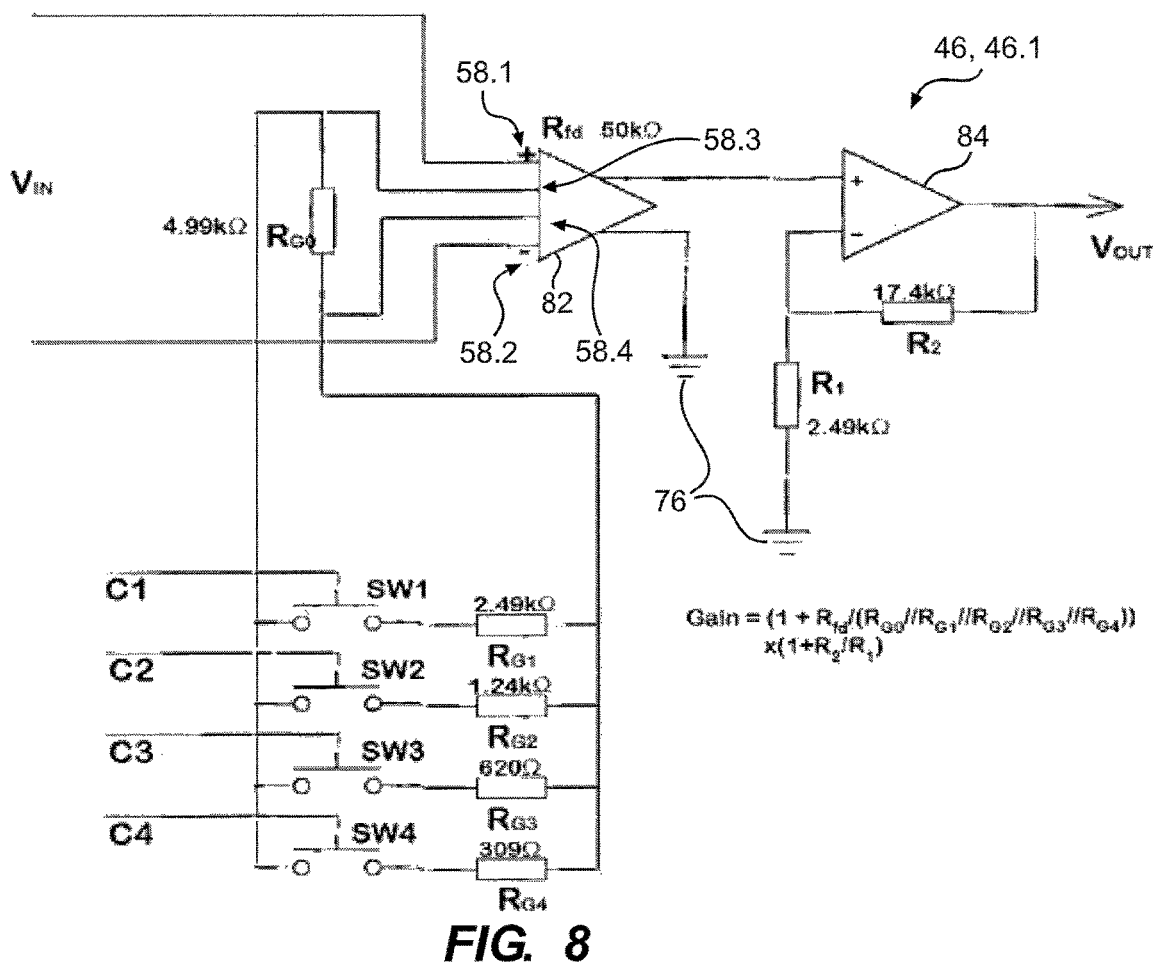
FIG. 8 illustrates a second schematic diagram of the first embodiment of the controllable-gain amplifier of the first aspect of the recording module illustrated in FIG. 4.
Figure 9:
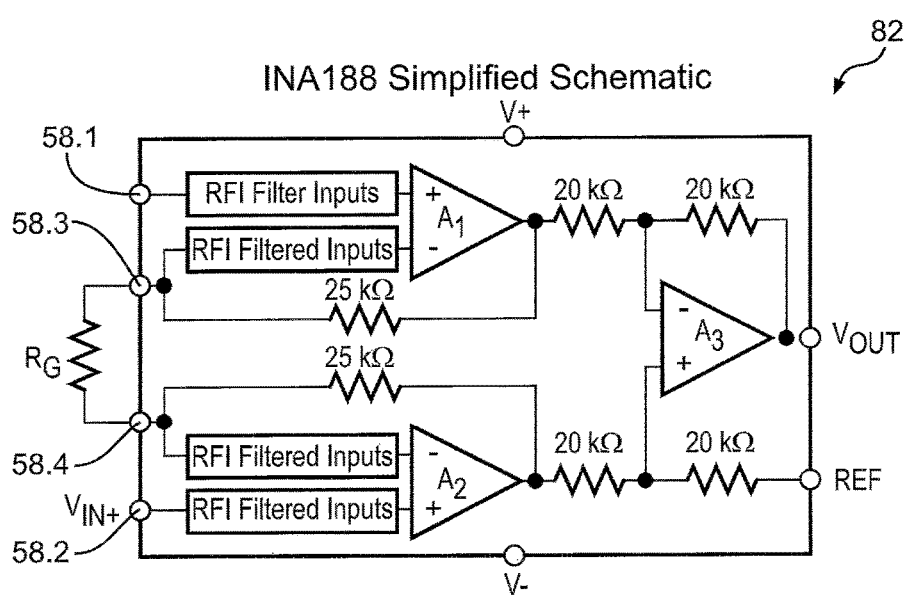
FIG. 9 illustrates a schematic diagram of an instrumentation amplifier used in the controllable-gain amplifier illustrated in FIG. 8.

Referring again to FIG. 5a, and referring to FIG. 8, a first embodiment 46.1 of a controllable gain amplifier 46, 46.1 comprises a differential-input instrumentation amplifier 82, for example, Texas Instruments 1NA188, a simplified schematic diagram of which is illustrated in FIG. 9, and which is described in Texas Instruments, "1NA188 Precision, Zero-Drift, Rail-to-Rail Out, High-Voltage Instrumentation Amplifier," SB0S632, September 2015, 40 pages, which is incorporated herein by reference in its entirety. The non-inverting 58.1 and inverting 58.2 inputs of the differential-input instrumentation amplifier 82 are operatively coupled to the output of the first high-pass filter 44.1, and a single-ended output of the differential-input instrumentation amplifier 82 is operatively to a fixed-gain second operational amplifier 84, the latter of which is shared with the second high-pass filter 44.2. The 1NA188 differential-input instrumentation amplifier 82 has an effective amplification feedback resistance $R_{fd}$ =50 kΩ, and the overall gain of the 1NA188 differential-input instrumentation amplifier 82 given by:

$$G = 1 + \frac{R_{fd}}{R_G}. \quad (3)$$

wherein $R_G$ is the effective resistance across the remaining two input terminals 58.3, 58.4 of the 1NA188 differential-input instrumentation amplifier 82. The controllable gain amplifier 46, 46.1 further comprises a fixed resister $R_{G0}$ across input terminals 58.3, 58.4 of the 1NA188 differential-input instrumentation amplifier 82, and further comprises an array of N=4 selectable resistors $R_{G1}$, $R_{G2}$, $R_{G3}$, $R_{G4}$, each of which is in series with a corresponding respective controllable analog switch SW1, SW2, SW3, SW4 under control of a corresponding, respective logic bit control signal C1, C2, C3, C4, wherein each series combination is in parallel with the fixed resister $R_{G0}$ across input terminals 58.3, 58.4 of the 1NA188 differential-input instrumentation amplifier 82. The resistance of each of the controllable analog switches SW1, SW2, SW3, SW4 in the ON state is negligible in comparison with the corresponding resistances of the associated selectable resistors $R_{G1}$, $R_{G2}$, $R_{G3}$, $R_{G4}$. The N=4 logic bit control signals C1, C2, C3, C4 provide for 16 different possible combinations, with a corresponding effective resistance across the input terminals 58.3, 58.4 of the 1NA188 differential-input instrumentation amplifier 82 ranging in value between $R_{G0}$ and the parallel combination of all five resistors, i.e. $R_{G0}\|R_{G1}\|R_{G2}\|R_{G3}\|R_{G4}$. In general, for N selectable resisters, there would be $2^N$ different possible values of effective resistance $R_G$. The resulting total effective gain of the controllable gain amplifier 46, 46.1 is then given by:

$$\text{Gain} = \left(1 + \frac{R_{fd}}{(R_{G0}//R_{G1}//R_{G2}//R_{G3}//R_{G4})}\right) \times \left(1 + \frac{R_2}{R_1}\right). \quad (4)$$

wherein the symbol "‖R" means a parallel combination of that resistance with the remaining resistances if the corresponding controllable analog switch SW1, SW2, SW3, SW4 is activated, and means a parallel combination with an infinite resistance if the corresponding controllable analog switch SW1, SW2, SW3, SW4 is not activated.

Figure 10:
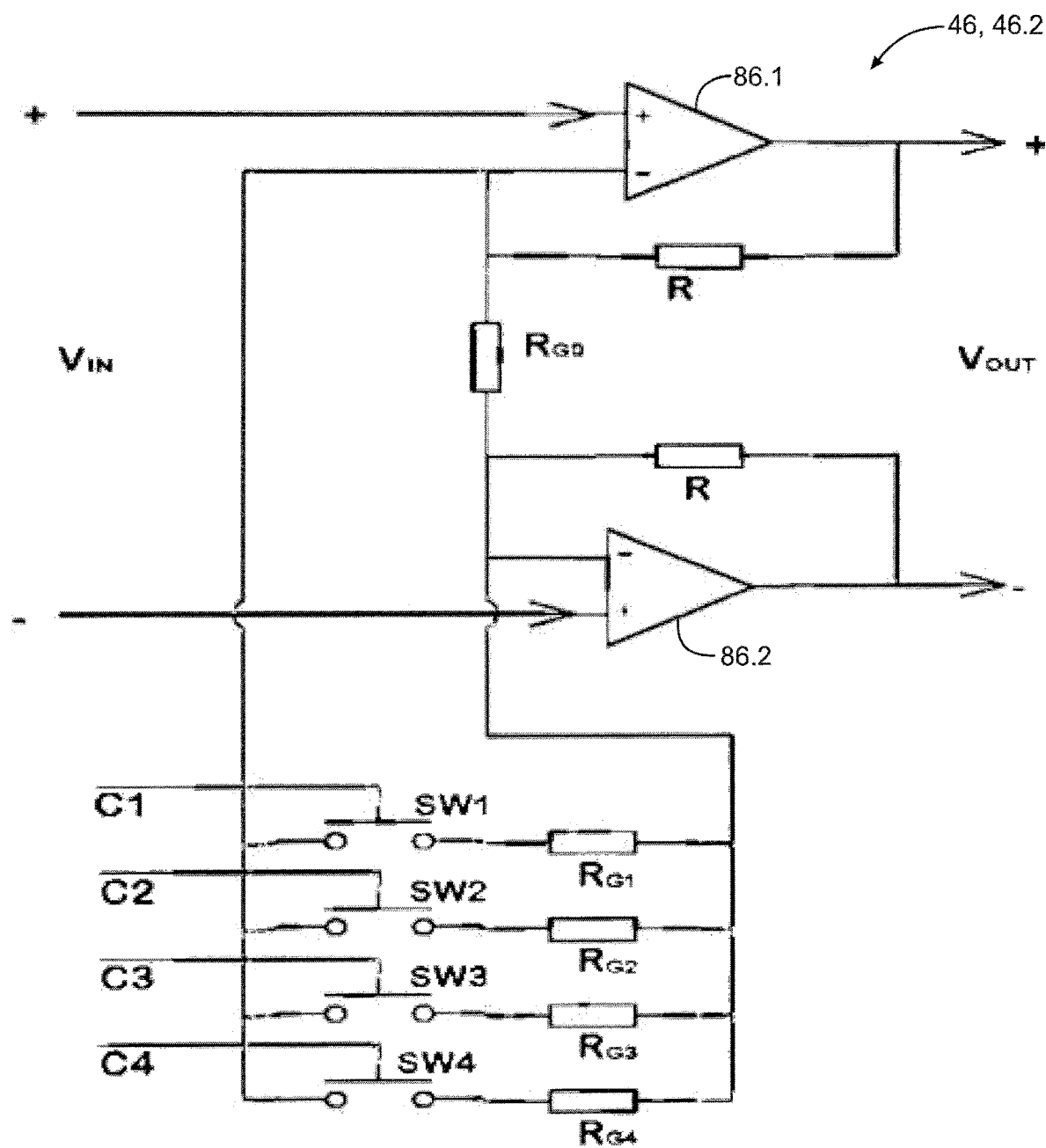
FIG. 10 illustrates a schematic diagram of a second embodiment of a controllable-gain amplifier of the first aspect of the recording module illustrated in FIG. 4.

Referring to FIG. 10, a second embodiment 46.2 of a controllable gain amplifier 46, 46.2 is similar to the above-described first embodiment 46.1, but with the 1NA188 differential-input instrumentation amplifier 82 replaced with corresponding first 86.1 and second 86.2 operational amplifiers interconnected as a differential amplifier, without the associated fixed gain second operational amplifier 84.

Figure 5B:
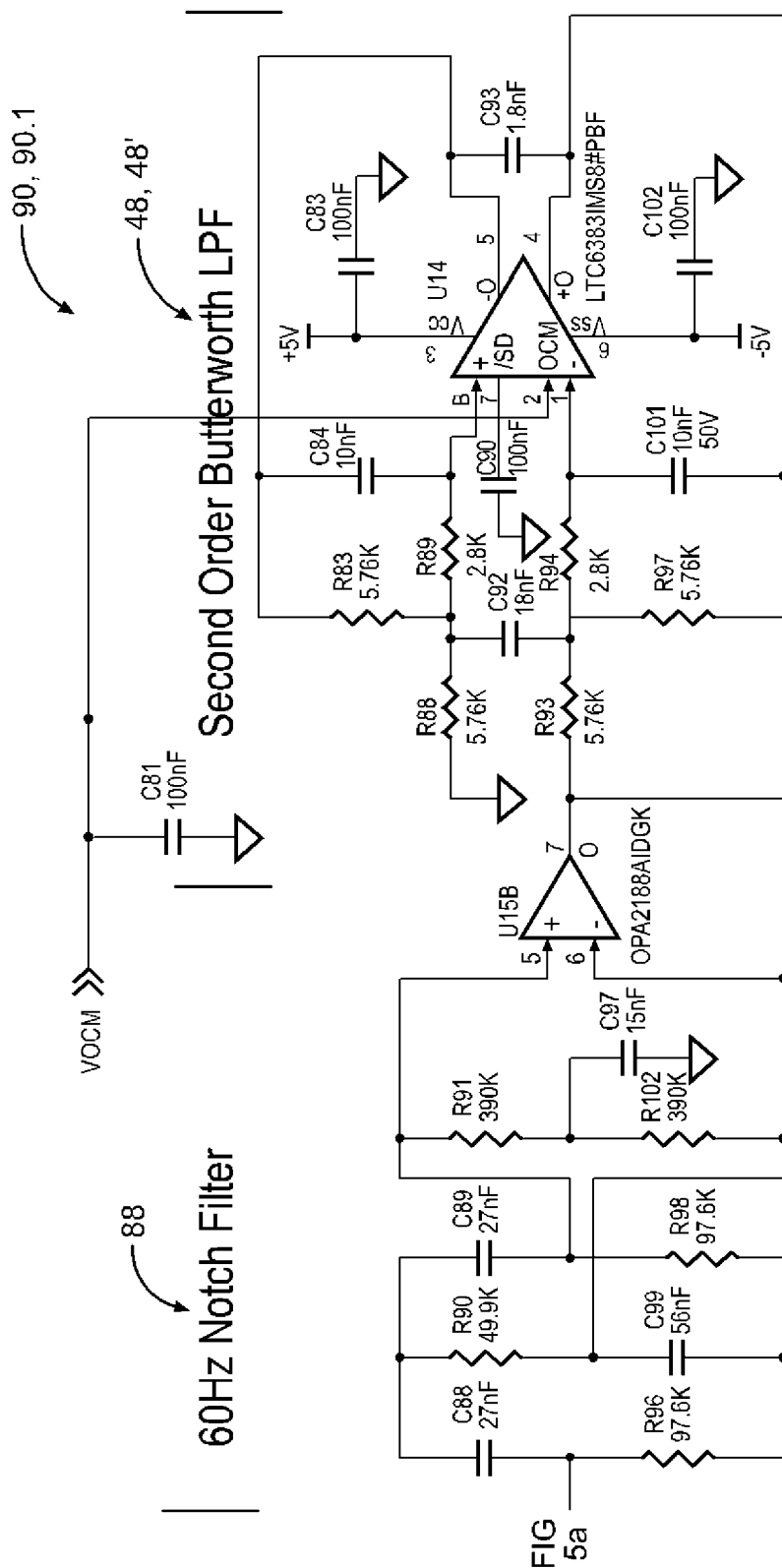
FIG. 5b illustrates a schematic diagram of a second portion of a first embodiment of the signal preprocessing channel of the first aspect of the recording module illustrated in FIG. 4, including a notch filter, and a low-pass filter.

Referring to FIG. 5b, the output of the controllable gain amplifier 46, 46.1 and the second high-pass filter 44.2 is then coupled to a 60 Hz notch filter 88 to remove AC power-associated noise, the output of which is coupled to the second order Butterworth fully-differential low-pass filter 48, 48', for which the cut-off frequency of the latter is given by:

$$fc = \frac{1}{2\pi \cdot \sqrt{2 \cdot R83 \cdot R89 \cdot C84 \cdot C92}}. \quad (5)$$

Figure 11:
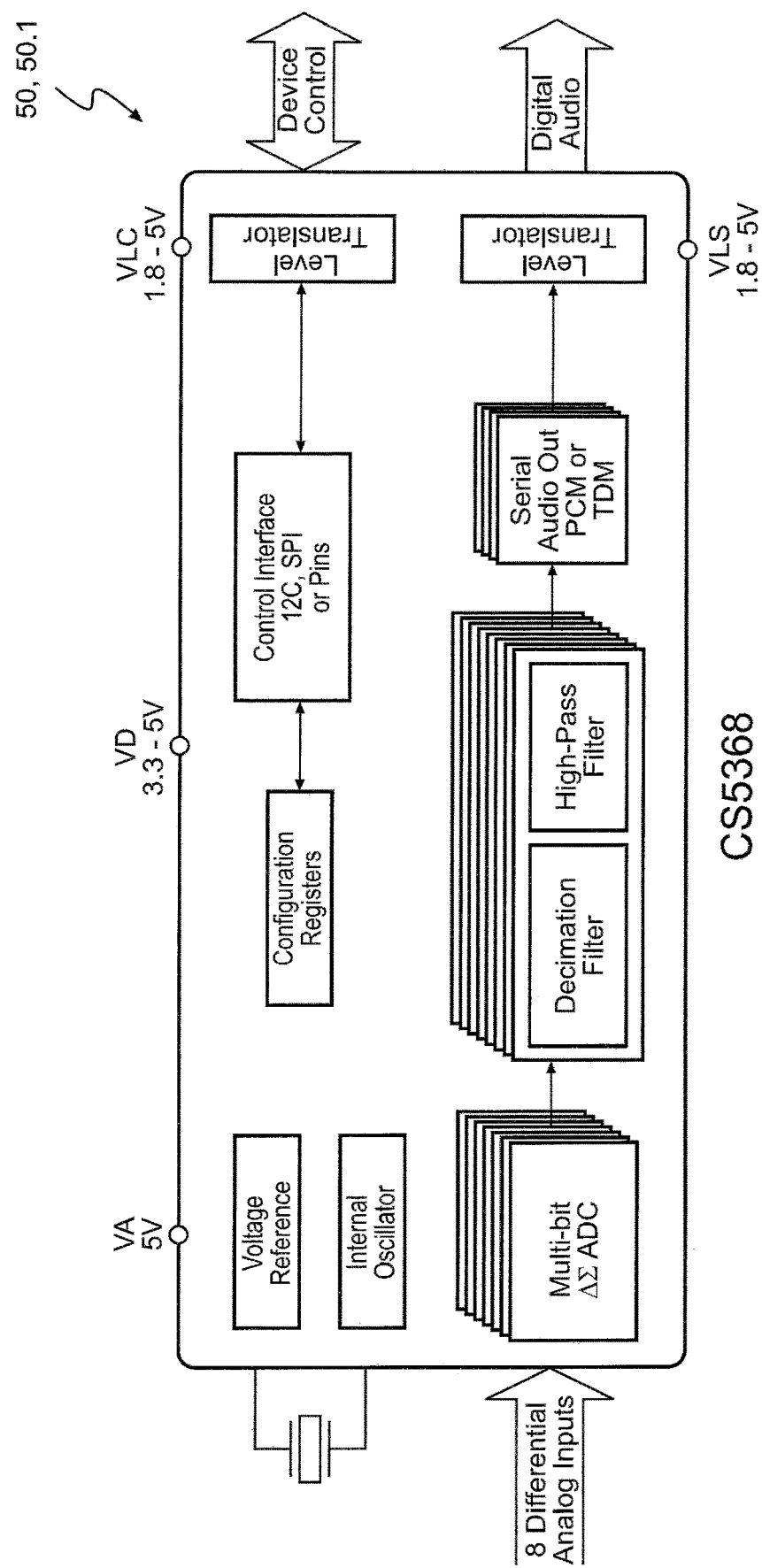
FIG. 11 illustrates a first block diagram of an analog-to-digital converter of the first aspect of the recording module illustrated in FIG. 4.
Figure 12:
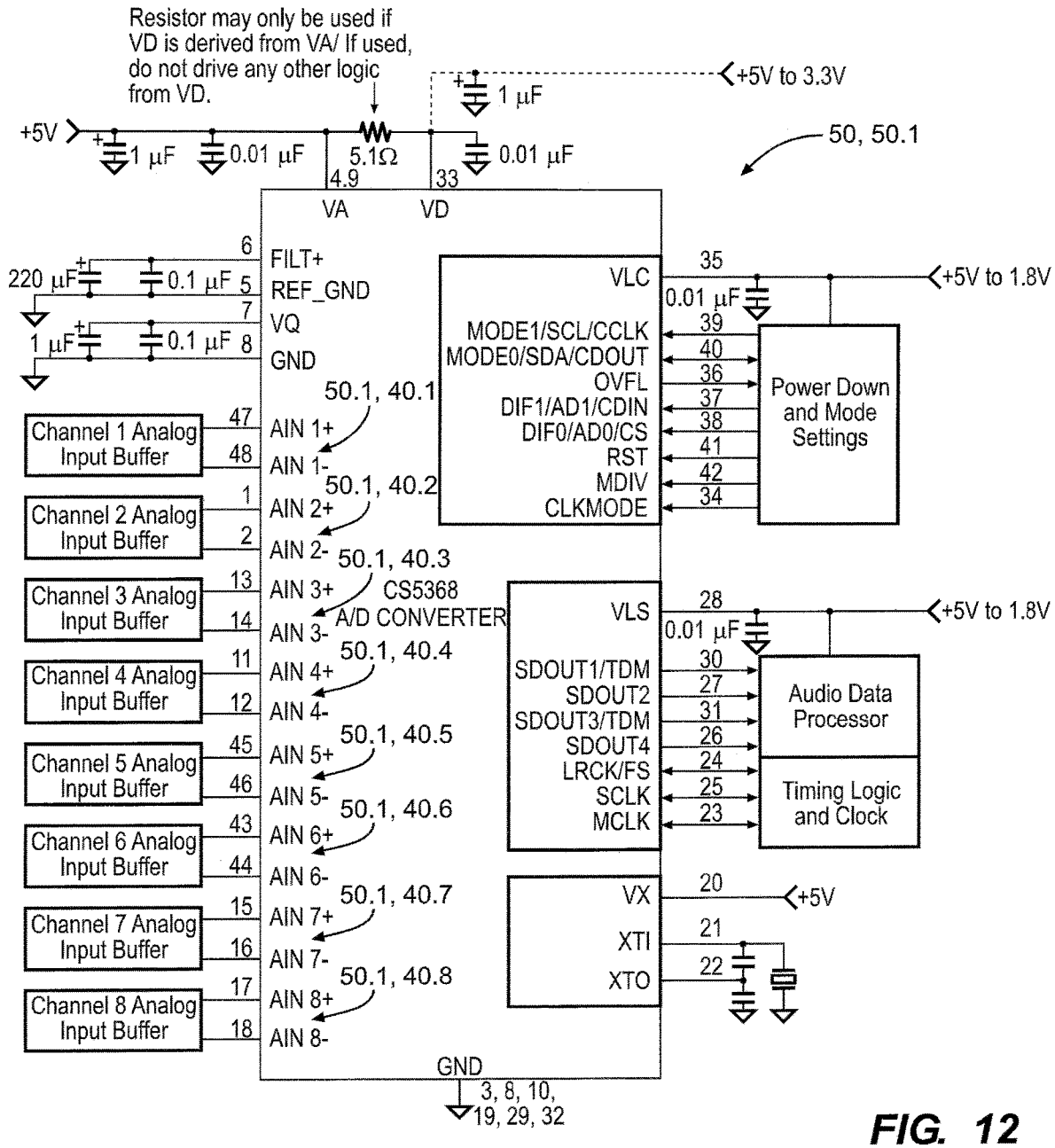
FIG. 12 illustrates a second block diagram of the analog-to-digital converter illustrated in FIG. 11.

Referring again to FIG. 4, and referring to FIGS. 11 and 12, in accordance with the first aspect 34.1 of the recording module 34, 34.1, the differential output of the second order Butterworth fully-differential low-pass filter 48, 48' is then coupled to an associated first aspect 50.1 of an analog-to-digital converter 50, 50.1, which is implemented with a Cirrus Logic, CS5368-CQZ 8-Channel analog-to-digital converter described in Cirrus Logic, "114 dB, 192 kHz, 8-Channel A/D Converter," DS624F5, 2014, 42 pages, which is incorporated herein by reference in its entirety, wherein each signal preprocessing channel 40, 40.1, 40.2,

40.3, 40.4, 40.5, 40.6, 40.7 is processed, in parallel and syncrhonously, by a corresponding separate 24-bit analog-to-digital converter 50, 50.1.

Figure 13:
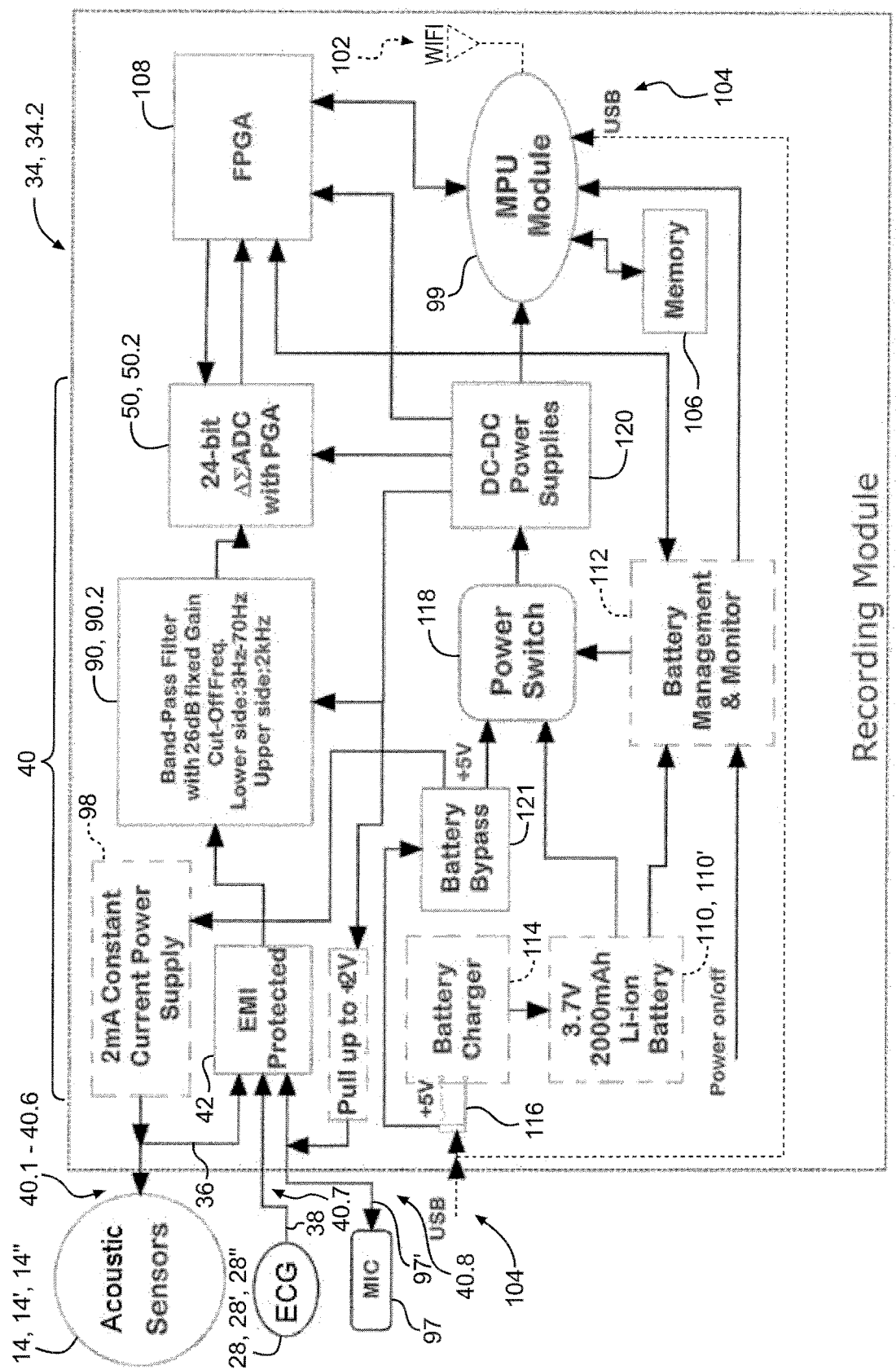
FIG. 13 illustrates a block diagram of a second aspect of a recording module of the coronary-artery-disease detection system illustrated in FIG. 1.

Referring also to FIG. 13, a second aspect 34.2 of a recording module 34, 34.2 is substantially the same as the above-described first aspect recording module 34, 34.1, except that the first 44.1 and second 44.2 high pass filters, controllable gain amplifier 46, 46.1, second order Butterworth fully-differential low-pass filter 48, 48'—that collectively function as a first aspect 90.1 of a band-pass filter 90, 90.1—and the associated first aspect analog-to-digital converter 50, 50.1, are replaced by a combination of a fixed gain, full-differential band-pass filter 90, 90.2 and a programmable-gain, second aspect analog-to-digital converter 50, 50.2 incorporating a Programmable Gain Amplifier (PGA).

Figure 14:
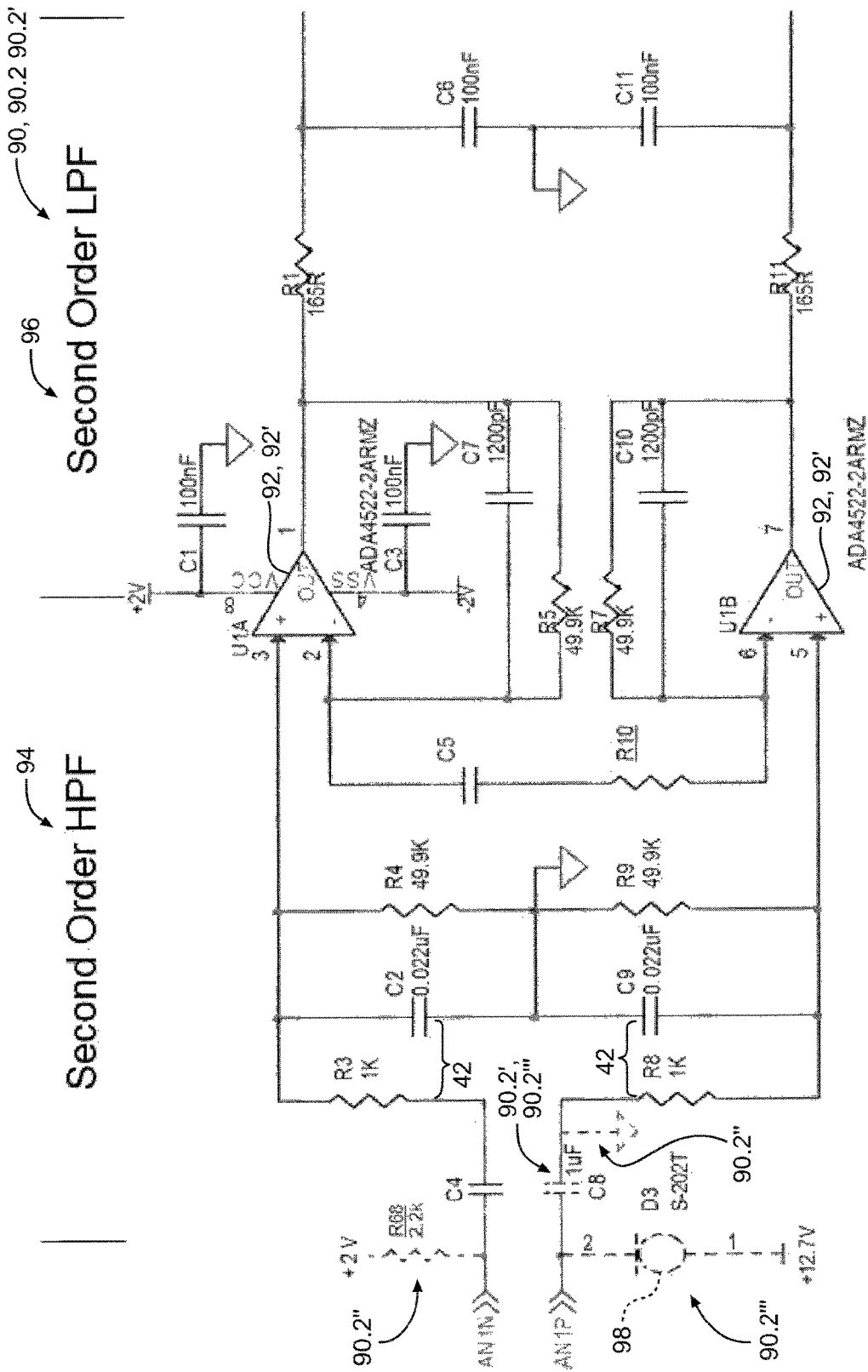
FIG. 14 illustrates a band-pass filter of the second aspect of the recording module illustrated in FIG. 13.
Figure 15:
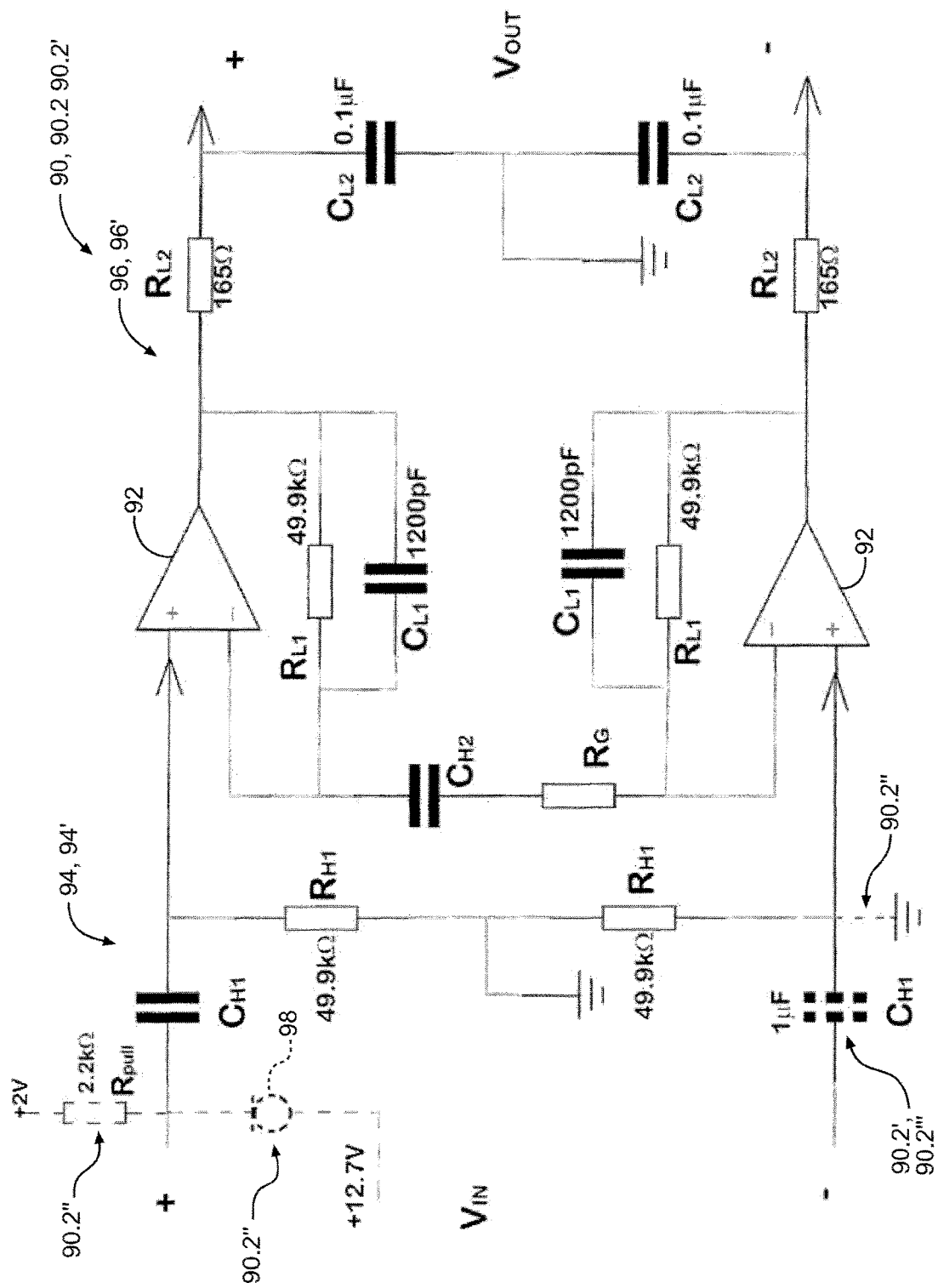
FIG. 15 illustrates the core elements of the band-pass filter illustrated in FIG. 14.

More particularly, referring to FIGS. 14 and 15, the fixed gain, full-differential band-pass filter 90, 90.2 comprises a balanced differential input and differential output configuration, each leg thereof incorporating a single operational amplifier 92, for example, an Analog Devices ADA4522-2 operational amplifier 92, 92', with an associated input-stage second-order high-pass filter network 94 associated with the input of the fixed gain, full-differential band-pass filter 90, 90.2, and an associated output-stage second-order low-pass filter network 96 associated with the output of the fixed gain, full-differential band-pass filter 90, 90.2, wherein the Analog Devices ADA4522-2 operational amplifier 92, 92' is described in Analog Devices, "55 V, EMI Enhanced, Zero Drift, Ultralow Noise, Rail-t0-Rail Output Operational Amplifiers," D13168-0-9/17(F), 2017, 33 pages, which is incorporated herein by reference in its entirety. For example, the fixed gain, full-differential band-pass filter 90, 90.2 illustrated in FIG. 14 has an application-specific gain, depending upon the type of signal being processed.

The associated set of high-pass cut-off frequencies fc1H, fc2H of the fixed gain, full-differential band-pass filter 90, 90.2 are given by:

$$fc1H = \frac{1}{2\pi \cdot R4 \cdot C4}, \quad (6)$$

$$fc2H = \frac{1}{2\pi \cdot R10 \cdot C5}; \quad (7)$$

and the associated set of low-pass cut-off frequencies fc1L, fc2L of the fixed gain, full-differential band-pass filter 90, 90.2 given by:

$$fc1L = \frac{1}{2\pi \cdot R10 \cdot C7}, \quad (7)$$

$$fc2L = \frac{1}{2\pi \cdot R1 \cdot C6}. \quad (8)$$

The associated EMI protection circuit 42 comprises R-C network R3-C2.

Referring to FIG. 15, the fixed gain, full-differential band-pass filter 90, 90.2 comprises cascaded high-pass and low-pass passive filter stages, which together in cooperation with the operational amplifier 92, 92' provide for a relatively wide pass band. The first stage of the filter is a two-pole high-pass stage 94' that comprises the capacitors $C_{H1}$, $C_{H2}$ and the resistors $R_{H1}$, $R_G$ to block any DC biasing and low frequency signals from the source. The second stage of the filter is a two-pole low-pass stage 96' that comprises the capacitors $C_{L1}$, $C_{L2}$ and the resistors $R_{L1}$, $R_G$. The full differential filter design both provides for a high common-mode rejection ratio (CMRR), and provides for a relatively flat asymmetrical pass band frequency response with a first portion thereof accounting for the low-pass response and the remaining second portion thereof accounting for the high-pass response. The bandwidth of the fixed gain, full-differential band-pass filter 90, 90.2 is the difference between these upper and lower −3 dB points, i.e. the difference between the higher corner cut-off frequency $f_H$ and the lower corner frequency cut-off frequency $f_L$. For example, for a fixed gain, full-differential band-pass filter 90, 90.2 with −3 dB cut-off frequencies $f_L$, $f_H$ at 15 Hz and 1 kHz, respectively, the associated pass-band frequency range would be 15 Hz to 1 kHz.

The component parameters of the circuit elements of the fixed gain, full-differential band-pass filter 90, 90.2 are adapted to the associated sensor that is the source of the signal being processed thereby. For example, in accordance with a first embodiment 90.2', the fixed gain, full-differential band-pass filter 90, 90.2, 90.2' is adapted to cooperate with a first aspect, passive, auscultatory sound-or-vibration sensor 14, 14', with capacitors $C_{H1}$ or C4 and C8 each having a value of 1 microfarad, with capacitors $C_{H2}$ or C5 having a value of 22 microfarads, and with the gain resistor $R_G$ or $R_{10}$ having a value of 2 KOhm so as to provide for a fixed gain of 33 dB to satisfy the requirements of a particular first aspect, passive, auscultatory sound-or-vibration sensor 14, 14', resulting in a 6 Hz cut-off frequency of the high-pass filter, so that the associated band-pass filter has a pass band of 6 Hz to 2 kHz. As another example, in accordance with a second embodiment 90.2", the fixed gain, full-differential band-pass filter 90, 90.2, 90.2" is adapted to cooperate with a microphone or background noise sensor 97 that provides for sensing the background sounds in the room in which the signals are gathered, so as to provide for prospectively compensating for a prospective adverse effect thereof on the auscultatory sound signals 36 that might otherwise interfere with the detection of cardiovascular disease, or might otherwise contribute to a false detection thereof. More particularly, for example, in one embodiment, the audio signal 97' from the microphone or background noise sensor 97 is processed by a corresponding signal preprocessing channel 40, 40.8 of the fixed gain, full-differential band-pass filter 90, 90.2, 90.2" for which the single-ended input (+) to which the microphone or background noise sensor 97 is connected to a +2 volt DC supply through a pull-up resistor $R_{PULL}$, the remaining input (−) is connected to signal ground, with capacitors $C_{H1}$ or C4 having a value of 0.22 microfarads, with capacitors $C_{H2}$ or C5 having a value of 2.2 microfarads, and with the gain resistor $R_G$ or $R_{10}$ having a value of 2 KOhm so as to provide for a fixed gain of 33 dB to satisfy the requirements of the microphone or background noise sensor 97, resulting in a 70 Hz cut-off frequency of the high-pass filter, so that the associated band-pass filter has a pass band of 70 Hz to 2 kHz, which provides for filtering what can be relatively prevalent acoustic noise in frequencies below 70 Hz that are otherwise outside a range of interest.

As yet another example, in accordance with a third embodiment 90.2''', the fixed gain, full-differential band-pass filter 90, 90.2, 90.2''' is adapted to cooperate with a set of second aspect 14, 14", active auscultatory sound-or-vibration sensors 14, 14", each of which requires power to operate, for example, each second aspect auscultatory sound-or-vibration sensor 14, 14" comprising an accelerometer incorporating an integrated circuit that requires power to operate. More particularly, for example, in one embodiment, the associated corresponding signal preprocessing channel(s) 40, 40.1, 40.2, 40.3, 40.4, 40.5, 40.6 of the fixed gain, full-differential band-pass filter 90, 90.2, 90.2''' each incorporate a 2 milliampere current source provided by an associated current regulator 98 powered from a +12.7 volt DC supply, with capacitors $C_{H1}$ or C4 and C8 having a value of 1 microfarad, with capacitors $C_{H2}$ or C5 having a value of 22 microfarads, and with the gain resistor $R_G$ or $R_{10}$ having a value of 4.99 KOhms so as to provide for a fixed gain of 26 dB to satisfy the requirements of a particular first aspect, passive, auscultatory sound-or-vibration sensor 14, 14', resulting in a 4 Hz cut-off frequency of the high-pass filter, so that the associated band-pass filter has a pass band of 4 Hz to 2 kHz. Alternatively, in another embodiment, a gain resistor $R_G$ or $R_{10}$ having a value of 14.3 KOhms so as to provide for a fixed gain of 26 dB to satisfy the requirements of a different first aspect, passive, auscultatory sound-or-vibration sensor 14, 14', results in a 3 Hz cut-off frequency of the high-pass filter, so that the associated band-pass filter would have a pass band of 3 Hz to 2 kHz.

Compared to the fixed gain, full-differential band-pass filter 90, 90.2 illustrated in FIG. 15, the third embodiment high-pass filter 44, 44''' illustrated in FIG. 7b is configured as a band-pass filter with a pass band of 3 Hz to 2 kHz, without the associated high-pass filter provided for by capacitor $C_{H2}$ illustrated in FIG. 15, and for which the cut-off frequency of the high-pass filter provided for by capacitor $C_{H1}$ is 3 Hz, in order to accommodate relatively low frequency components of an associated electrographic signal 38, which are in greater proportion than in corresponding auscultatory sound signals 36.

Figure 16:
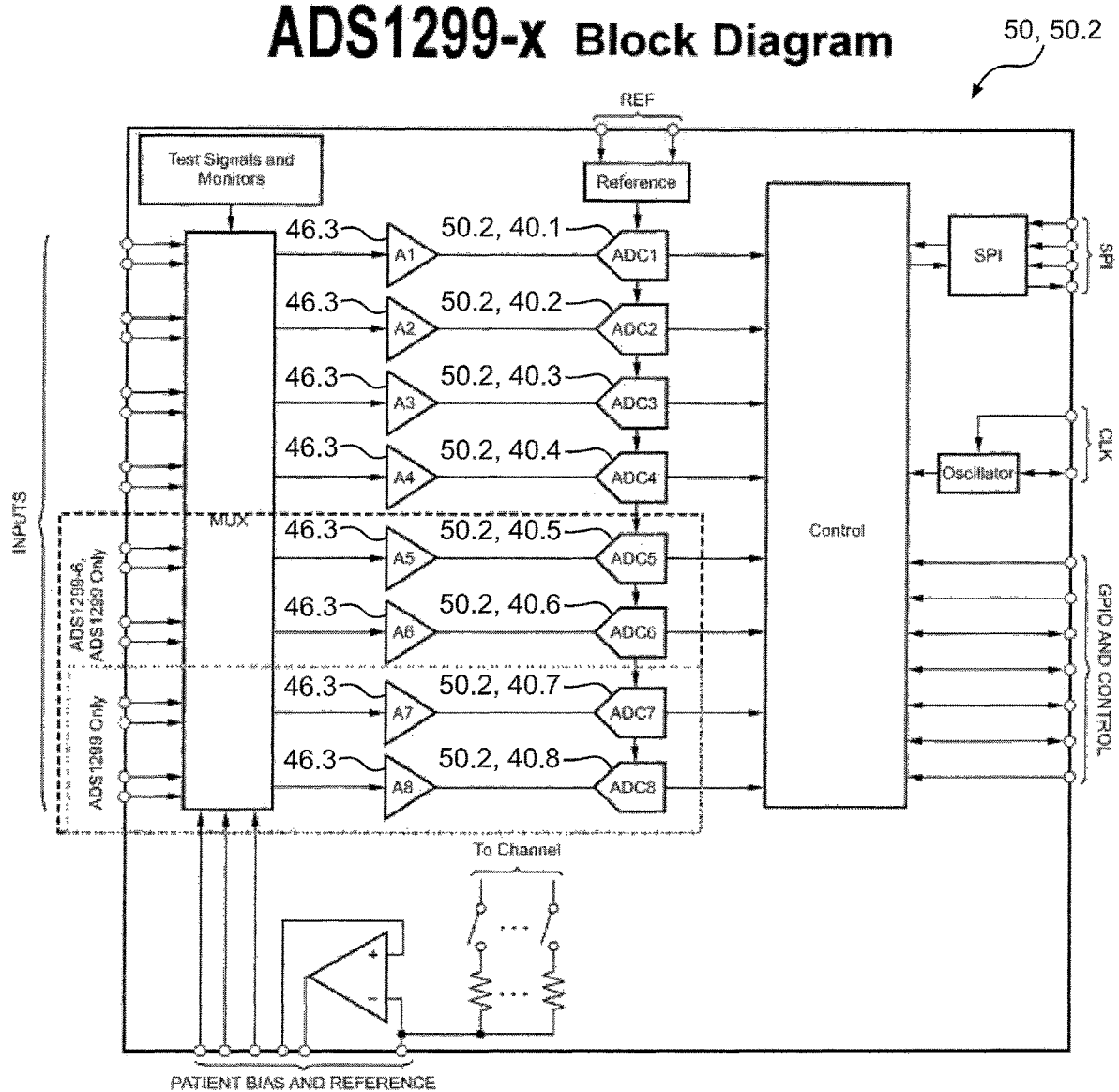
FIG. 16 illustrates a block diagram of an analog-to-digital converter of the second aspect of the recording module illustrated in FIG. 13.

Referring again to FIG. 13, and referring to FIG. 16, in accordance with the second aspect 34.2 of the recording module 34, 34.2, the differential output of the fixed gain, full-differential band-pass filter 90, 90.2 is then coupled to an associated second aspect 50.2 of an analog-to-digital converter 50, 50.2, which, for example, in one embodiment is implemented with a Texas Instruments, ADS1299IPAG 8-Channel analog-to-digital converter as described in Texas Instruments, "ADS1299-x Low-Noise 5-, 6-, 8-Channel, 24-Bit, Analog-to-Digital Converter for EEG and Biopotential Measurements," SBAS499C, July 2012, Revised January 2017, 81 pages, the latter of which is incorporated herein by reference in its entirety, wherein each signal preprocessing channel 40, 40.1, 40.2, 40.3, 40.4, 40.5, 40.6, 40.7, 40.8 is processed, in parallel and synchronously, by a corresponding separate 24-bit analog-to-digital converter 50, 50.2, the latter of which also incorporates a separate, separately-controllable associated controllable-gain amplifier 46, 46.3 for each signal preprocessing channel 40, 40.1, 40.2, 40.3, 40.4, 40.5, 40.6, 40.7.

Generally, the high-pass filters 44, 44', 44'', 44''' or the input-stage second-order high-pass filter network 94 of the associated band-pass filters 90, 90.1, 90.2, 90.2', 90.2'', 90.2''' are configured with a 3 dB cut-off frequency in the range of 3 Hz to 15 Hz to process an auscultatory sound signal 36 from an auscultatory sound-or-vibration sensor 14, 14', 14'', 1 Hz-3 Hz when used to process an electrographic signal 38 from an ECG sensor 28, 28', 28'', and 65 Hz-75 Hz when used to process an audio signal 97' from a microphone or background noise sensor 97; and the low-pass filters 48, 48' or the output-stage second-order low-pass filter network 96 of the associated band-pass filters 90, 90.1, 90.2, 90.2', 90.2'', 90.2''' are configured with a 3 dB cut-off frequency in the range of 500 Hz to 2.5 kHz.

Referring again to FIGS. 1, 4 and 13, the recording module 34, 34.1, 34.2 is under control of a micro-processing-unit (MPU) module 99 that provides for communicating with an associated docking system 100 via either a wireless interface 102 or a USB interface 104 that are either incorporated in, or peripherally connected to, the micro-processing-unit (MPU) module 99. The micro-processing-unit (MPU) module 99 further either incorporates, or interfaces with, associated memory 106, for example, either one or more of RAM, flash memory, EEPROM or Secure Digital Memory (i.e. an SD memory card). The micro-processing-unit (MPU) module 99 interfaces with a data & clock management module 108—for example, in one set of embodiments, implemented with a Field Programmable Gate Array (FPGA)—that provides for controlling the sampling process (e.g. the associated sampling clock) of the analog-to-digital converter 50, 50.1, 50.2 and for formatting the data therefrom and transmitting this formatted data to the micro-processing-unit (MPU) module 99 for subsequent transmittal to the docking system 100.

In one set of embodiments, for example, incorporating a wireless interface 102, the recording module 34, 34.1, 34.2 is powered by a battery 110, for example, a nominally 3.7 V lithium-ion battery 110', the charge of which is under control of a battery management and monitoring system 112 responsive to current, voltage and temperature, for example, by an STC3100 integrated circuit from STMicroelectronics, as described in STMicroelectronics, "STC3100 Battery monitor IC with Coulomb counter/gas gauge," January 2009, 21 pages, the latter of which is incorporated herein by reference in its entirety. The battery management and monitoring system 112 is programmable, and readable, through an I2C interface. Alternatively, the battery management and monitoring system 112 may be integrated with the battery 110, for example, using an RRC1120 Li-ion Semi-Smart Battery Pack from RRC Power Solutions. The battery 110 is charged by an associated battery charger 114 from an external +5V power supply via an associated power jack 116. Power from the battery 110 is provided through a power switch 118 under control of the battery management and monitoring system 112, to one or more DC-DC power supplies 120 that provide power to the electronics of the recording module 34, 34.1, 34.2, wherein the recording module 34, 34.1, 34.2 is automatically powered down if the voltage of the of the battery 110, 110' is less than a threshold, for example, less than 3.3 V.

Alternatively, in another set of embodiments, for example, incorporating a USB interface 104, the recording module 34, 34.1, 34.2 is powered directly from the +5 volt power supply of the USB interface 104, thereby precluding a need for a battery 110, 110', battery management and monitoring system 112, or battery charger 114, which may be therefore be excluded embodiments that are connected to the docking system 100, 100.1, 100.2 exclusively via a USB interface 104. For example, in some hospital environments, a wireless interface 102 would not be suitable because of interference with other wireless-based systems. In systems incorporating both wireless 102 and USB 104 interfaces, a battery bypass switch 121 provides for switching from battery power to USB power when the USB interface 104 is active.

Referring again to FIG. 1, a first aspect 100.1 of a docking system 100, 100.1 is implemented with a Windows-based computer—for example, an Intel NUC—embedded computer system 122 that interfaces with an LCD touch-screen display 124, both of which are powered from a power-management board 126 that receives power from an AC-powered AC/DC power adapter 128. A WIFI router 130 operatively coupled to the embedded computer system 122 provides for communicating at with the recording module 34, 34.1, 34.2, so as to provide for controlling the operation thereof responsive to operator inputs via the LCD touch-screen display 124, the latter of which also provides for displaying the resulting data that may be received either via a WIFI-wireless interface 102, 132 via the WIFI router 130, or via a separate USB interface 104. The power-management board 126 also provides power for charging the battery 110, 110' of the recording module 34, 34.1, 34.2 via an associated power jack 116.

Figure 17:
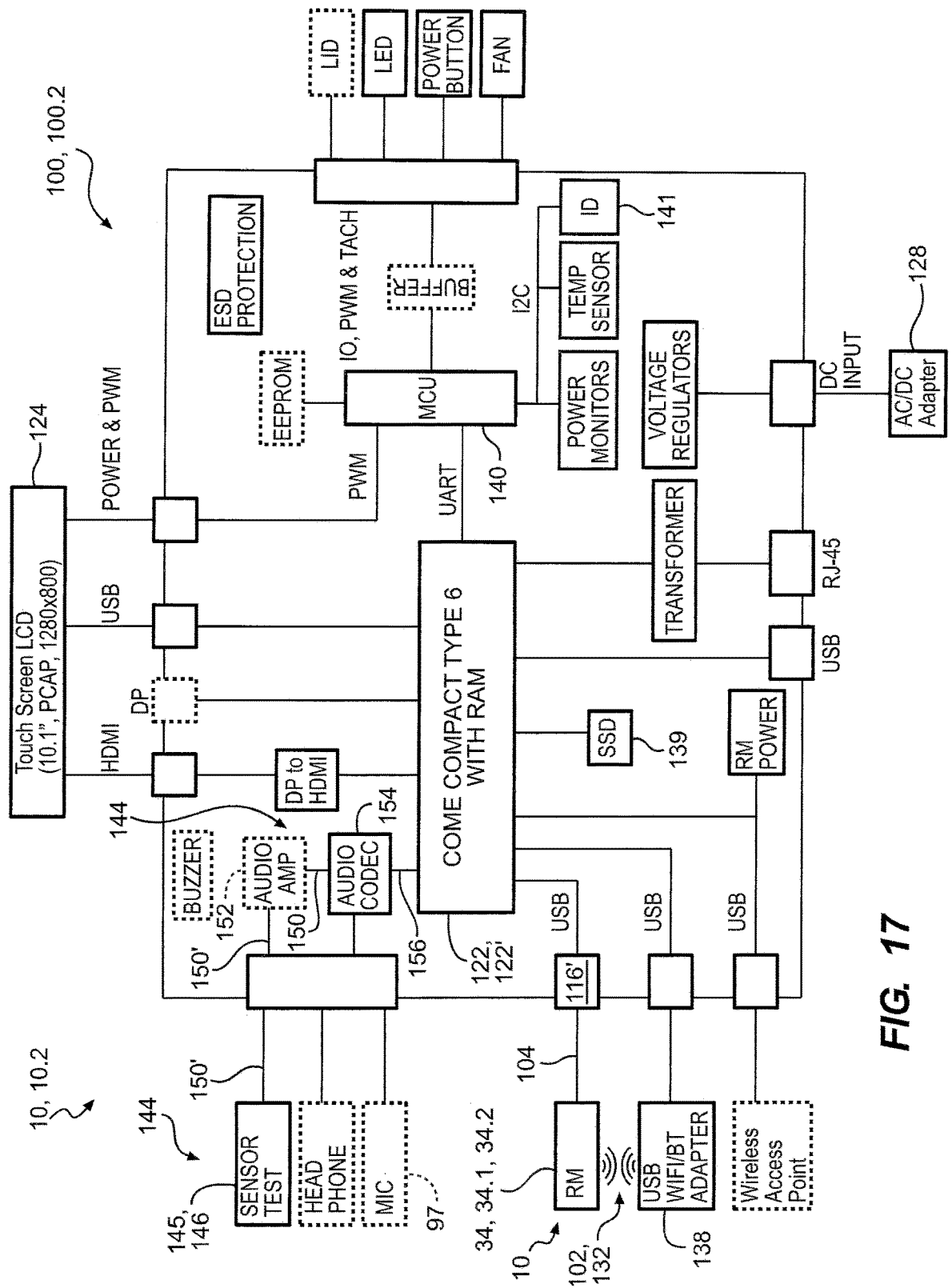
FIG. 17 illustrates a block diagram of a second aspect of a docking system of the coronary-artery-disease detection system illustrated in FIG. 1, in cooperation with a second aspect of a coronary artery disease detection system.

Referring to FIG. 17, a second aspect 10.2 of a coronary-artery-disease (CAD) detection system 10, 10.2 incorporates a second aspect 100.2 of the docking system 100, 100.2, the latter of which incorporates an embedded computer system 122, for example, a COM Express Compact Module 122, 122', with associated peripherals connected thereto via corresponding connectors (show as boxes in FIG. 17 on the periphery of the docking system 100, 100.2). For example, in one set of embodiments, a +5V power jack 116', for example, embodied in USB-connector, provides for powering or charging the recording module 34, 34.1, 34.2, that latter of which communicates with the docking system 100, 100.2 either exclusively via either a WIFI-wireless interface 102, 132 using an associated USB-connected WIFI or Bluetooth® adapter 138 or a USB interface 104; or via a combination of the two. Alternatively, the recording module 34, 34.1, 34.2 may be either wired directly to the docking system 100, 100.2 via a connectorless USB interface 104, or connected via a USB connector 116' to a cable that extends directly from the docking system 100, 100.2. An LCD touch-screen display 124 connected to the docking system 100, 100.2 provides for controlling the recording module 34, 34.1, 34.2 and processing and displaying results therefrom. The docking system 100, 100.2 further incorporates a solid-state disk 139 for storing data and programs.

For example, the COM Express Compact Module 122, 122' performs high-speed functions of the docking system 100, 100.2, for example, including control of, or communication with: 1) USB ports for the recording module 34, 34.1, 34.2, WIFI or Bluetooth® adapter 138, a wireless access point, etc.; 2) Gigabit Ethernet; 3) Audio codec that supports sensor integrity test signal output, input from a microphone or background noise sensor 97, and headphone output; 4) HDMI and DP interfaces for LCD monitors; 5) high performance processor for GUI and DAA; 6) SSD for storage of the operating system, application software and recorded test subject data; and 7) communication with an associated Microprocessor Control Unit (MCU) 140 via a UART port for hardware control and status. The Microprocessor Control Unit (MCU) 140 performs low-speed functions of the docking system 100, 100.2, for example, including the following monitoring, control and communication activities: 1) monitoring all voltage and current of various voltage regulators; 2) monitoring the board temperature; 3) controlling the LCD backlight brightness; 4) detecting the open or close status of the lid of the docking system 100, 100.2; 5) controlling the LED indictor for system status; 6) monitoring the power button status; 7) controlling and monitoring the fan speed; 8) accessing an optional EEPROM memory chip; 9) communicating with the COM Express Compact Module 122, 122' via a UART port for hardware control and status; and 10) accessing an ID chip 141 for the serial number, wherein the ID chip 141 provides a unique, factory-lasered 64-bit serial number that can be used to identify the hardware and system in the associated data that is captured by the docking system 100, 100.2 form the recording module 34, 34.1, 34.2.

Figure 18:
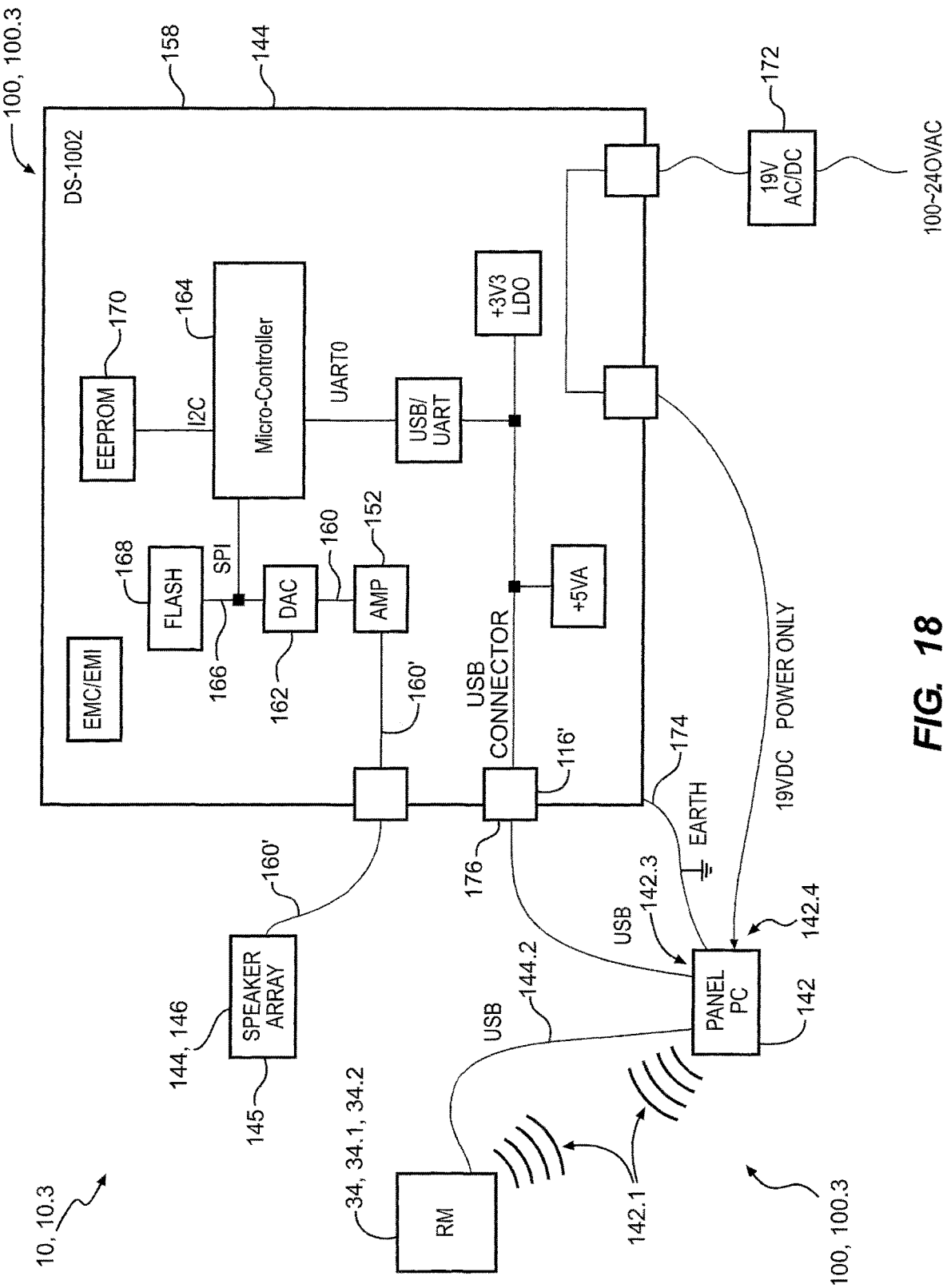
FIG. 18 illustrates a block diagram of a third aspect of a docking system of the coronary-artery-disease detection system illustrated in FIG. 1, in cooperation with a third aspect of a coronary artery disease detection system.

Referring to FIG. 18, a third aspect 10.2 of a coronary-artery-disease (CAD) detection system 10, 10.3 incorporates an alternative third aspect 100.3 of the docking system 100, 100.3, the latter of which incorporates a panel PC 142 that provides for an integrated computer and LCD touchscreen display system that further incorporates a wireless/Bluetooth® interface 142.1, USB interfaces 142.2, 142.3 and a power interface 142.4, wherein the associated LCD touch-screen display system provides for controlling the recording module 34, 34.1, 34.2 via the wireless/Bluetooth® interface 142.1, and processing and displaying results received therefrom via one of the USB interfaces 142.2.

Referring to FIGS. 1, and 17-22, the docking system 100, 100.1, 100.2, 100.3 further incorporates a sensor-integrity-test sub-system 144 comprising an array 145 of a plurality of sound generators 146—at least equal in number to the number of auscultatory sound-or-vibration sensors 14—for testing the array 18 of auscultatory sound-or-vibration sensors 14 in order to detect either a failure or degradation of any of the auscultatory sound-or-vibration sensors 14. For example, in accordance with one test procedure, the auscultatory sound-or-vibration sensors 14 are tested both prior to, and following, a gathering of auscultatory sound-or-vibration signals 36 from a test subject 12, so as to mitigate against inconvenience to the test subject 12 that would otherwise result if one or more of the auscultatory sound-or-vibration sensors 14 was defective.

For example, in accordance with one set of embodiments, each of the plurality of sound generators 146 of the array 145 comprises a piezoelectric sound generator 146, 146' similar in construction to the piezoelectric sensor disk of the auscultatory sound-or-vibration sensors 14, as described in U.S. Provisional Application No. 62/568,155 incorporated herein by reference, but with an AC signal applied across the associated piezoelectric material, which causes the piezoelectric sensor disk to vibrate, and causes the associated metallic diaphragm disk substrate to act as a speaker to generate sound. Each piezoelectric sound generator 146, 146' is located at the base of a well 148 that is sized to receive a corresponding auscultatory sound-or-vibration sensor 14 to be tested and align each auscultatory sound-or-vibration sensor 14 with a corresponding sound generator 146, 146', with the metallic diaphragm disk substrate of the piezoelectric sound generator 146, 146' facing upwards so as to abut the polyester film layer covering the piezoelectric sensor disk of the corresponding auscultatory sound-or-vibration sensor 14 when the latter is placed in the corresponding well 148 when performing an integrity-test thereof.

In accordance with one set of embodiments, the piezoelectric sound generators 146, 146' are picked as a batch of transducers with similar frequency response (+−5 dB from median) within the frequency range of 0 to 2 kHz.

Figure 19:
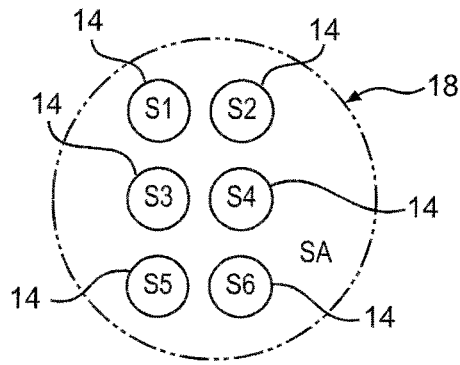
FIG. 19 illustrates an array of six auscultatory sound-or-vibration sensors of the coronary-artery-disease detection system illustrated in FIG. 1.
Figure 20:
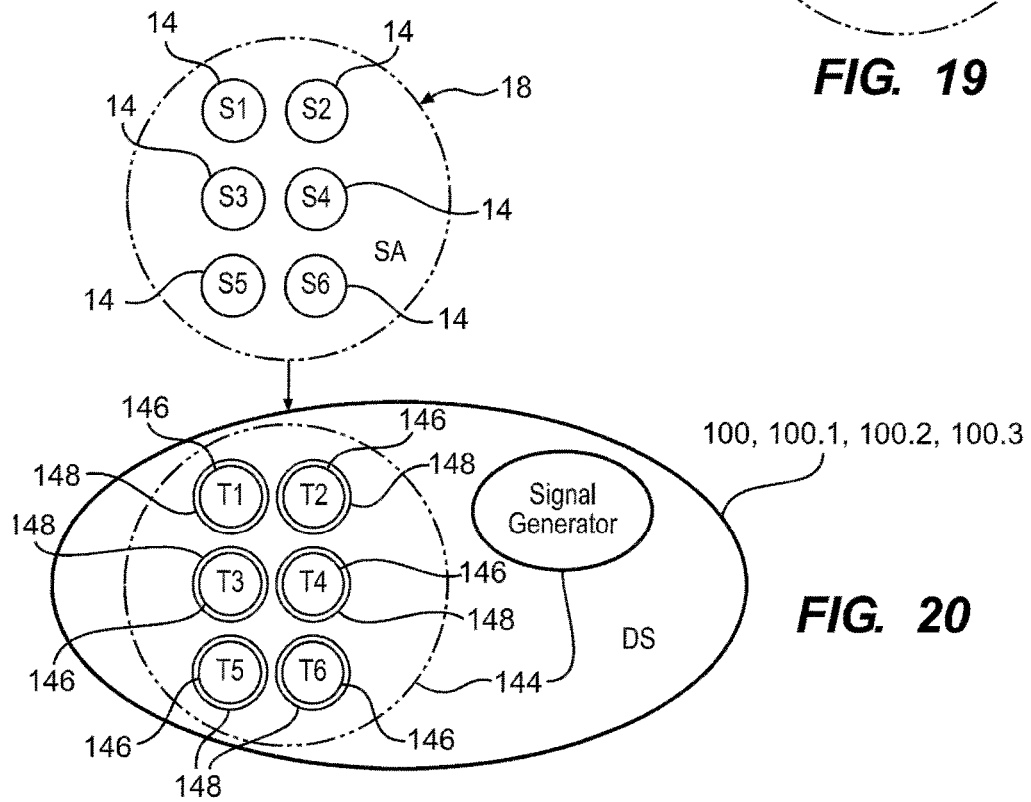
FIG. 20 illustrates the array of auscultatory sound-or-vibration sensors illustrated in FIG. 19 being placed over a corresponding array of sound generators, after which the auscultatory sound sensors are subjected to sound signals from corresponding sound generators in order to test the auscultatory sound sensors.
Figure 21:
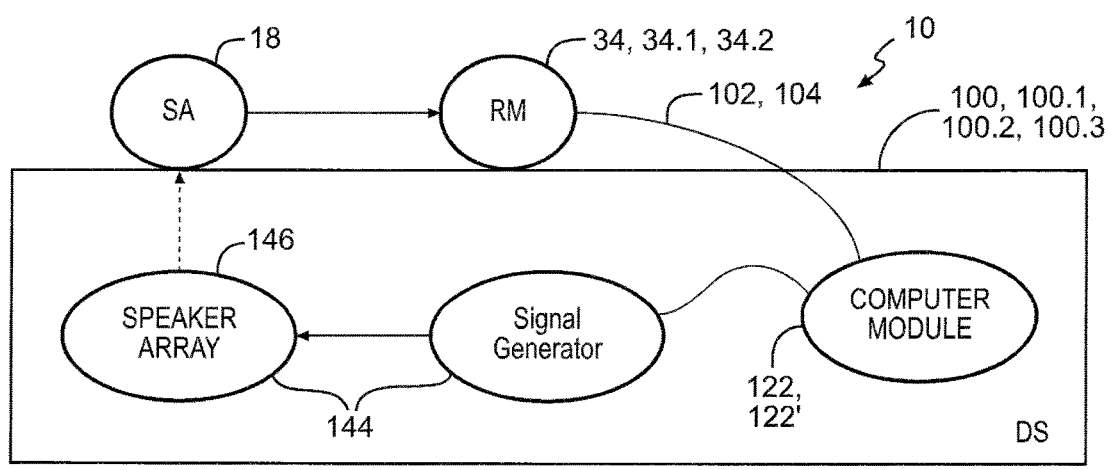
FIG. 21 illustrates a block diagram of the testing and subsequent use of an array of auscultatory sound sensors.

For example, referring to FIG. 19, in accordance with one set of embodiments, there are six auscultatory sound-or-vibration sensors 14—designated S1 to S6—in the array 18 of auscultatory sound-or-vibration sensors 14 to be tested, the latter of which, referring to FIG. 21, are attached to the recording module 34, 34.1 which is operated normally during the sensor-integrity test, and which is in wireless or USB communication with the associated docking system 100, 100.1, 100.2, 100.3, so as to provide for preprocessing and then transmitting the associated resulting acoustic signals 36' from the auscultatory sound-or-vibration sensors 14—recorded during the test—to the docking system 100, 100.1, 100.2, 100.3 for analysis of the integrity-test results. The acoustic signals 36' acquired during the integrity test are filtered by the band-pass filter 90 of the recording module 34, 34.1, 34.2, the same as for auscultatory sound signals 36 when gathered from a test subject 12.

In accordance with the second aspect 100.2 of the docking system 100, 100.2, the piezoelectric sound generators 146, 146' are driven either by an amplified analog signal 150' from an audio amplifier 152 that is driven by an analog signal 150 from an audio CODEC 154, or directly from the audio CODEC 154 the latter of which is driven by a digital signal 156 from the COM Express Compact Module 122, 122' based upon an associated test signal that is stored on a file, for example, on the associated solid-state disk 139, responsive to an associated integrity-test software application running on the COM Express Compact Module 122, 122'. In accordance with the third aspect 100.3 of the docking system 100, 100.3, the piezoelectric sound generators 146, 146' are driven from an audio signal generator card 158 by an amplified analog signal 160' from an audio amplifier 152 driven by an analog signal 160 from a digital-to-analog converter 162 driven by a micro-controller 164 either responsive to a digital signal waveform 166 stored on flash memory 168, or generated in real time by the micro-controller 164, responsive to a stored program on EEPROM 170. For example, in accordance with one set of embodiments, the associated amplified analog signal 150', 160' from the audio amplifier 152 is applied in parallel to each of the piezoelectric sound generators 146, 146' of the array 145. In one set of embodiments, the audio signal generator card 158 is powered from an AC-powered 19 VDC power supply 172, wherein the power therefrom is also coupled to the panel PC 142. In one set of embodiments, the panel PC 142 is grounded to earth ground 174 by connection to the audio signal generator card 158. Alternatively, if another source of earth ground 174 is established for the panel P142, or if the panel PC 142 is configured so as to not require an earth ground 174, then the 19 VDC power supply 172 could be connected directly to the panel PC 142, rather than via the audio signal generator card 158. Furthermore, the second USB interface 142.3 on the panel PC 142 may be used to provide +5 VDC to the audio signal generator card 158 by connection to a USB port 176 on the audio signal generator card 158, the latter of which can also be used to receive associated control signals from the panel PC 142 that provide for initiating the sensor integrity test.

Referring to FIGS. 21-26, a sensor-test acoustic-frequency waveform W—generated in accordance with an associated sensor-test acoustic-frequency waveform generation procedure 2200—is applied to the sound generators 146, 146' in accordance with an associated auscultatory-sensor integrity-test procedure 2400 that is run on the embedded computer system 122, 122' or panel PC 142 of the docking system 100, 100.1, 100.2, 100.3. The auscultatory-sensor integrity-test procedure 2400 provides for generating and applying either an analog signal 150, or an amplified analog signal 150', 160', to drive the sound generators 146, 146'; provides for receiving the resulting acoustic signals 36' from the array 18 of auscultatory sound-or-vibration sensors 14 via the recording module 34, 34.1, 34.2; and provides for determining whether any of the auscultatory sound-or-vibration sensors 14 have failed or diminished, or whether there are any breaks in the associated wiring of the auscultatory sound-or-vibration sensors 14 or problems with the connection of the auscultatory sound-or-vibration sensors 14 to the recording module 34, 34.1, 34.2.

Figure 22:
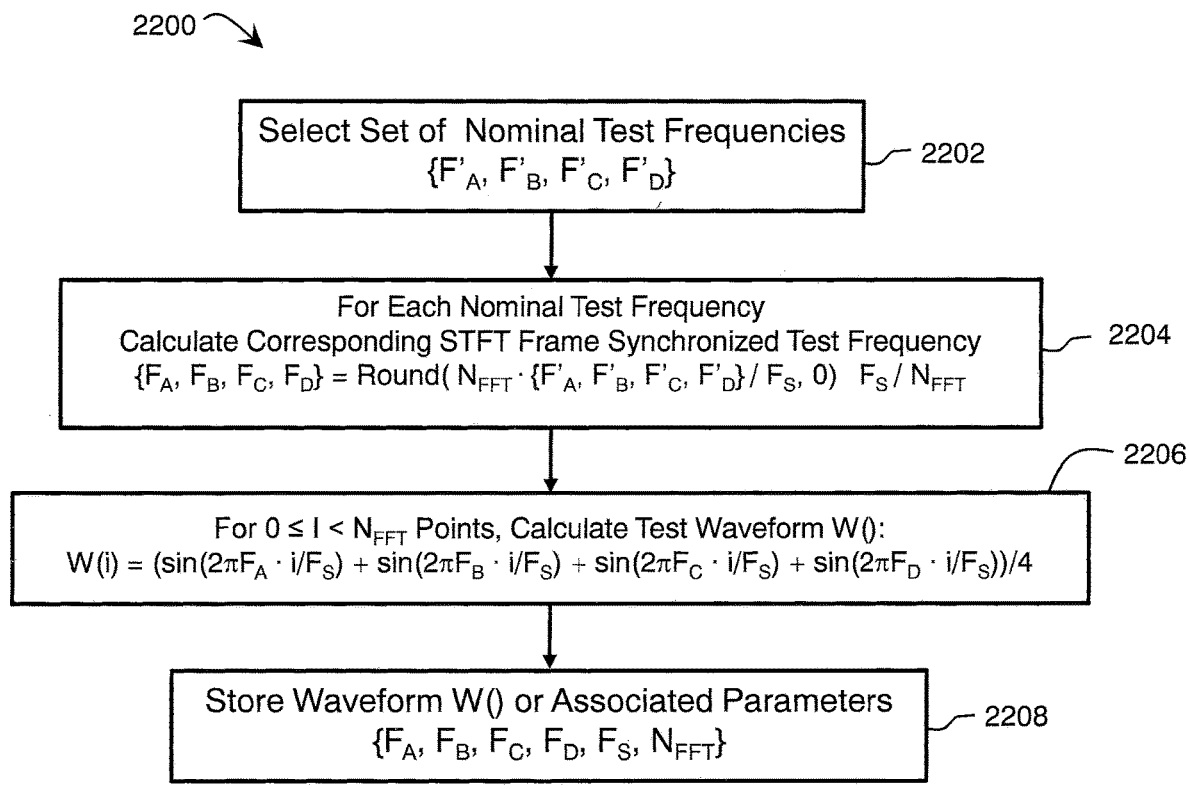
FIG. 22 illustrates a flow chart of a sensor-test acoustic-frequency waveform generation procedure.

More particularly, referring to FIG. 22, the amplified analog signal 150', 160' applied to the sound generators 146, 146' during the auscultatory-sensor integrity-test procedure 2400 is generated as a composite of a plurality of pure tones. For example, in accordance with one set of embodiments, in step (2202), a set of four sinusoidal tones of a corresponding respective four different nominal test frequencies $F'_A$, $F'_B$, $F'_C$, $F'_D$, each of equal magnitude, within an expected relevant range of frequencies of the auscultatory sound signals 36 that may be associated with coronary-artery disease. For example, in one set of embodiments, the four tones are at sinusoidal nominal test frequencies of $F'_A$=500 Hz, $F'_B$=650 Hz, $F'_C$=800 Hz and $F'_D$=1100 Hz.

Looking ahead, for each auscultatory sound-or-vibration sensor 14, a sample of $N_{FFT}$ samples of the associated acoustic signal 36'—generated responsive to an acoustic stimulus by the piezoelectric sound generators 146, 146' responsive to the sensor test acoustic-frequency waveform W, and sampled at a sampling frequency of $F_S$ $H_z$, for example, 24 kHz—are transformed from the time domain to the frequency domain by a Short Time Fourier Transform (STFT) process, wherein specific frequency components in the frequency domain output are then analyzed to assess the integrity of the auscultatory sound-or-vibration sensors 14. Accordingly, in order to mitigate against spectral leakage by an associated non-windowed $N_{FFT}$-point Fast Fourier Transform (FFT) algorithm, the actual test frequencies $F_A$, $F_B$, $F_C$, $F_D$ underlying the corresponding $N_{FFT}$-point time-domain sensor test acoustic-frequency waveform W are adapted so that each has an integral number of associated cycles therewithin, or equivalently, so that each test frequency $F_A$, $F_B$, $F_C$, $F_D$ is an integral multiple of the sampling frequency $F_S$ divided by the number of samples $N_{FFT}$ in the time-domain sensor test acoustic-frequency waveform W, i.e., an integral multiple of $F_S/N_{FFT}$. Accordingly, in step (2204), this condition may be satisfied by the following test frequencies $F_A$, $F_B$, $F_C$, $F_D$ that are relatively close to the nominal test frequencies $F'_A$, $F'_B$, $F'_C$, $F'_D$:

$$F_A = \text{Round}\left(\frac{N_{FFT} \cdot F'_A}{F_S}, 0\right) \cdot \frac{F_S}{N_{FFT}}; \quad (9a)$$

$$F_B = \text{Round}\left(\frac{N_{FFT} \cdot F'_B}{F_S}, 0\right) \cdot \frac{F_S}{N_{FFT}}; \quad (9b)$$

$$F_C = \text{Round}\left(\frac{N_{FFT} \cdot F'_C}{F_S}, 0\right) \cdot \frac{F_S}{N_{FFT}}; \text{ and} \quad (9c)$$

$$F_D = \text{Round}\left(\frac{N_{FFT} \cdot F'_D}{F_S}, 0\right) \cdot \frac{F_S}{N_{FFT}}. \quad (9d)$$

Accordingly, for the nominal test frequencies $F'_A$=500 Hz, $F'_B$=650 Hz, $F'_C$=800 Hz and $F'_D$=1100 Hz, and for $N_{FFT}$=4096 points, the corresponding resulting actual test frequencies (and number of cycles in the sensor test acoustic-frequency waveform W) are respectively, $F_A$=498.046875 Hz (85 cycles), $F_B$=650.390625 Hz (111 cycles), $F_C$=802.734375 Hz (137 cycles) and $F_D$=1101.5625 Hz (188 cycles), wherein each test frequency $F_A$, $F_B$, $F_C$, $F_D$ is evenly divisible by $F_S/N_{FFT}$=5.859375 Hz Then, in step (2206), the result of which is illustrated in FIG. 23a, a normalized $N_{FFT}$-point time-domain sensor test acoustic-frequency waveform W is then generated by summing the individual frequency components, as follows, for $0 \le i < N_{FFT}$:

$$W(i) = \frac{\sin\left(\frac{2\cdot\pi\cdot F_A \cdot i}{F_S}\right) + \sin\left(\frac{2\cdot\pi\cdot F_B \cdot i}{F_S}\right) + \sin\left(\frac{2\cdot\pi\cdot F_C \cdot i}{F_S}\right) + \sin\left(\frac{2\cdot\pi\cdot F_D \cdot i}{F_S}\right)}{4}. \quad (10)$$

Then, in step (2208), the resulting sensor test acoustic-frequency waveform W—or, equivalently, the associated set of parameters by which it is generated—is stored in the docking system 100, 100.1, 100.2, 100.3 for subsequent use in driving the plurality of sound generators 146 during the auscultatory-sensor integrity-test procedure 2400.

Figure 23:
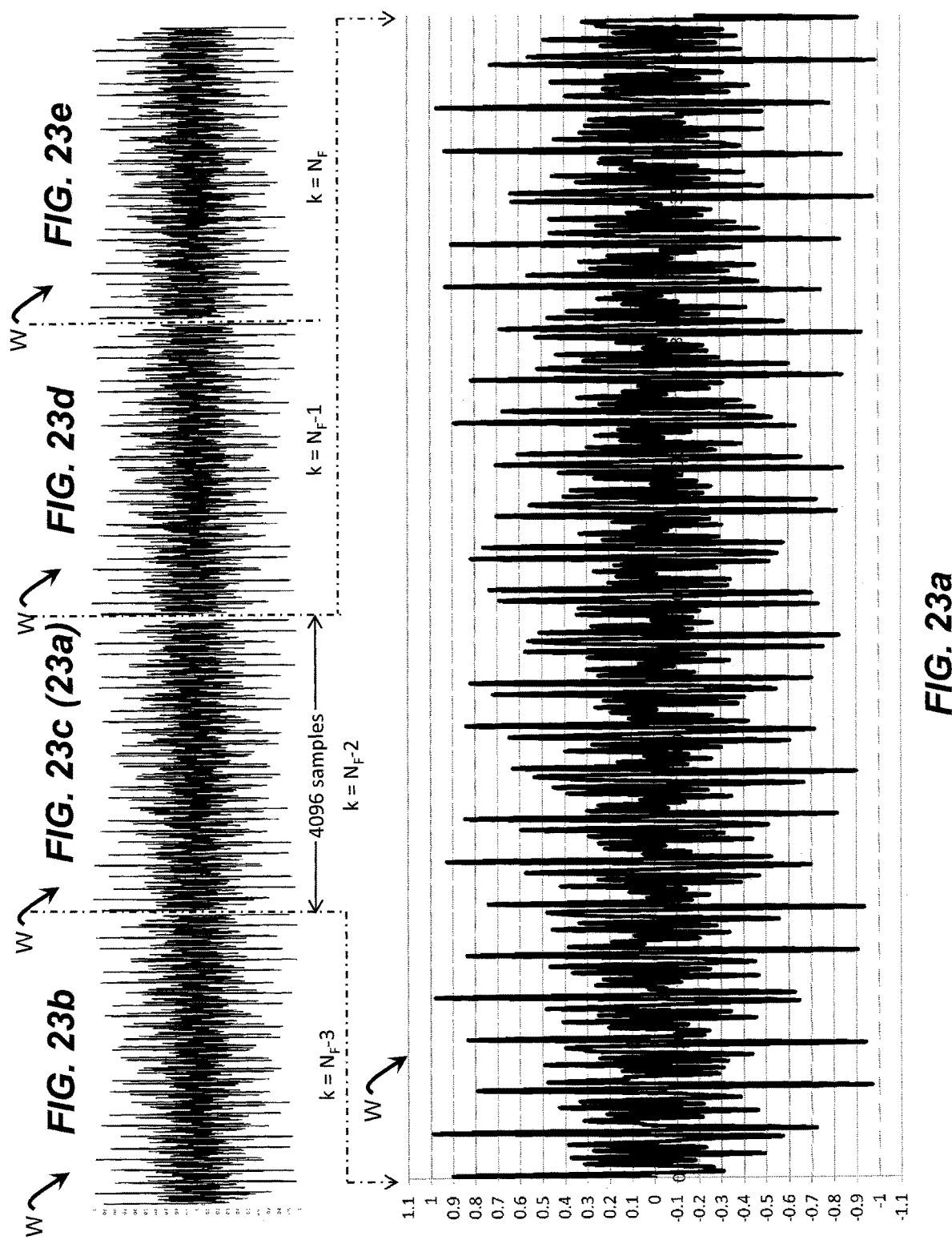
FIG. 23a illustrates a sensor-test acoustic-frequency waveform repetitively used to drive the sound generators when testing the plurality of auscultatory sound sensors during an associated auscultatory-sensor integrity-test procedure.
FIGS. 23b-23e illustrate repetitions of the sensor-test acoustic-frequency waveform used to drive the sound generators when testing the plurality of auscultatory sound sensors during an associated auscultatory-sensor integrity-test procedure.
Figure 24:
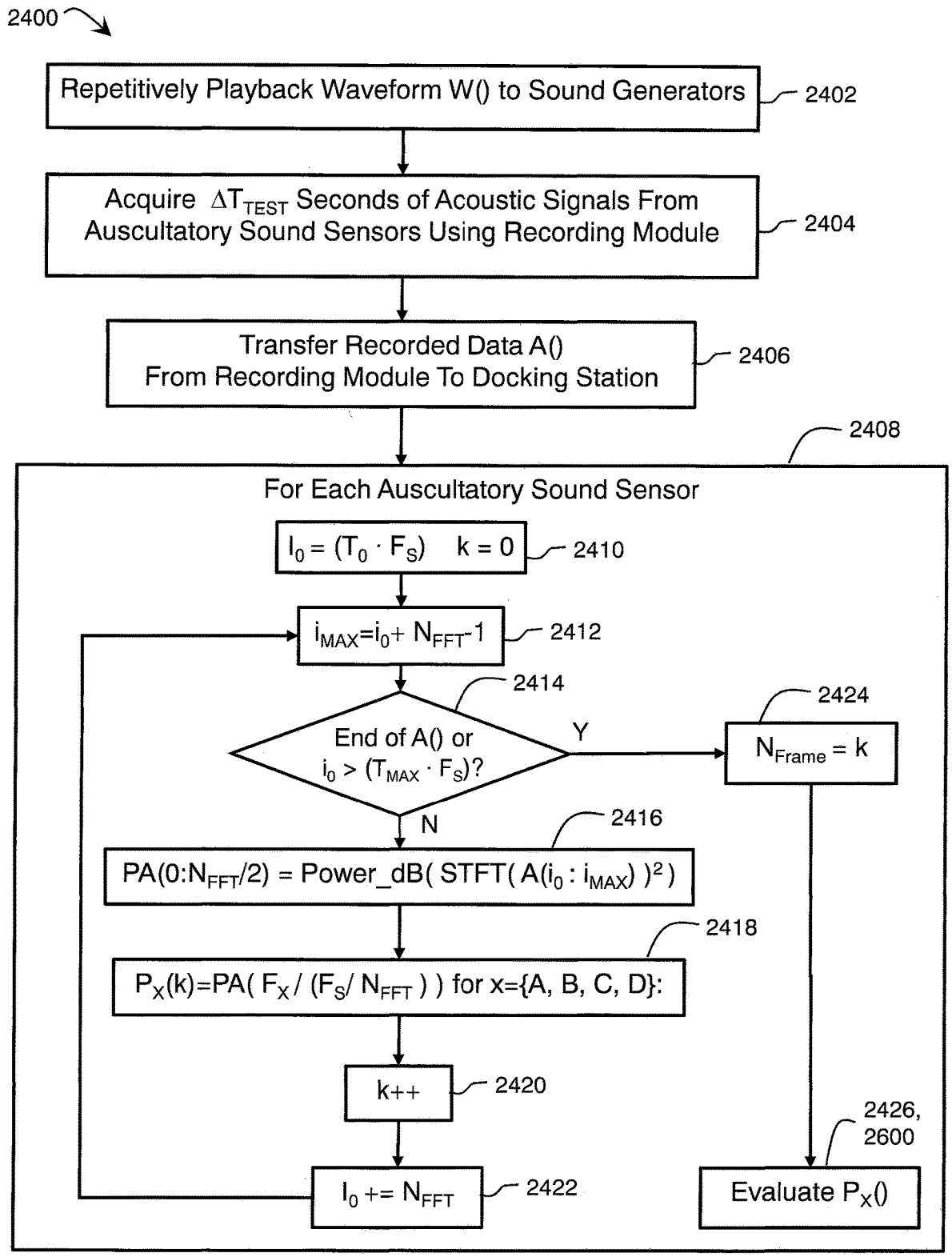
FIG. 24 illustrates a flow chart of a first phase of an auscultatory-sensor integrity-test for integrity-testing the plurality of auscultatory sound sensors illustrated in FIG. 19 using the sound generators of a docking system as illustrated in FIG. 20, for the coronary-artery-disease detection system illustrated in FIGS. 1 and 21.

Referring to FIG. 24, in step (2402), successive, respective occurrences of the $N_{FFT}$-point time-domain sensor test acoustic-frequency waveform W—for example, as shown in FIGS. 23b-23$_e$, illustrating the last four of NF total occurrences,—are applied to the plurality of sound generators 146 in acoustic communication with the corresponding plurality of auscultatory sound-or-vibration sensors 14 adjacent thereto when placed in the wells 148 of the docking system 100, 100.1, 100.2, 100.3. For example, in accordance with the third aspect docking system 100, 100.3, the sensor test acoustic-frequency waveform W stored on the flash memory 168 is successively and repetitively played back to the digital-to-analog converter 162, the resulting analog signal 160 is amplified by the associated audio amplifier 152, and the resulting amplified analog signal 160' is applied to the plurality of sound generators 146.

Then, in step (2404), the docking system 100, 100.1, 100.2, 100.3 causes the recording module 34, 34.1, 34.2 to preprocess and record $\Delta T_{TEST}$ seconds of acoustic signals 36', for example, a duration of about five seconds, sufficient to span a plurality of $N_{FFT}$-point frames of the acoustic signals 36', each recorded at a sampling rated of $N_S$ Hz, resulting in a total of $N_S \times \Delta T_{TEST}$ samples. Then, in step 2406, the recorded acoustic signals 36' of a time-series A—containing $N_S \times \Delta T_{TEST}$ samples—are transferred to the docking system 100, 100.1, 100.2, 100.3, for example, via either a wireless 102 or USB 104 interface.

Figure 25:
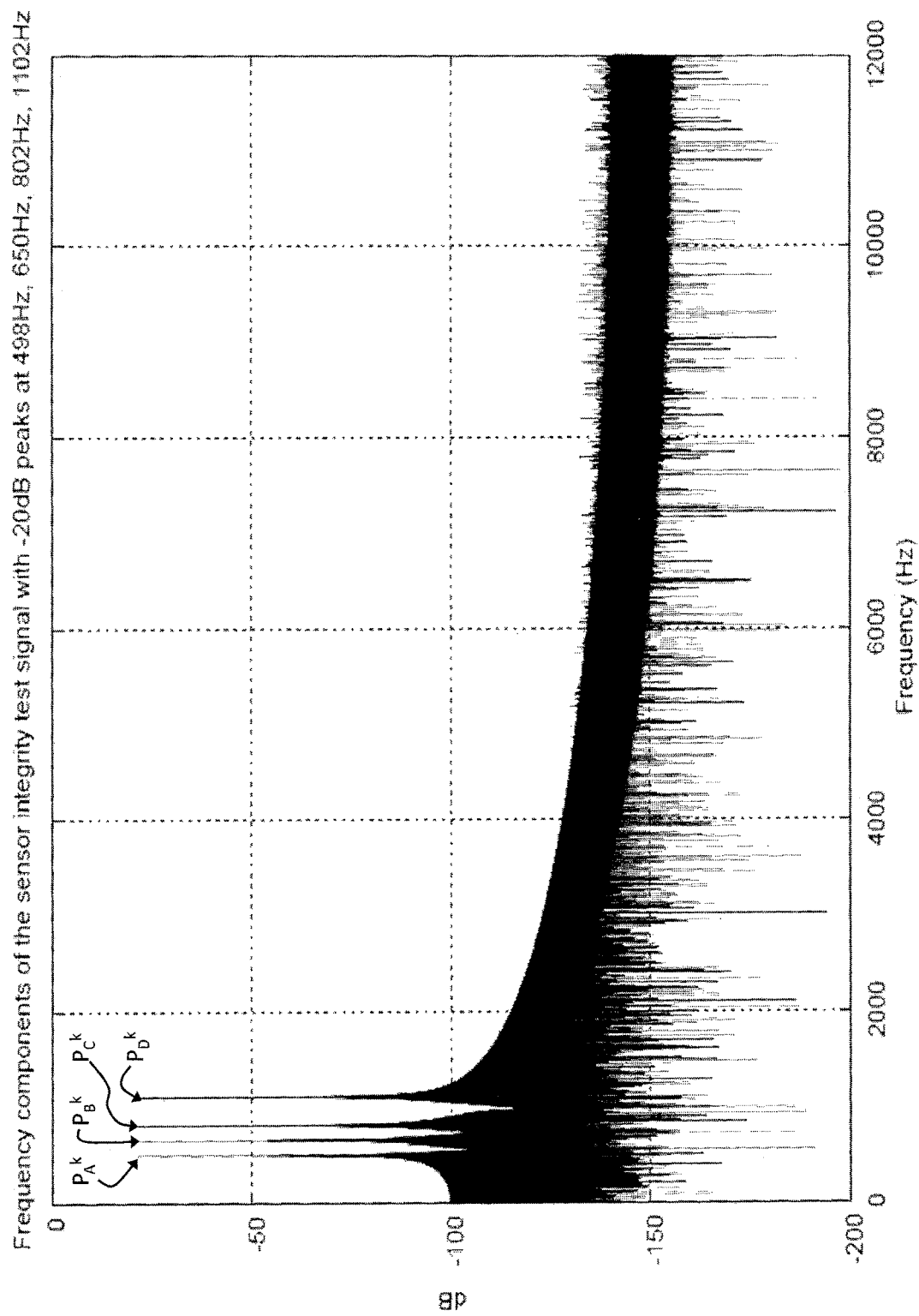

Then, in step 2408, the acoustic signals 36' from each of the plurality of auscultatory sound-or-vibration sensors 14 are processed, beginning with step (2410), by initializing a pointer $i_0$ to point to the beginning of the first $N_{FFT}$-point frame of the acoustic signal 36' to be processed—i.e. the acoustic data 36'—, and by initializing a frame counter k to a value of zero. Then, in step (2412), a pointer $i_{MAX}$ is set to point to the last sample of the corresponding $N_{FFT}$-point frame of the acoustic signal 36' to be processed, i.e. to a value of $i_0+N_{FFT}-1$. Then, in step (2414), if the end of time-series A has not been reached, or less than $T_{MAX}$ seconds of data has been processed, for example, in one set of embodiments, less than three seconds, then in step (2416), a Short Term Fourier Transform (STFT) of the $N_{FFT}$-point frame of acoustic data 36' is calculated, i.e. an $N_{FFT}$-point Fast Fourier Transform (FFT) of one $N_{FFT}$-point frame subset of the entire acoustic signal 36' time series, and the values of the resulting series are each squared and logarithmically expressed in dB to give a spectral series PA providing a measure of the power of the acoustic data 36' as a function of frequency. Since the FFT of a real signal is conjugate symmetric, only the first $N_{FF}/2+1$ values are returned in the spectral series PA, covering the frequency range 0 to $F_S/2$. The Short Term Fourier Transform (STFT) provides for resolutions in both time and frequency, with a time resolution of $N_{FF}/F_S$, and a frequency resolution of $F_S/N_{FF}$, which for $N_{FF}=4096$ and $F_S=24$ kHz, are 0.17 sec and 5.86 Hz, respectively. For example, FIG. 25 illustrates a plot of the spectral series PA for one of the $N_{FFT}$-point frames of acoustic data 36', which exhibits peaks at each of the test frequencies $F_A$, $F_B$, $F_C$, $F_D$.

Then, in step (2418), the power of each of the test frequencies $F_A$, $F_B$, $F_C$, $F_D$ is stored as the $k^{th}$ value in a corresponding test-frequency-power array $P_A$, $P_B$, $P_C$, $P_D$, i.e.:

$$P_A(k) = PA\left(F_A / \frac{F_S}{N_{FFT}}\right) = PA(85); \quad (11a)$$

$$P_B(k) = PA\left(F_B / \frac{F_S}{N_{FFT}}\right) = PA(111); \quad (11b)$$

$$P_C(k) = PA\left(F_C / \frac{F_S}{N_{FFT}}\right) = PA(137); \text{ and} \quad (11c)$$

$$P_D(k) = PA\left(F_D / \frac{F_S}{N_{FFT}}\right) = PA(188). \quad (11d)$$

Then, in step (2420), the frame counter k is incremented, and in step (2422), the pointer $i_0$ is updated to point to the beginning of the next $N_{FFT}$-point frame of acoustic data 36' in the acoustic signal 36' to be processed, adjacent in time to the just-processed previous $N_{FFT}$-point frame of acoustic data 36', after which the process of step (2408) repeats, beginning with step (2412) until the condition of step (2414) is satisfied, after which the total number of frames $N_{Frame}$ is set equal to the last value of the frame counter k, and, from step (2426), the test-frequency-power arrays $P_A$, $P_B$, $P_C$, $P_D$ are analyzed in a second phase 2600 of the auscultatory-sensor integrity-test procedure 2400, to determine whether or not any of the auscultatory sound-or-vibration sensors 14 might be defective.

More particularly, referring to FIG. 26, in step (2602), the average spectral power $\overline{P}_A$, $\overline{P}_B$, $\overline{P}_C$, $\overline{P}_D$ at each of the corresponding test frequencies $F_A$, $F_B$, $F_C$, $F_D$ is calculated by summing the corresponding spectral powers from each of the $N_{FFT}$-point frames of acoustic data 36', and dividing by the total number of frames $N_{Frame}$, as follows:

$$\overline{P}_A = \frac{\sum_{k=0}^{N_{Frame}-1} P_A(k)}{N_{Frame}}; \quad (12a)$$

$$\overline{P}_B = \frac{\sum_{k=0}^{N_{Frame}-1} P_B(k)}{N_{Frame}}; \quad (12b)$$

$$\overline{P}_C = \frac{\sum_{k=0}^{N_{Frame}-1} P_C(k)}{N_{Frame}}; \text{ and} \quad (12c)$$

$$\overline{P}_D = \frac{\sum_{k=0}^{N_{Frame}-1} P_D(k)}{N_{Frame}}. \quad (12d)$$

Then, if, in step (2604), any of the average spectral power values $\overline{P}_A$, $\overline{P}_B$, $\overline{P}_C$, $\overline{P}_D$ exceeds a first threshold Threshold$_{GOOD}$, and if, in step (2606), each of the average spectral power values $\overline{P}_A$, $\overline{P}_B$, $\overline{P}_C$, $\overline{P}_D$ exceeds a second threshold Threshold$_{BAD}$, then, in step (2608), the associated auscultatory sound-or-vibration sensor 14 is indicated as having passed the test. Otherwise, from either steps (2604) or (2606), in step (2610), the associated auscultatory sound-or-vibration sensor 14 is indicated as having failed the test. The first $Threshold_{GOOD}$ and second $Threshold_{BAD}$ thresholds are derived empirically by testing set of known "good" auscultatory sound-or-vibration sensors 14 with a set of sound generators 146 in a particular configuration (i.e. placement and spacing of the auscultatory sound-or-vibration sensors 14 to sound generators 146), which is then replicated for subsequent arrays 145 of a sound generators 146. For example, in one set of embodiments, the first threshold $Threshold_{GOOD}$ is −35 dB, and the second threshold $Threshold_{BAD}$ is −50 dB.

The auscultatory-sensor integrity-test procedure 2400 is performed both prior to placing the array 18 of auscultatory sound-or-vibration sensors 14 on the thorax 26 of the test subject 12, and after collection of auscultatory sound signals 36 has been completed for a given test of the test subject 12 by the coronary-artery-disease (CAD) detection system 10. The auscultatory-sensor integrity-test procedure 2400 is performed with each auscultatory sound-or-vibration sensors 14 of the array 18 seated in a corresponding well 148 in the docking system 100, 100.1, 100.2, 100.3, abutting a corresponding sound generator 146, 146' of the associated array 145 of sound generators 146, 146'.

Figure 27:
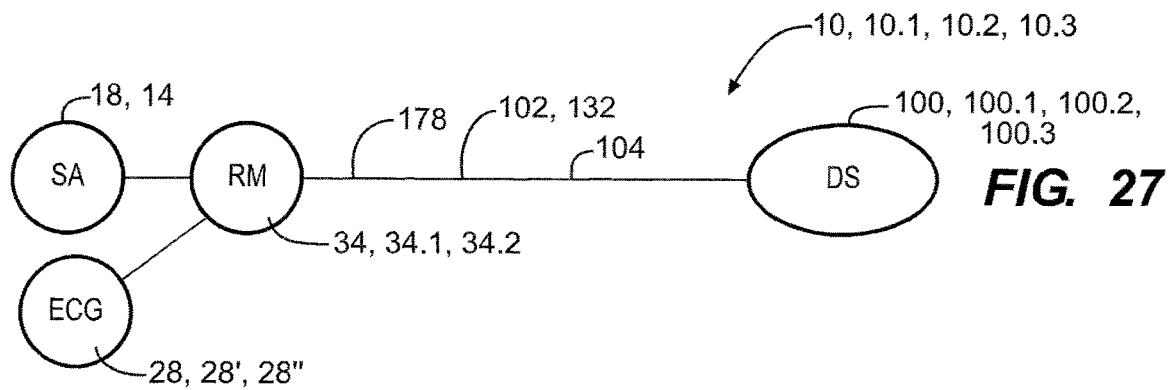
FIG. 27 illustrates a block diagram of communication paths of the coronary-artery-disease detection system illustrated in FIG. 1.

Referring to FIG. 27, the coronary-artery-disease (CAD) detection system 10, 10.1, 10.2 incorporates a bi-directional communication link 178—for example, either or both a wireless interface 102, 132 or a USB interface 104— between the recording module 34, 34.1, 34.2 and the docking system 100, 100.1, 100.2, 100.3, so as to provide for the docking system 100, 100.1, 100.2, 100.3 to cause the recording module 34, 34.1, 34.2 to commence recording auscultatory sound signals 36 from the array 18 of auscultatory sound-or-vibration sensors 14 —and possibly also to commence recording an ECG signal 38 from the ECG sensor 28, 28', 28" or an audio signal 97 from a microphone or background noise sensor 97—and, in some embodiments, to provide for the docking system 100, 100.1, 100.2, 100.3 to control the controllable gain of the controllable-gain amplifier 46, 46.1, 46.2, 46.3 in the recording module 34, 34.1, 34.2. The communication link 178 between the recording module 34, 34.1, 34.2 and the docking system 100, 100.1, 100.2, 100.3 also provides for the recording module 34, 34.1, 34.2 to transmit associated real-time status information, and to transmit the recorded auscultatory sound signals 36, and possibly also the recorded ECG signal 38 or the recorded audio signal 97', therefrom, to the docking system 100, 100.1, 100.2, 100.3 for subsequent processing and display. For example, in accordance with various embodiments, the wireless interface 102,132 may utilize either WIFI or Bluetooth® protocols and associated hardware.

Figure 28:
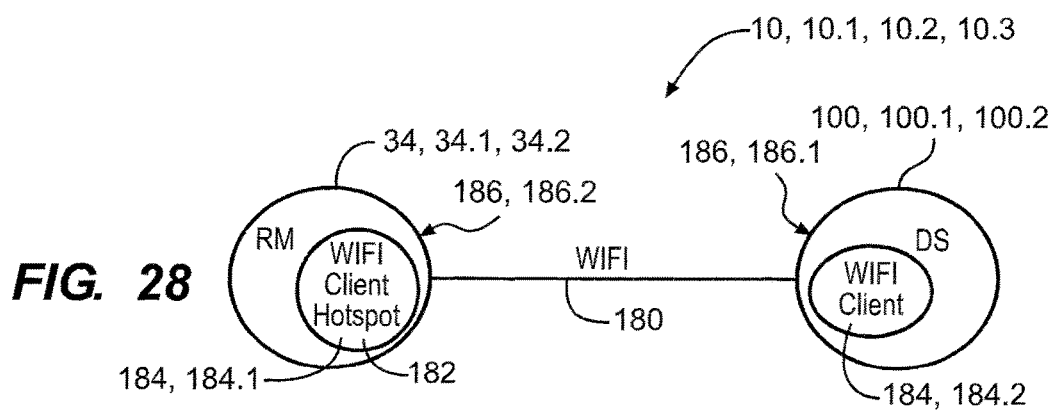
FIG. 28 illustrates a WIFI communication link between the recording module and the docking system of the coronary-artery-disease detection system illustrated in FIG. 1, with the hotspot in the recording module.
Figure 29:
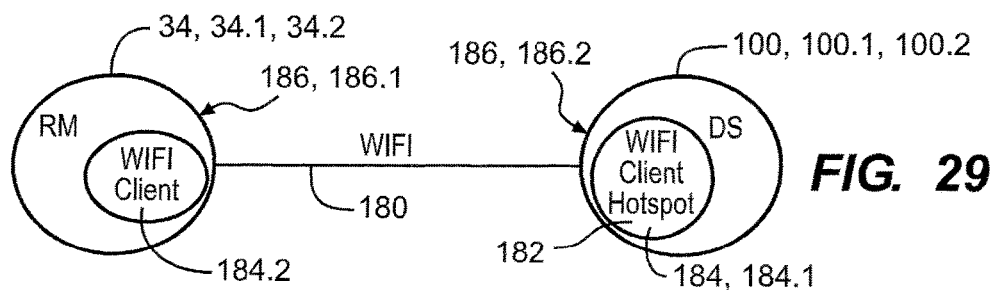
FIG. 29 illustrates a WIFI communication link between the recording module and the docking system of the coronary-artery-disease detection system illustrated in FIG. 1, with the hotspot in the docking system.
Figure 30:
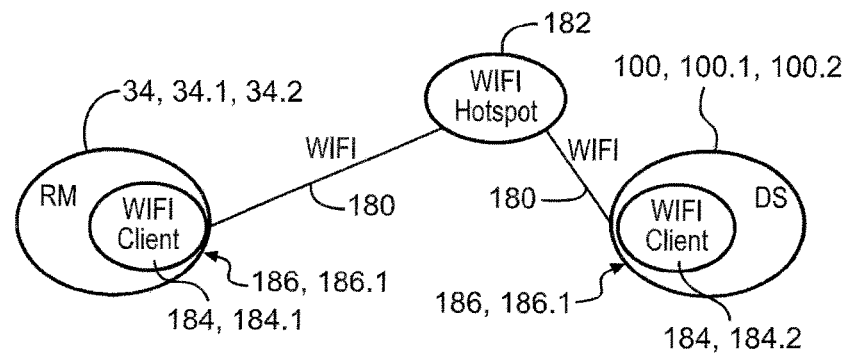
FIG. 30 illustrates a WIFI communication link between the recording module and the docking system of the coronary-artery-disease detection system illustrated in FIG. 1, with the hotspot external of both the recording module and the docking system.

Referring to FIGS. 28-30, a WIFI communication link 180 controlled by a WIFI hotspot 182 in communication with a pair of WIFI clients 184, 184.1, 184.2 provides for the WIFI clients 184.1, 184.2 to communicate with one another via the WIFI hotspot 182, for example, over the ISM band of frequencies, for example, in one set of embodiments, at 2.4 GHz, for example, either using antennas embedded in one or more of the recording module 34, 34.1, 34.2 and the docking system 100, 100.1, 100.2, or using one or more external antennas, for example, one or more monopole antennas. Each of the recording module 34, 34.1, 34.2 and the docking system 100, 100.1, 100.2 incorporates one of two aspects 186.1, 186.2 of an associated WIFI adapter 186, i.e. either a first aspect 186.1 of which is configured as just a WIFI client 184, or a second aspect 186.2 of which is configured as both a and WIFI hotspot 182 a WIFI client 184. For example, referring to FIG. 28, the WIFI adapter 186, 186.2 in the recording module 34, 34.1, 34.2 is configured as both a first WIFI client 184, 184.1 and the WIFI hotspot 182, and the WIFI adapter 186, 186.1 in the docking system 100, 100.1, 100.2 is configured as just a second WIFI client 184, 184.2. Alternatively, referring to FIG. 29, the WIFI adapter 186, 186.2 in the docking system 100, 100.1, 100.2 is configured as both the first WIFI client 184, 184.1 and the WIFI hotspot 182, and the WIFI adapter 186, 186.1 in the recording module 34, 34.1, 34.2 is configured as just the second WIFI client 184, 184.2. Yet further alternatively, referring to FIG. 30, the WIFI hotspot 182 is external of both the recording module 34, 34.1, 34.2 and the docking system 100, 100.1, 100.2, wherein the WIFI adapter 186, 186.1 in the recording module 34, 34.1, 34.2 is configured as just the first WIFI client 184, 184.1 and the WIFI adapter 186, 186.1 in the docking system 100, 100.1, 100.2 is configured as just the second WIFI client 184, 184.2. In each of the above configurations illustrated in FIGS. 28-30, each of WIFI clients 184, 184.1, 184.2 is in communication with the WIFI hotspot 182 that provides for communicating data, status and control information therethrough.

In accordance with a first aspect, all of the data communicated between the recording module 34, 34.1, 34.2 and the docking system 100, 100.1, 100.2 is via the WIFI communication link 180.

Figure 31:
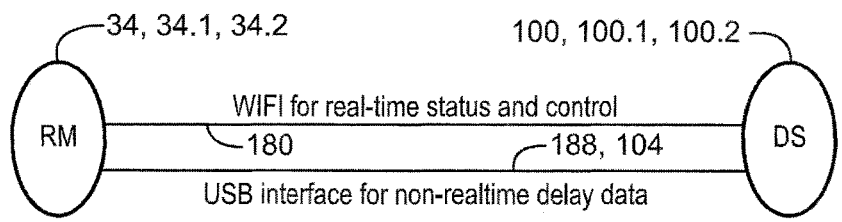
FIG. 31 illustrates a block diagram of dual-path communications between the recording module and the docking system of the coronary-artery-disease detection system illustrated in FIG. 1, with a WIFI path for real-time status and control, and a USB path for transferring data acquired by the associated auscultatory sound sensors.

Alternatively, referring to FIG. 31, in accordance with a second aspect, a physical, USB communication link 188, 104 is used to communicate non-real-time data—for example, recorded auscultatory sound signals 36, or a recorded ECG signal 38, stored in memory 106 on the recording module 34, 34.1, 34.2 during the associated data collection process—from the recording module 34, 34.1, 34.2 to the docking system 100, 100.1, 100.2 following the data collection process, wherein the remaining status and control information is communicated wirelessly between the recording module 34, 34.1, 34.2 and the docking system 100, 100.1, 100.2 via the WIFI communication link 180, resulting in a substantially reduced overall demand on the capacity or resources of the WIFI communication link 180. For example, in some cases, other devices using the same WIFI channel may cause unacceptable delays in wireless communication between the recording module 34, 34.1, 34.2 and the docking system 100, 100.1, 100.2 when communicating over the WIFI communication link 18.

Figure 32:
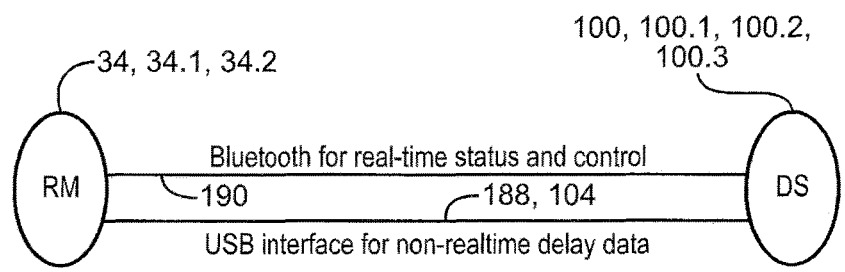
FIG. 32 illustrates a block diagram of dual-path communications between the recording module and the docking system of the coronary-artery-disease detection system illustrated in FIG. 1, with a Bluetooth path for real-time status and control, and a USB path for transferring data acquired by the associated auscultatory sound sensors.
Figure 33:
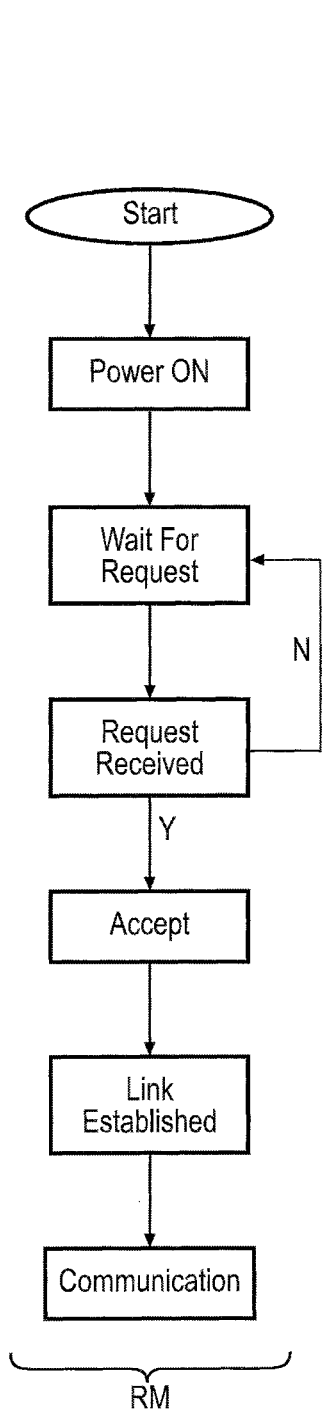
FIG. 33 illustrates a flowchart of a process implemented on the recording module, for establishing and using a link for Bluetooth communications.
Figure 34:
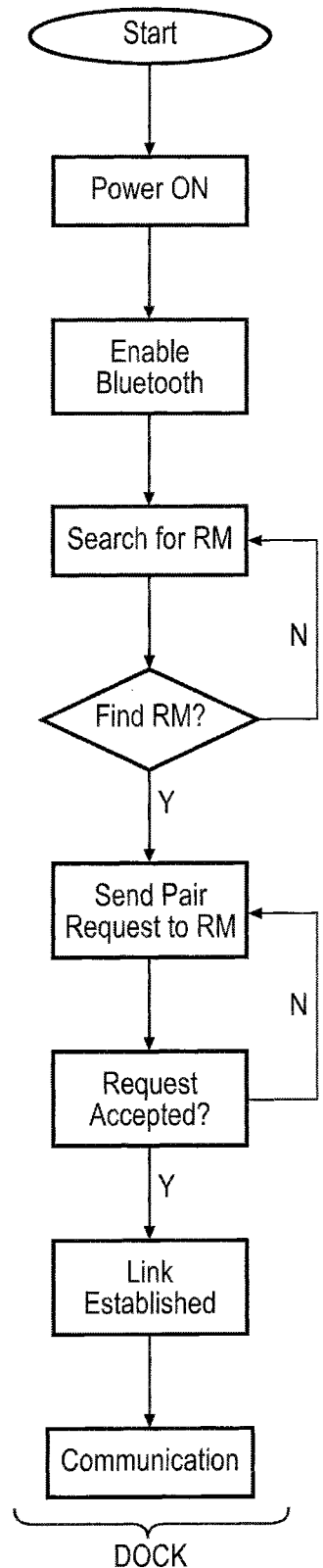
FIG. 34 illustrates a flowchart of a process implemented on the docking system, for establishing and using a link for Bluetooth communications.

Yet further alternatively, referring to FIG. 32, in accordance with a third aspect, a physical, USB communication link 188, 104 is used to communicate non-real-time data— for example, recorded auscultatory sound signals 36, or a recorded ECG signal 38, stored in memory 106 on the recording module 34, 34.1, 34.2 during the associated data collection process—from the recording module 34, 34.1, 34.2 to the docking system 100, 100.1, 100.2, 100.3 following the data collection process, and the remaining status and control information is communicated wirelessly between the recording module 34, 34.1, 34.2 and the docking system 100, 100.1, 100.2, 100.3 via a peer-to-peer Bluetooth® communication link 190, the latter of which would typically not have sufficient capacity to handle communication of the auscultatory sound signals 36, or an ECG signal 38 in real time, but which would have the capacity to handle communication of the associated real-time data. For example, FIGS. 33 and 34 respectively illustrate processes on the recording module 34, 34.1, 34.2 and the docking system 100, 100.1, 100.2, 100.3, respectively, for establishing a peer-to-peer Bluetooth® communication link 190 therebetween.

Figure 35:
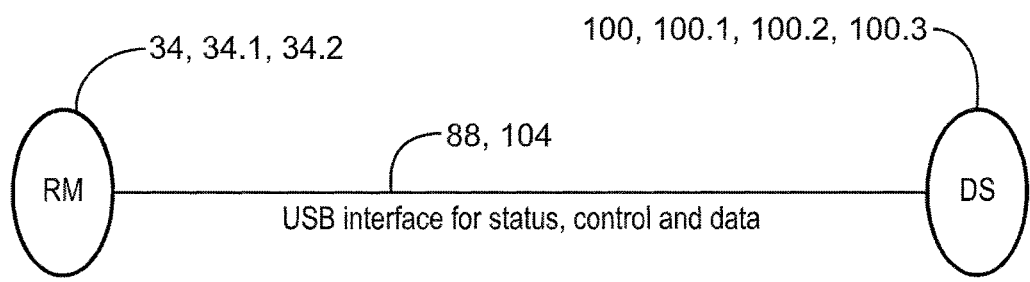
FIG. 35 illustrates a block diagram of single-path, USB-based communications between the recording module and the docking system of the coronary-artery-disease detection system illustrated in FIG. 1 for transferring data acquired by the associated auscultatory sound sensors from the recording module to the associated docking system.

Yet further alternatively, referring to FIG. 35, in accordance with a fourth aspect, a physical, USB communication link 188, 104 is used exclusively to communicate all data between the recording module 34, 34.1, 34.2 and the docking system 100, 100.1, 100.2, 100.3, thereby precluding interference from external wireless signals, and providing for the recording module 34, 34.1, 34.2 to be powered directly from the docking system 100, 100.1, 100.2, 100.3, thereby precluding the need for a battery 110, 110' and associated charging and battery-power-management system in the recording module 34, 34.1, 34.2.

Figure 36:
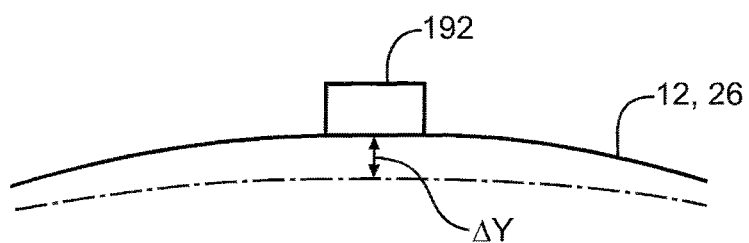
FIG. 36 illustrates an accelerometer on the thorax of a test-subject during a respiration cycle of the test-subject.

Referring to FIGS. 1 and 36 the coronary-artery-disease (CAD) detection system 10 may further incorporate an accelerometer 192 operatively coupled to the thorax 26 of the test-subject 12 to provide an associated acceleration signal responsive to the motion of the thorax 26. With the test-subject 12 lying on their back, inclined at an angle θ, for example, as illustrated in FIG. 3, the associated acceleration signal operatively coupled to recording module 34, 34.1, 34.2, and processed by a corresponding signal preprocessing channel 40, 40.9 thereof—for example, in one set of embodiments, similar to that used for a second aspect, active auscultatory sound-or-vibration sensor 14, 14",—may be twice integrated either in recording module 34, 34.1, 34.2 or the docking system 100, 100.1, 100.2, 100.3 to generate a measure of the peak-to-peak displacement ΔY of the thorax 26, which if greater than a threshold would be indicative of breathing by the test-subject 12.

Figure 37A:
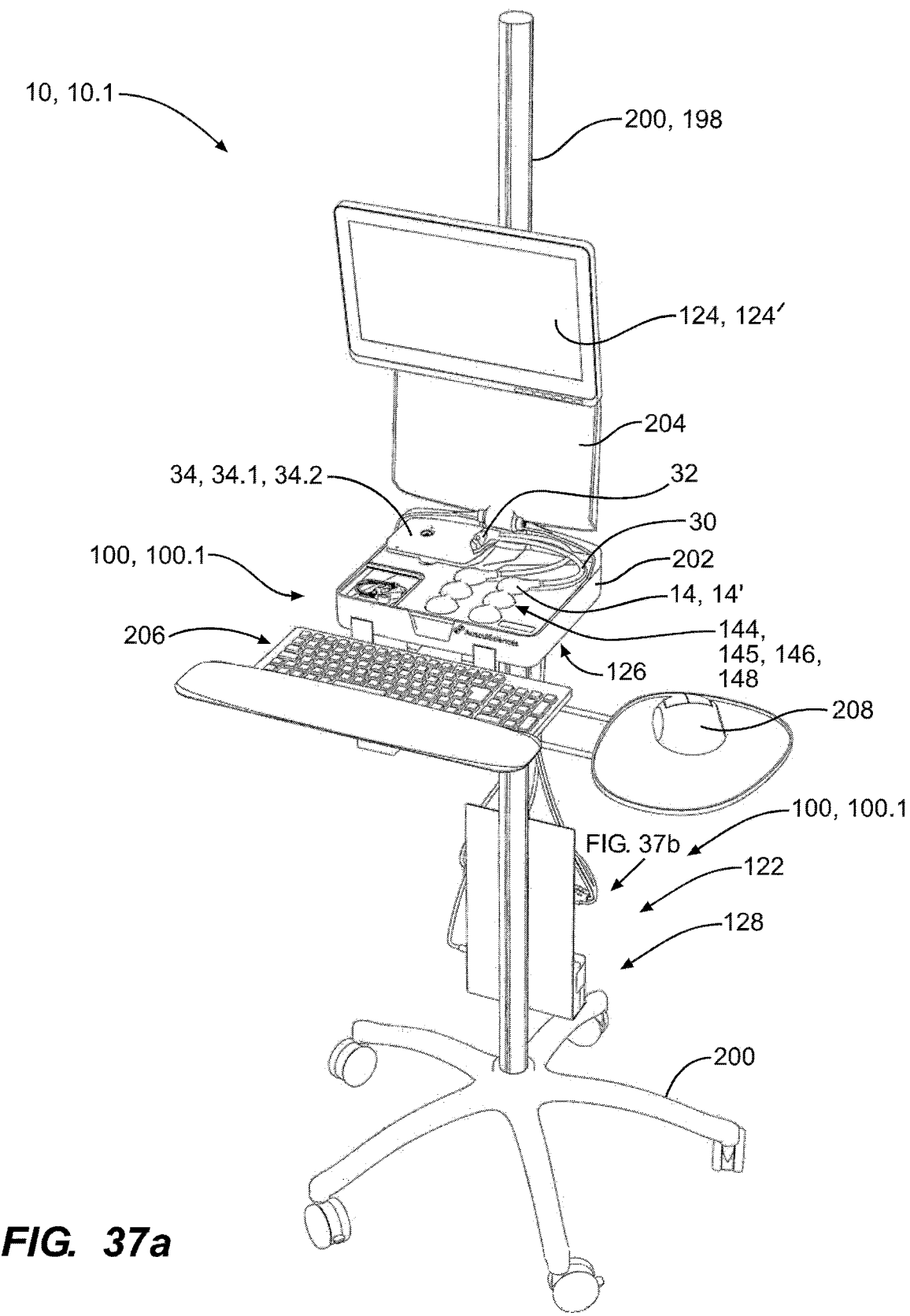
FIG. 37a illustrates an overall perspective view an embodiment of the first aspect of a coronary artery disease detection system, configured as a mobile, roll-around workstation.
Figure 37B:
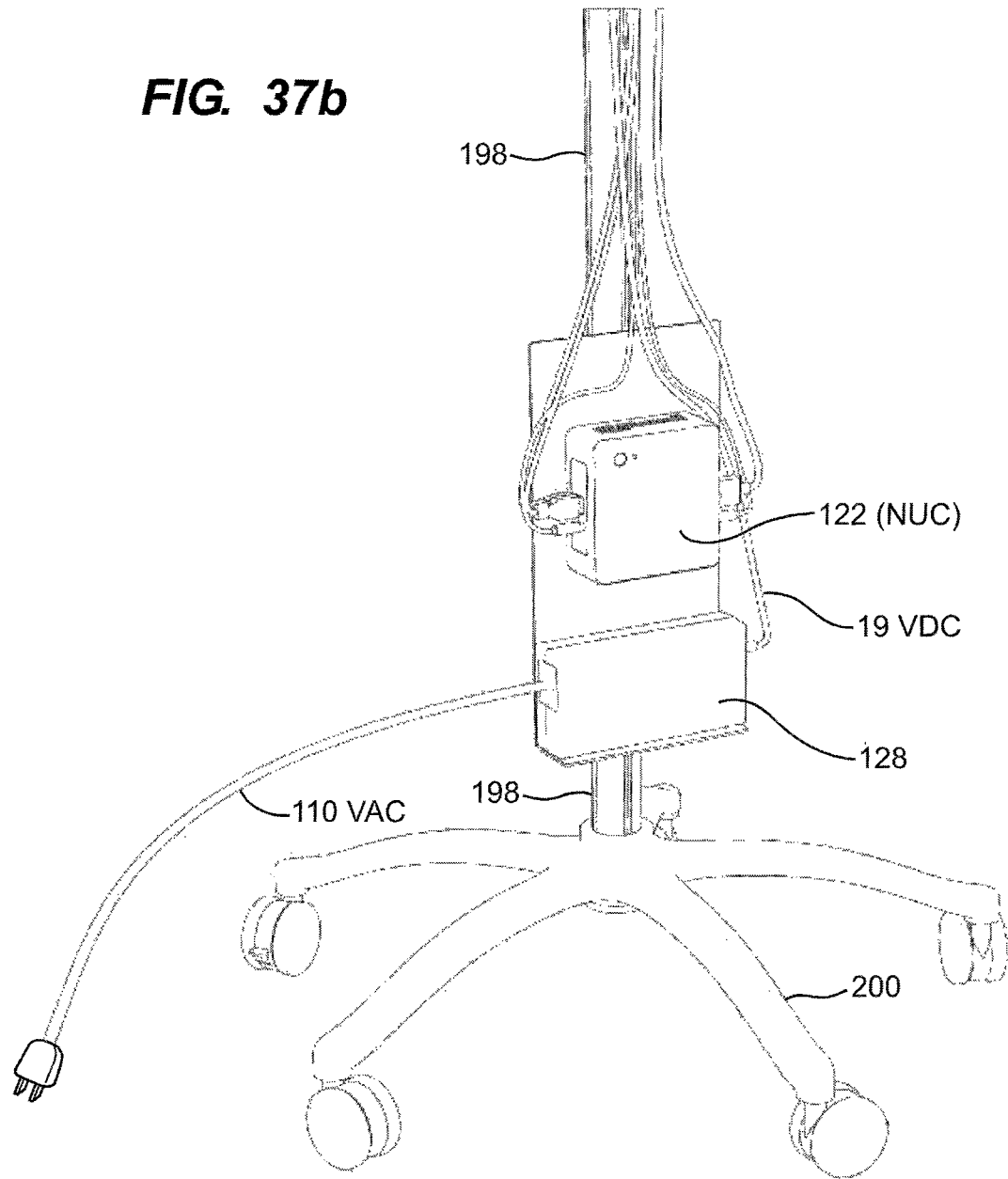
FIG. 37b illustrates a fragmentary perspective view of a lower portion of the embodiment of the first aspect of a coronary artery disease detection system illustrated in FIG. 37a, illustrating the associated embedded computer system and AC power adapter.

Referring to FIGS. 37a and 37b, an embodiment of the first aspect coronary-artery-disease (CAD) detection system 10, 10.1 is configured as a mobile, roll-around workstation, wherein the associated embedded computer system 122 (e.g. a Windows-based Intel NUC computer) and AC-powered AC/DC power adapter 128 are attached near the base of a post 198 that depends from a mobile instrument stand 200. The associated sound generators 146 and wells 148 of the sensor-integrity-test sub-system 144 of the docking system 100, 100.1 incorporated in a top, inner surface of a housing 202, the latter of which is located on a work surface depending from the post 198 at a comfortable working height for the operator. The housing 202 provides for convenient storage of the recording module 34, 34.1, 34.2, associated auscultatory sound-or-vibration sensors 14, 14', 14", and associated supplies, and incorporates a hinged cover 204 to provide for protecting the contents therein, and also houses the associated power-management board 126, the latter of which is operatively coupled to and receives power from the AC-powered AC/DC power adapter 128. A keyboard 206 and mouse 208 are provided on associated work surfaces to facilitate operator input to the docking system 100, 100.1. For example, in one set of embodiments, an Intel NUC embedded computer system 122 provides for a Windows-based computing environment. Either an LCD touch-screen display 124, or a conventional display 124', is supported from the post 198 at a comfortable eye height of the operator, the latter being sufficient in view of the keyboard 206 and mouse 208 being available for operator input in cooperation with the Windows-based Intel NUC computer of the embedded computer system 122.

Figure 38:
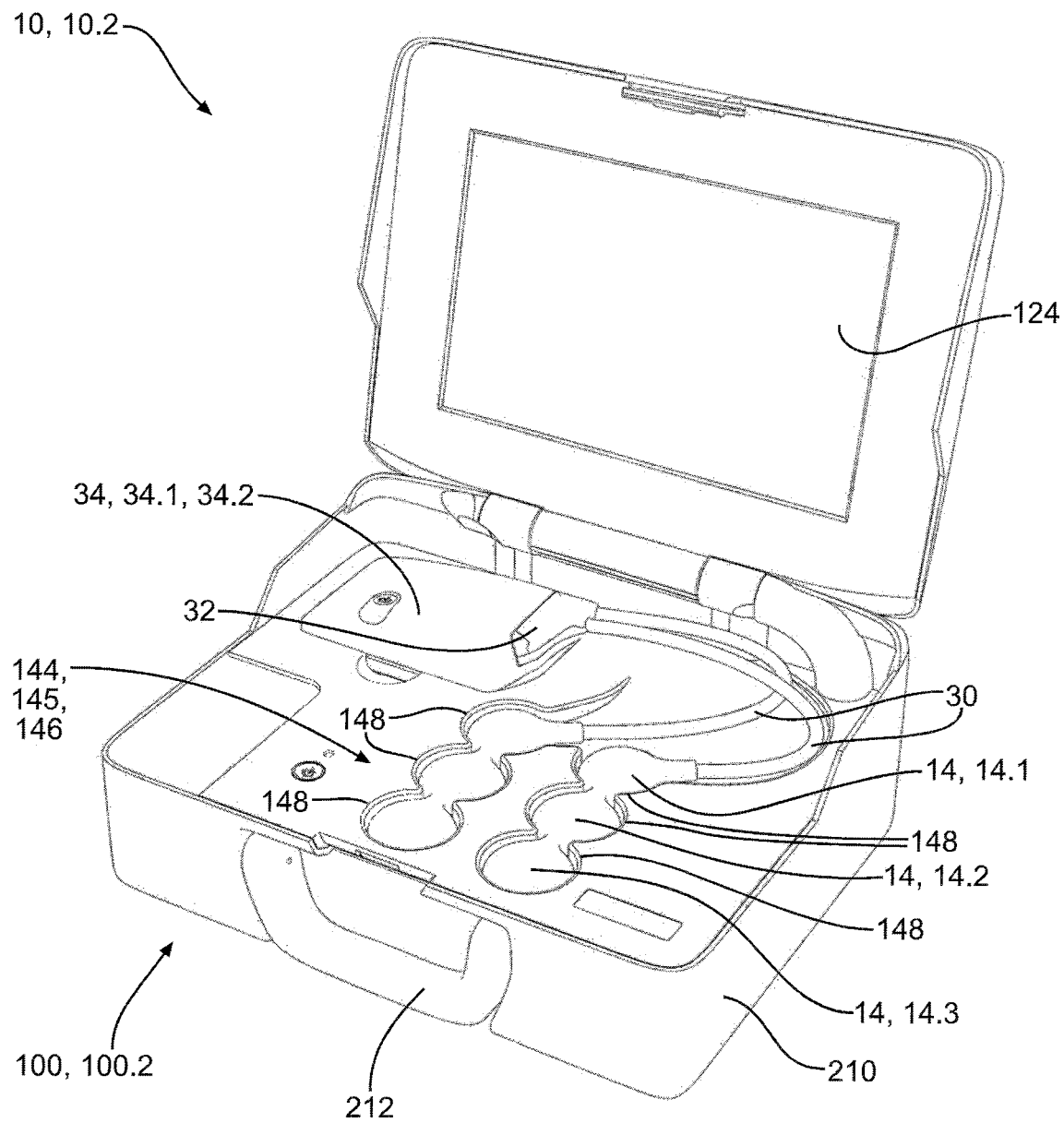
FIG. 38 illustrates a perspective view an embodiment of the second aspect of a coronary artery disease detection system, configured as a portable, self-contained device.

Referring to FIG. 38, an embodiment of the second aspect coronary-artery-disease (CAD) detection system 10, 10.2 is configured as a portable, self-contained device, with all the associated components of the associated docking system 100, 100.2 enclosed in an associated housing 210 that is adapted with a handle 212 for carrying, with the associated sound generators 146 and wells 148 of the sensor-integrity-test sub-system 144 of the associated docking system 100, 100.2 incorporated in an top, inner surface the housing 210, the latter of which also provides for convenient storage of the recording module 34, 34.1, 34.2, associated auscultatory sound-or-vibration sensors 14, 14', 14", and associated supplies, and utilizes the associated LCD touch-screen display 124 as a hinged cover to provide for protecting the contents therein.

Figure 39:
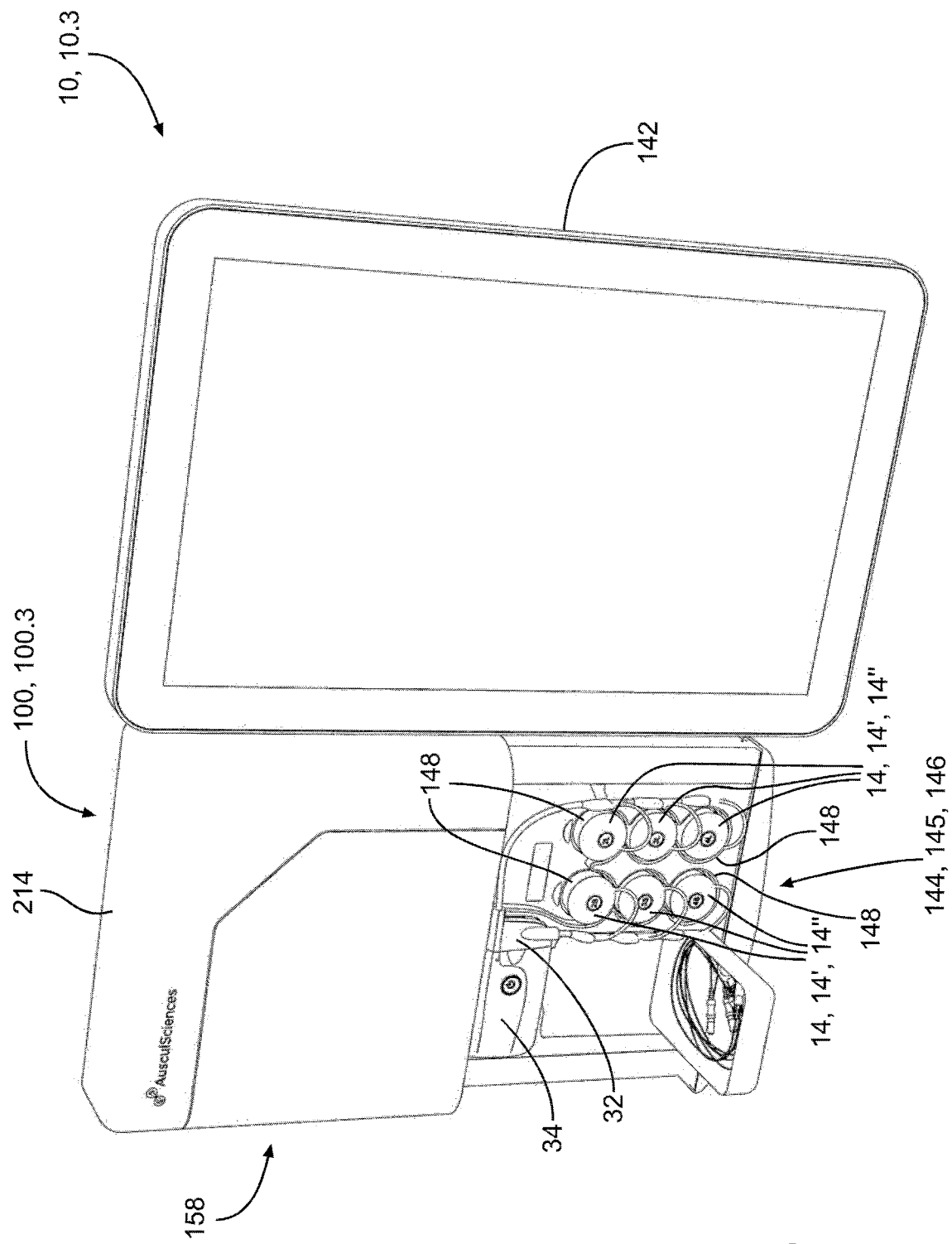
FIG. 39 illustrates a perspective view an embodiment of the third aspect of a coronary artery disease detection system, configured as a wall-mounted system.

Referring to FIG. 39, an embodiment of the third aspect coronary-artery-disease (CAD) detection system 10, 10.3 is configured as a wall-mounted system, with the associated wall-mounted panel PC 142 providing for both display and touch-screen-initiated control, and with the associated audio signal generator card 158 and sensor-integrity-test sub-system 144 of the associated docking system 100, 100.1 incorporated in an associated housing 214 that also provides for convenient storage of the recording module 34, 34.1, 34.2, associated auscultatory sound-or-vibration sensors 14, 14', 14", and associated supplies, wherein the housing 214 may be either wall mounted or portable, and in the latter case, possibly wall stowed when not in use. If wall mounted, the associated wells 148 in the housing 214 are adapted—for example, with a friction fit—to provide for retaining the associated auscultatory sound-or-vibration sensors 14, 14', 14" therein during an integrity test thereof.

A method of receiving and processing at least one auscultatory sound signal from a corresponding at least one auscultatory sound-or-vibration sensor may comprise: Step a: placing the corresponding at least one auscultatory sound-or-vibration sensor in proximity to a corresponding sound generator; Step b: applying an auscultatory sound-or-vibration sensor electronic test signal to the corresponding sound generator, wherein the auscultatory sound-or-vibration sensor electronic test signal comprises a plurality of frequency components, each frequency component of the plurality of frequency components comprises an integral number of wavelengths, and each the frequency component is deterministically terminated following a duration of time corresponding to the integral number of wavelengths of the frequency component after the frequency component of the auscultatory sound-or-vibration sensor electronic test signal is applied to the corresponding sound generator; Step c: generating an acoustic sound signal from the corresponding sound generator responsive to the auscultatory sound-or-vibration sensor electronic test signal; Step d: exposing the corresponding at least one auscultatory sound-or-vibration sensor to the acoustic sound signal and receiving a corresponding at least one auscultatory sound signal responsive thereto; and Step e: determining whether or not the corresponding at least one auscultatory sound-or-vibration sensor is functioning properly responsive to an analysis of a Fourier Transform of the corresponding at least one auscultatory sound signal. The operation of determining whether or not the corresponding at least one auscultatory sound-or-vibration sensor is functioning properly may further comprise: a) capturing the corresponding at least one auscultatory sound signal over a period of time; b) calculating a Short Time Fourier Transform (STFT) for each of a plurality of windows of data within the period of time; and c) calculating a corresponding average power corresponding to each of the plurality of frequency components from each of the plurality of windows of data, wherein the determination of whether or not the corresponding at least one auscultatory sound-or-vibration sensor is functioning properly may be responsive to a comparison of the corresponding average power corresponding to each of the plurality of frequency components with at least one corresponding threshold. The corresponding at least one auscultatory sound signal from the corresponding at least one auscultatory sound-or-vibration sensor may be received while the corresponding at least one auscultatory sound-or-vibration sensor is operatively coupled to a test subject, and the method may further comprise concurrently receiving an electrographic signal generated by an ECG sensor operatively coupled to the test subject; wherein the corresponding at least one auscultatory sound signal from the corresponding at least one auscultatory sound-or-vibration sensor may be received following the completion of Steps a-e for the corresponding at least one auscultatory sound-or-vibration sensor. The corresponding at least one auscultatory sound signal from the corresponding at least one auscultatory sound-or-vibration sensor may be received while the corresponding at least one auscultatory sound-or-vibration sensor is operatively coupled to a test subject, and the method may further comprise concurrently receiving a background sound signal generated by a microphone in a same room as the test subject; wherein the corresponding at least one auscultatory sound signal from the corresponding at least one auscultatory sound-or-vibration sensor may be received following the completion of Steps a-e for the corresponding at least one auscultatory sound-or-vibration sensor. The corresponding at least one auscultatory sound signal from the corresponding at least one auscultatory sound-or-vibration sensor may be received while the corresponding at least one auscultatory sound-or-vibration sensor is operatively coupled to a test subject, and the method nay further comprise concurrently receiving an electronic acceleration signal generated by an accelerometer operatively coupled to the test subject. wherein the corresponding at least one auscultatory sound signal from the corresponding at least one auscultatory sound-or-vibration sensor may be received following the completion of Steps a-e for the corresponding at least one auscultatory sound-or-vibration sensor. The method of receiving and processing at least one auscultatory sound signal from a corresponding at least one auscultatory sound-or-vibration sensor may further comprise analyzing the corresponding at least one auscultatory sound signal from the corresponding at least one auscultatory sound-or-vibration sensor operatively coupled to the test subject to determine an associated gain value for a signal-processing channel associated with the corresponding at least one auscultatory sound-or-vibration sensor, and communicating a control signal to a recording module to which the corresponding at least one auscultatory sound-or-vibration sensor is operatively coupled so as to provide for the recording module to subsequently control a gain of an amplifier associated with the signal-processing channel responsive to the associated gain value. The corresponding at least one auscultatory sound-or-vibration sensor may be one of a plurality of sound-or-vibration sensors, each auscultatory sound-or-vibration sensor of the plurality of sound-or-vibration sensors may be placed in proximity to the corresponding sound generator of a plurality of sound generators; and each the corresponding sound generator of the plurality of sound generators may have a frequency response within a range of +/−5 dB of a median frequency response of the plurality of sound generators over a frequency range of 0 to 2 kHz; wherein each the auscultatory sound-or-vibration sensor of the plurality of sound-or-vibration sensors may be tested concurrently, and the auscultatory sound-or-vibration sensor electronic test signal may be applied concurrently to each the corresponding sound generator of the plurality of sound generators. Each the corresponding at least one auscultatory sound-or-vibration sensor may be associated with a recording module that provides for recording each the corresponding at least one auscultatory sound signal, and the method may further comprise transmitting each the corresponding at least one auscultatory sound signal from the recording module to a docking system that generates the auscultatory sound-or-vibration sensor electronic test signal and determines whether or not the corresponding at least one auscultatory sound-or-vibration sensor is functioning properly responsive to the analysis of the Fourier Transform of the corresponding at least one auscultatory sound signal; wherein each the corresponding at least one auscultatory sound-or-vibration sensor may be operatively coupled to the recording module with a wired connection; or the recording module may be operatively coupled to the docking system with a wired connection; or the recording module may be operatively coupled to the docking system with a wireless connection. The operation of applying the auscultatory sound-or-vibration sensor electronic test signal to the corresponding sound generator may comprise driving the corresponding sound generator with, or responsive to, an audio CODEC; wherein the audio CODEC may be driven by a digital signal responsive to a stored test signal. The operation of applying the auscultatory sound-or-vibration sensor electronic test signal to the corresponding sound generator may comprise driving the corresponding sound generator with, or responsive to, an analog signal from a digital-to-analog converter responsive to a digital waveform signal; wherein the digital waveform signal may be stored in, and recalled from, memory; or the digital waveform signal may be generated in real time responsive to a stored program.

A method of receiving and processing at least one auscultatory sound signal from a corresponding at least one auscultatory sound-or-vibration sensor, may comprise: a) placing the corresponding at least one auscultatory sound-or-vibration sensor in proximity to a corresponding sound generator; b) applying an auscultatory sound-or-vibration sensor electronic test signal to the corresponding sound generator, wherein the auscultatory sound-or-vibration sensor electronic test signal comprises a plurality of frequency components, each frequency component of the plurality of frequency components comprises an integral number of wavelengths, and each the frequency component is terminated following a duration of time corresponding to the integral number of wavelengths of the frequency component after the frequency component of the auscultatory sound-or-vibration sensor electronic test signal is applied to the corresponding sound generator, wherein the operation of applying the auscultatory sound-or-vibration sensor electronic test signal to the corresponding sound generator comprises driving the corresponding sound generator with, or responsive to, an analog signal from a digital-to-analog converter responsive to a digital waveform signal, wherein the digital waveform signal is generated in real time responsive to a stored program, wherein the digital waveform signal is generated in real time responsive to a plurality of STFT frame-synchronized sinusoidal test frequencies and a number of points of an associated Short Time Fourier Transform (STFT), wherein each STFT frame-synchronized sinusoidal test frequency of the plurality of STFT frame-synchronized sinusoidal test frequencies has a corresponding integral number of wavelengths within a time-frame interval of the associated Short Time Fourier Transform (STFT), and the STFT frame-synchronized sinusoidal test frequency is an integer factor times a ratio of a sampling frequency divided by the number of points of the associated Short Time Fourier Transform (STFT); c) generating an acoustic sound signal from the corresponding sound generator responsive to the auscultatory sound-or-vibration sensor electronic test signal; d) exposing the corresponding at least one auscultatory sound-or-vibration sensor to the acoustic sound signal and receiving a corresponding at least one auscultatory sound signal responsive thereto; and e) determining whether or not the corresponding at least one auscultatory sound-or-vibration sensor is functioning properly responsive to an analysis of a Fourier Transform of the corresponding at least one auscultatory sound signal.

While specific embodiments have been described in detail in the foregoing detailed description and illustrated in the accompanying drawings, those with ordinary skill in the art will appreciate that various modifications and alternatives to those details could be developed in light of the overall teachings of the disclosure. It should be understood, that any reference herein to the term "or" is intended to mean an "inclusive or" or what is also known as a "logical OR", wherein when used as a logic statement, the expression "A or B" is true if either A or B is true, or if both A and B are true, and when used as a list of elements, the expression "A, B or C" is intended to include all combinations of the elements recited in the expression, for example, any of the elements selected from the group consisting of A, B, C, (A, B), (A, C), (B, C), and (A, B, C); and so on if additional elements are listed. Furthermore, it should also be understood that the indefinite articles "a" or "an", and the corresponding associated definite articles "the" or "said", are each intended to mean one or more unless otherwise stated, implied, or physically impossible. Yet further, it should be understood that the expressions "at least one of A and B, etc.", "at least one of A or B, etc.", "selected from A and B, etc." and "selected from A or B, etc." are each intended to mean either any recited element individually or any combination of two or more elements, for example, any of the elements from the group consisting of "A", "B", and "A AND B together", etc. Yet further, it should be understood that the expressions "one of A and B, etc." and "one of A or B, etc." are each intended to mean any of the recited elements individually alone, for example, either A alone or B alone, etc., but not A AND B together. Furthermore, it should also be understood that unless indicated otherwise or unless physically impossible, that the above-described embodiments and aspects can be used in combination with one another and are not mutually exclusive. Accordingly, the particular arrangements disclosed are meant to be illustrative only and not limiting as to the scope of the invention, which is to be given the full breadth of the appended claims, and any and all equivalents thereof.

What is claimed is:

1. A method of receiving and processing at least one auscultatory sound signal from a corresponding at least one auscultatory sound-or-vibration sensor, comprising:
   a. placing the corresponding at least one auscultatory sound-or-vibration sensor in proximity to a corresponding sound generator;
   b. applying an auscultatory sound-or-vibration sensor electronic test signal to said corresponding sound generator, wherein said auscultatory sound-or-vibration sensor electronic test signal comprises a plurality of frequency components, each frequency component of said plurality of frequency components comprises an integral number of wavelengths, and each said frequency component is deterministically terminated following a duration of time corresponding to said integral number of wavelengths of said frequency component after said frequency component of said auscultatory sound-or-vibration sensor electronic test signal is applied to said corresponding sound generator;
   c. generating an acoustic sound signal from said corresponding sound generator responsive to said auscultatory sound-or-vibration sensor electronic test signal;
   d. exposing said corresponding at least one auscultatory sound-or-vibration sensor to said acoustic sound signal and receiving a corresponding at least one auscultatory sound signal responsive thereto; and
   e. determining whether or not said corresponding at least one auscultatory sound-or-vibration sensor is functioning properly responsive to an analysis of a Fourier Transform of said corresponding at least one auscultatory sound signal.

2. A method of receiving and processing at least one auscultatory sound signal from a corresponding at least one auscultatory sound-or-vibration sensor as recited in claim 1, wherein the operation of determining whether or not said corresponding at least one auscultatory sound-or-vibration sensor is functioning properly comprises:
   a. capturing said corresponding at least one auscultatory sound signal over a period of time;
   b. calculating a Short Time Fourier Transform (STFT) for each of a plurality of windows of data within said period of time; and
   c. calculating a corresponding average power corresponding to each of said plurality of frequency components from each of said plurality of windows of data, wherein the determination of whether or not said corresponding at least one auscultatory sound-or-vibration sensor is functioning properly is responsive to a comparison of said corresponding average power corresponding to each of said plurality of frequency components with at least one corresponding threshold.

3. A method of receiving and processing at least one auscultatory sound signal from a corresponding at least one auscultatory sound-or-vibration sensor as recited in claim 1, wherein said corresponding at least one auscultatory sound signal from said corresponding at least one auscultatory sound-or-vibration sensor is received while said corresponding at least one auscultatory sound-or-vibration sensor is operatively coupled to a test subject, further comprising concurrently receiving an electrographic signal generated by an ECG sensor operatively coupled to said test subject.

4. A method of receiving and processing at least one auscultatory sound signal from a corresponding at least one auscultatory sound-or-vibration sensor as recited in claim 1, wherein said corresponding at least one auscultatory sound signal from said corresponding at least one auscultatory sound-or-vibration sensor is received while said corresponding at least one auscultatory sound-or-vibration sensor is operatively coupled to a test subject, further comprising concurrently receiving a background sound signal generated by a microphone in a same room as said test subject.

5. A method of receiving and processing at least one auscultatory sound signal from a corresponding at least one auscultatory sound-or-vibration sensor as recited in claim 1, wherein said corresponding at least one auscultatory sound signal from said corresponding at least one auscultatory sound-or-vibration sensor is received while said corresponding at least one auscultatory sound-or-vibration sensor is operatively coupled to a test subject, further comprising concurrently receiving an electronic acceleration signal generated by an accelerometer operatively coupled to said test subject.

6. A method of receiving and processing at least one auscultatory sound signal from a corresponding at least one auscultatory sound-or-vibration sensor as recited in claim 1, further comprising analyzing said corresponding at least one auscultatory sound signal from said corresponding at least one auscultatory sound-or-vibration sensor operatively coupled to said test subject to determine an associated gain value for a signal-processing channel associated with said corresponding at least one auscultatory sound-or-vibration sensor, and communicating a control signal to a recording module to which said corresponding at least one auscultatory sound-or-vibration sensor is operatively coupled so as to provide for said recording module to subsequently control a gain of an amplifier associated with said signal-processing channel responsive to said associated gain value.

7. A method of receiving and processing at least one auscultatory sound signal from a corresponding at least one auscultatory sound-or-vibration sensor as recited in claim 1, wherein said corresponding at least one auscultatory sound-or-vibration sensor is one of a plurality of sound-or-vibration sensors, each auscultatory sound-or-vibration sensor of said plurality of sound-or-vibration sensors is placed in proximity to said corresponding sound generator of a plurality of sound generators; and each said corresponding sound generator of said plurality of sound generators has a frequency response within a range of +/−5 dB of a median frequency response of said plurality of sound generators over a frequency range of 0 to 2 kHz.

8. A method of receiving and processing at least one auscultatory sound signal from a corresponding at least one auscultatory sound-or-vibration sensor as recited in claim 7, wherein each said auscultatory sound-or-vibration sensor of said plurality of sound-or-vibration sensors is tested concurrently, and said auscultatory sound-or-vibration sensor electronic test signal is applied concurrently to each said corresponding sound generator of said plurality of sound generators.

9. A method of receiving and processing at least one auscultatory sound signal from a corresponding at least one auscultatory sound-or-vibration sensor as recited in claim 1, wherein each said corresponding at least one auscultatory sound-or-vibration sensor is associated with a recording module that provides for recording each said corresponding at least one auscultatory sound signal, further comprising transmitting each said corresponding at least one auscultatory sound signal from said recording module to a docking system that generates said auscultatory sound-or-vibration sensor electronic test signal and determines whether or not said corresponding at least one auscultatory sound-or-vibration sensor is functioning properly responsive to said analysis of said Fourier Transform of said corresponding at least one auscultatory sound signal.

10. A method of receiving and processing at least one auscultatory sound signal from a corresponding at least one auscultatory sound-or-vibration sensor as recited in claim 9, wherein each said corresponding at least one auscultatory sound-or-vibration sensor is operatively coupled to said recording module with a wired connection.

11. A method of receiving and processing at least one auscultatory sound signal from a corresponding at least one auscultatory sound-or-vibration sensor as recited in claim 9, wherein said recording module is operatively coupled to said docking system with a wired connection.

12. A method of receiving and processing at least one auscultatory sound signal from a corresponding at least one auscultatory sound-or-vibration sensor as recited in claim 9, wherein said recording module is operatively coupled to said docking system with a wireless connection.

13. A method of receiving and processing at least one auscultatory sound signal from a corresponding at least one auscultatory sound-or-vibration sensor as recited in claim 1, wherein the operation of applying said auscultatory sound-or-vibration sensor electronic test signal to said corresponding sound generator comprises driving said corresponding sound generator with, or responsive to, an audio CODEC.

14. A method of receiving and processing at least one auscultatory sound signal from a corresponding at least one auscultatory sound-or-vibration sensor as recited in claim 13, wherein said audio CODEC is driven by a digital signal responsive to a stored test signal.

15. A method of receiving and processing at least one auscultatory sound signal from a corresponding at least one auscultatory sound-or-vibration sensor as recited in claim 1, wherein the operation of applying said auscultatory sound-or-vibration sensor electronic test signal to said corresponding sound generator comprises driving said corresponding sound generator with, or responsive to, an analog signal from a digital-to-analog converter responsive to a digital waveform signal.

16. A method of receiving and processing at least one auscultatory sound signal from a corresponding at least one auscultatory sound-or-vibration sensor as recited in claim 15, wherein said digital waveform signal is stored in, and recalled from, memory.

17. A method of receiving and processing at least one auscultatory sound signal from a corresponding at least one auscultatory sound-or-vibration sensor as recited in claim 15, wherein said digital waveform signal is generated in real time responsive to a stored program.

18. A method of receiving and processing at least one auscultatory sound signal from a corresponding at least one auscultatory sound-or-vibration sensor as recited in claim 3, wherein said corresponding at least one auscultatory sound signal from said corresponding at least one auscultatory sound-or-vibration sensor is received following the completion of steps a-e of claim 1 for said corresponding at least one auscultatory sound-or-vibration sensor.

19. A method of receiving and processing at least one auscultatory sound signal from a corresponding at least one auscultatory sound-or-vibration sensor as recited in claim 4, wherein said corresponding at least one auscultatory sound signal from said corresponding at least one auscultatory sound-or-vibration sensor is received following the completion of steps a-e of claim 1 for said corresponding at least one auscultatory sound-or-vibration sensor.

20. A method of receiving and processing at least one auscultatory sound signal from a corresponding at least one auscultatory sound-or-vibration sensor as recited in claim 5, wherein said corresponding at least one auscultatory sound signal from said corresponding at least one auscultatory sound-or-vibration sensor is received following the completion of steps a-e of claim 1 for said corresponding at least one auscultatory sound-or-vibration sensor.

21. A method of receiving and processing at least one auscultatory sound signal from a corresponding at least one auscultatory sound-or-vibration sensor, comprising:
  a. placing the corresponding at least one auscultatory sound-or-vibration sensor in proximity to a corresponding sound generator;
  b. applying an auscultatory sound-or-vibration sensor electronic test signal to said corresponding sound generator, wherein said auscultatory sound-or-vibration sensor electronic test signal comprises a plurality of frequency components, each frequency component of said plurality of frequency components comprises an integral number of wavelengths, and each said frequency component is terminated following a duration of time corresponding to said integral number of wavelengths of said frequency component after said frequency component of said auscultatory sound-or-vibration sensor electronic test signal is applied to said corresponding sound generator, wherein the operation of applying said auscultatory sound-or-vibration sensor electronic test signal to said corresponding sound generator comprises driving said corresponding sound generator with, or responsive to, an analog signal from a digital-to-analog converter responsive to a digital waveform signal, wherein said digital waveform signal is generated in real time responsive to a stored program, wherein said digital waveform signal is generated in real time responsive to a plurality of STFT frame-synchronized sinusoidal test frequencies and a number of points of an associated Short Time Fourier Transform (STFT), wherein each STFT frame-synchronized sinusoidal test frequency of said plurality of STFT frame-synchronized sinusoidal test frequencies has a corresponding integral number of wavelengths within a time-frame interval of said associated Short Time Fourier Transform (STFT), and said STFT frame-synchronized sinusoidal test frequency is an integer factor times a ratio of a sampling frequency divided by said number of points of said associated Short Time Fourier Transform (STFT);

c. generating an acoustic sound signal from said corresponding sound generator responsive to said auscultatory sound-or-vibration sensor electronic test signal;

d. exposing said corresponding at least one auscultatory sound-or-vibration sensor to said acoustic sound signal and receiving a corresponding at least one auscultatory sound signal responsive thereto; and e. determining whether or not said corresponding at least one auscultatory sound-or-vibration sensor is functioning properly responsive to an analysis of a Fourier Transform of said corresponding at least one auscultatory sound signal.

\* \* \* \* \*